(12) United States Patent
Vater et al.

(10) Patent No.: US 9,074,214 B2
(45) Date of Patent: Jul. 7, 2015

(54) USE OF SPIEGELMERS

(71) Applicant: NOXXON Pharma AG, Berlin (DE)

(72) Inventors: Axel Vater, Berlin (DE); Christian Maasch, Berlin (DE); Sven Klussmann, Berlin (DE); Werner Purschke, Berlin (DE); Dirk Eulberg, Berlin (DE); Florian Jarosch, Berlin (DE); Klaus Buchner, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

(21) Appl. No.: 13/953,797

(22) Filed: Jul. 30, 2013

(65) Prior Publication Data

US 2013/0337049 A1    Dec. 19, 2013

Related U.S. Application Data

(62) Division of application No. 11/913,526, filed as application No. PCT/EP2006/004180 on May 4, 2006, now Pat. No. 8,497,250.

(30) Foreign Application Priority Data

May 4, 2005    (DE) .......................... 10 2005 020 874

(51) Int. Cl.
    *C12N 15/115*    (2010.01)
(52) U.S. Cl.
    CPC .......... *C12N 15/115* (2013.01); *C12N 2310/16* (2013.01); *G01N 2500/04* (2013.01)
(58) Field of Classification Search
    None
    See application file for complete search history.

(56) References Cited

U.S. PATENT DOCUMENTS

| 7,595,304 | B2 | 9/2009 | Zhao et al. |
| 7,727,969 | B2 | 6/2010 | Farokhzad et al. |
| 2004/0048819 | A1 | 3/2004 | Simon et al. |
| 2004/0248842 | A1 | 12/2004 | Wagner et al. |
| 2005/0163844 | A1 | 7/2005 | Ashton et al. |
| 2007/0154529 | A1* | 7/2007 | Bullerdiek ............... 424/445 |
| 2010/0233152 | A1 | 9/2010 | Bullerdiek et al. |

FOREIGN PATENT DOCUMENTS

| DE | 10211558 | 10/2003 |
| WO | 03094973 | 11/2003 |
| WO | WO 2004/061456 | * 7/2004 |
| WO | 2005018537 | 3/2005 |

OTHER PUBLICATIONS

Scala et al., "Adenovirus . . . neoplasms," PNAS 97:4256-4261, 2000.
Schlueter et al., "HGMA1 . . . plaquest," Path Res Prac 201:101-107, 2005.
Zhu et al., "Amphiphilic . . . carriers," Bioconj Cehm 16:139-146, 2005.
Duzgunes et al., "Liposome . . . cells," Mol Memb Biol 16:111-116, 1999.
Eulberg & Klussmann, "Spiegelmers: Biostable Aptamers," ChemBioChem 4:979-983, 2003.
Ferguson et al., "Delivery . . . activity," BBRC 344:792-797, 2006.
Mishra et al., "PEGylation . . . particles," Eur J Cell Biol 83:97-111, 2004.
Patil et al., "DNA . . . Review," AAPS J 7:E61-E77, 2005.
Shoji et al.,"Current . . . Oligonucleotides," Curr Pharm Design 10:785-796, 2004.
Vater & Klussmann, "Toward . . . Prospects," Curr Opn Drug Disc Dev 6:253-261, 2003.
Vlassov et al."Trasport . . . membranes," Biochim Biophys Acta 1197:95-108, 1994.

* cited by examiner

*Primary Examiner* — Laura B Goddard
(74) *Attorney, Agent, or Firm* — MDIP LLC

(57) ABSTRACT

The present invention relates to the use of a L-nucleic acid as intracellularly active agent.

22 Claims, 23 Drawing Sheets

| Name | Alias | Sequence | Case | H | $K_D$ | A |
|---|---|---|---|---|---|---|
| 132-C3 | NOX-h | GCUGCUGCAAAUUGACGGGGGCGUGGUUGGGGCGGGUCGAUUGCAGC | 1A | 12 | 12nM | 78 |
| 132-B3 | NOX-f | GCUGAAUGAGGAUCGCAGGGGCGUGGCUGGGGUGGCGACCGUUCAGC | 1A | 5 | 9nM | 92 |
| 132-C4 |  | GCUGCGCAAGGAGAGGGGCGCGGUUGGGGAGGCUCUAAGGCUGCAGC | 1A | 1 | 14nM | 78 |
| 132-E2 |  | GCUGGCGCUAUAGGACAGGGGUGCGGUUGGGGCGGUCCGCUGUCAGC | 1B | 1 | 14nM | 79 |
| 132-A2 |  | GCUGGAUAGAACGCAGGGGUGCGGUUUGGGGAGGCGUGAUAUGCAGC | 1A | 1 | 13nM | 82 |
| 132-H1 | NOX-i | GCUGCCGUAAAGAGGGGUGAGGUUGGGGAGGCUUUACGGUUCAGC | 1A | 1 | 8nM | 77 |
| 132-F1 |  | GCUGCAUGCCGCGAUCAGGGGAGCGGUUGGGGCGGGAUCCGGCUCAGC | 1A | 1 | 22nM | 63 |
| 132-G2 | NOX-g | GCUGCGAGGGAGGUAGCGGCUCUGCGCGUGACGUGGGUGGAUGCAGC | 2A | 1 | 12nM | 64 |
| 122-A1 | NOX-A | GGCUGAUACGUGGGUGGAUAUGGGGCAGUUCCAUGUGGGUGGUUUCAGCC | 2A | 10 | 18nM | 94 |
| 122-C1 |  | GGCUGAUACGUGGGUGAAUAUGGGGCAGUUCCAUGUGGGUGGUUUCAGCC | 2A | 1 | 16nM | 87 |
| 122-B2 | NOX-B | GGCUGAUACGUGGGUGGAAAGGUGAAACUACCUGUGGGAGGUUUCAGCC | 2A | 3 | 22nM | 92 |
| 122-E2 | NOX-C | GGCUGGCACUCGCAGGGGUGAAGUGAUGAUUGGGGUGGCCGAGACCAGCC | 2B | 1 | 12nM | 85 |
| 122-G2 | NOX-E | GGCUGCCGAGUGGUUGGGGUGUGUAAGGGAGGUGGAAUCCGCGGGCAGCC | 1° | 1 | 11nM | 85 |
| 122-B4 | NOX-D | GGCUGUUCGUGGGAGGAAGGCUCUUGGAUAGAGUCGUGGGUGGUUCAGCC | 2A | 1 | 15nM | 85 |

Helix A1/A2 (5'+3' terminal of the total sequence)   H = Frequency of the sequence Box A1 and Box A2 (Binding motif)   $K_D$ = Dissociation constant determined Helix B1/B2 (5'+3' terminal of Box A)   in the equilibrium binding assay Helix C1/C2 (between the Box A1 and Box A2)   A = Activity [%]

Fig. 1A

| Name | Alias | Helix A1 | Helix B1 | Box A1 | Helix C1 | Helix C2 | Box A2 | Helix B2 | Helix A2 |
|---|---|---|---|---|---|---|---|---|---|
| *Case 1A* | | | | | | | | | |
| 132-C3 | NOX-h | X | X | X | - | - | X | X | X |
| 132-C4 | | X | X | X | - | - | X | X | X |
| 132-A2 | | X | X | X | - | - | X | X | X |
| 132-H1 | NOX-i | X | X | X | - | - | X | X | X |
| 132-F1 | | X | X | X | - | - | X | X | X |
| 122-G2 | NOX-E | X | X | X | - | - | X | X | X |
| 132-B3 | NOX-f | X | X | X | - | - | X | X | X |
| *Case 1A shortened* | | | | | | | | | |
| 132-B3 32nt | NOX-f 32nt | - | X | X | - | - | X | X | - |
| 132-B3 32nt | NOX-f 33nt | - | X | X | - | - | X | X | - |
| *Case 1B* | | | | | | | | | |
| 132-E2 | | X | X | X | - | - | X | X | X |
| *Case 2A* | | | | | | | | | |
| 132-G2 | NOX-g | X | - | X | X | X | X | - | X |
| 122-A1 | NOX-A | X | - | X | X | X | X | - | X |
| 122-C1 | | X | - | X | X | X | X | - | X |
| 122-B2 | NOX-B | X | - | X | X | X | X | - | X |
| 122-B4 | NOX-D | X | - | X | X | X | X | - | X |
| *Case 2B* | | | | | | | | | |
| 122-E2 | NOX-C | X | X | X | X | X | X | X | X |

Fig. 1B

```
HMGA1a human (Seq. ID 18):  (M)SESSSKSSQPLASKQEKDGT---EKRGRGREFRKQPPVSPGTALVGSQKEPSEVPTEKRPRGRPKGSKNK  (66)
HMGA1b human (Seq. ID 19):  (M)SESSSKSSQPLASKQEKDGT---EKRGRGREFRKQPP----------KEPSEVPTEKRPRGRPKGSKNK  (55)
HMGA2  human (Seq. ID.20):  (M)SARGEGAGQPSTSAQGQPAAPAPQKRGRGREFRKQQQ---------EPTGEPSEKRPRGRPKGSKNK    (57)
                                                        DBD1                                  DBD2

HMGA1a human (Seq. ID 18):  GAAKT--RKTTTTPGRKPRGREKK------EEEEGISQESSEEEQ 106
HMGA1b human (Seq. ID 19):  GAAKT--RKTTTTPGRKPRGREKK------LEK----EEEEGISQESSEEEQ 95
HMGA2  human (Seq. ID.20):  SPSKAAQKKAEATGEKRPRGRERKWPQQVVQKKPAQEETEETSSQESAEED 108
                                          DBD3
```

DBD1-3: DNA-binding domain 1-3 ("AT hooks")

HMGA1a/b Target molecule domain (Seq. ID 17):  EPSEVPTPKRPRGRPKGSKNK

Fig. 2: Sequence comparison of HMGA1a/b and HMGA2

| Name | Alias | Sequence | L | $K_D$ | A |
|---|---|---|---|---|---|
| 132-B3 | NOX-f | GCUGAAUGAGGAUCGCAGGGGCGUGGCUGGGGUGGGCGACCGUUCAGC | 48 | 9 nM | 92 |
| 132-B3 | NOX-f | GGAUCGCCAGGGGCGUGGCUGGGGUGGGCGACC | 32 | 21 nM | 90 |
| 132-B3 | NOX-f | GGAUCGCCAGGGGCGUGGCUGGGGUGGGCGAUCC | 33 | 14 nM | 90 |

Helix A1/A2 (5'+3' terminal of the total sequence)

Box A1 and Box A2 (Binding motif)

Helix B1/2 (5'+ 3' terminal of Box A1/2)

L = Length [Number of nucleotides]

$K_D$ = Dissociation constant determined in the equilibrium binding assay

A = Activity [%]

Fig. 3

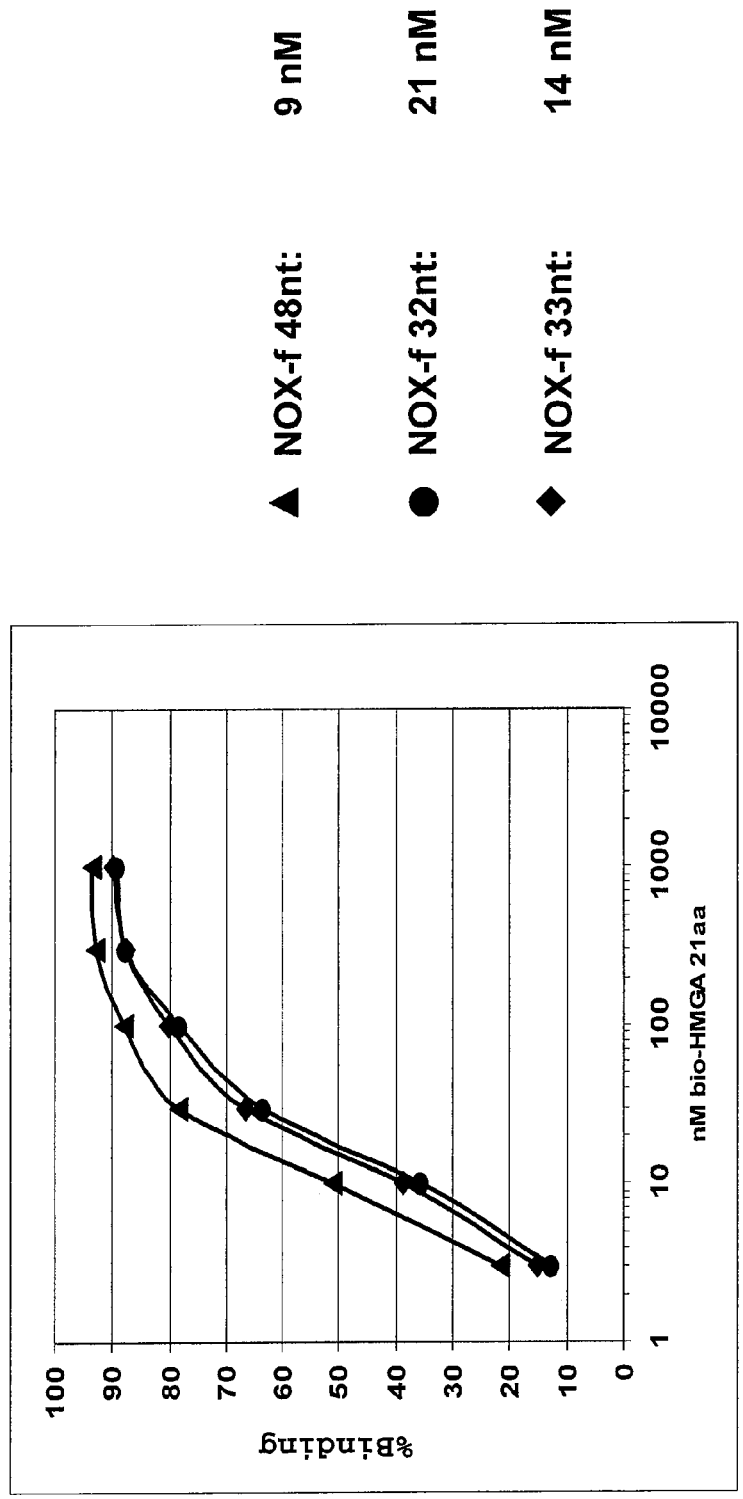
Fig. 4: Binding properties of shortened HMGA1a/b-binding aptamer NOX-f

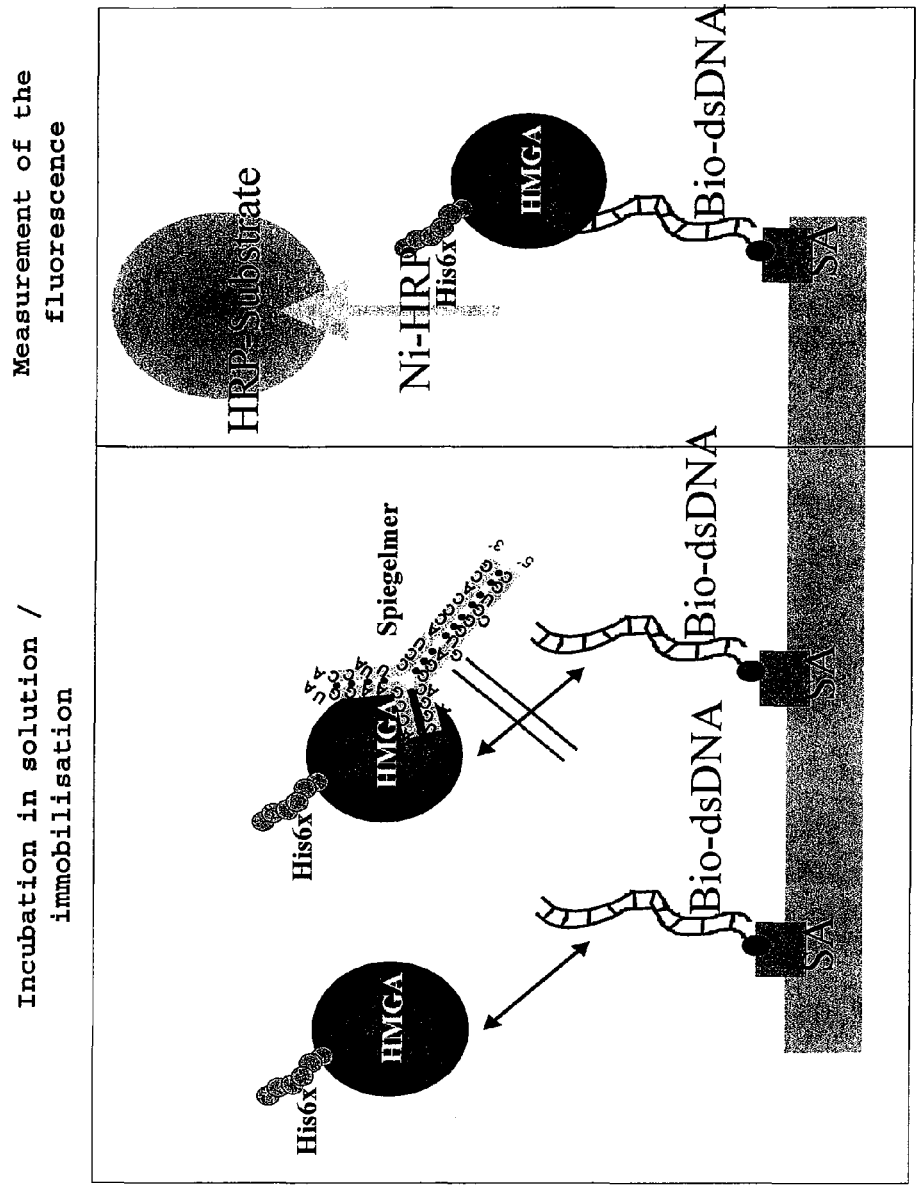
Fig. 5: Competition assay for measuring the binding of HMGA1b to the double-strand natural target DNA in the multiwell plate assay

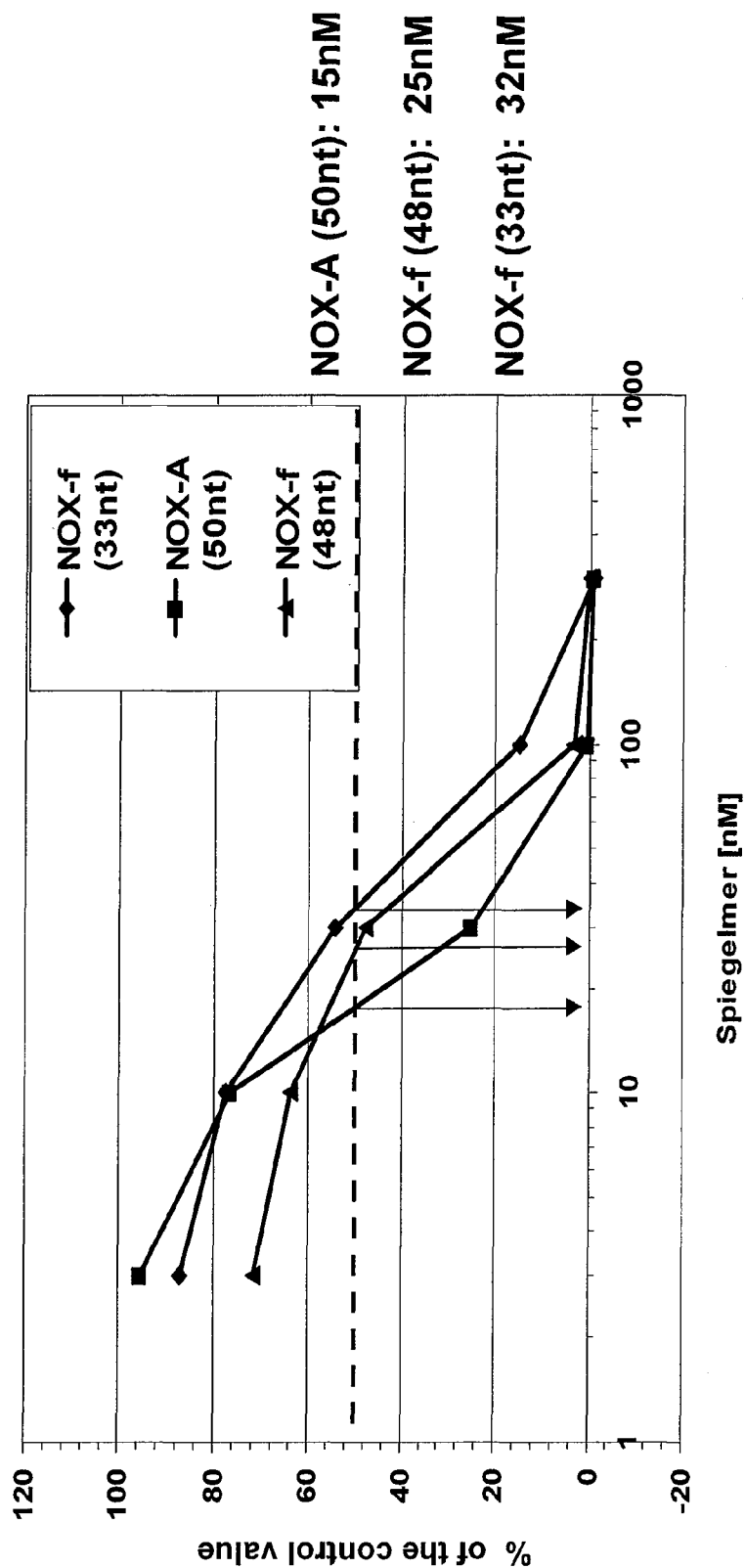
Fig. 6: Comparison of NOX-A and NOX-f (48nt; 33nt) in the competitive Multiwell plate assay

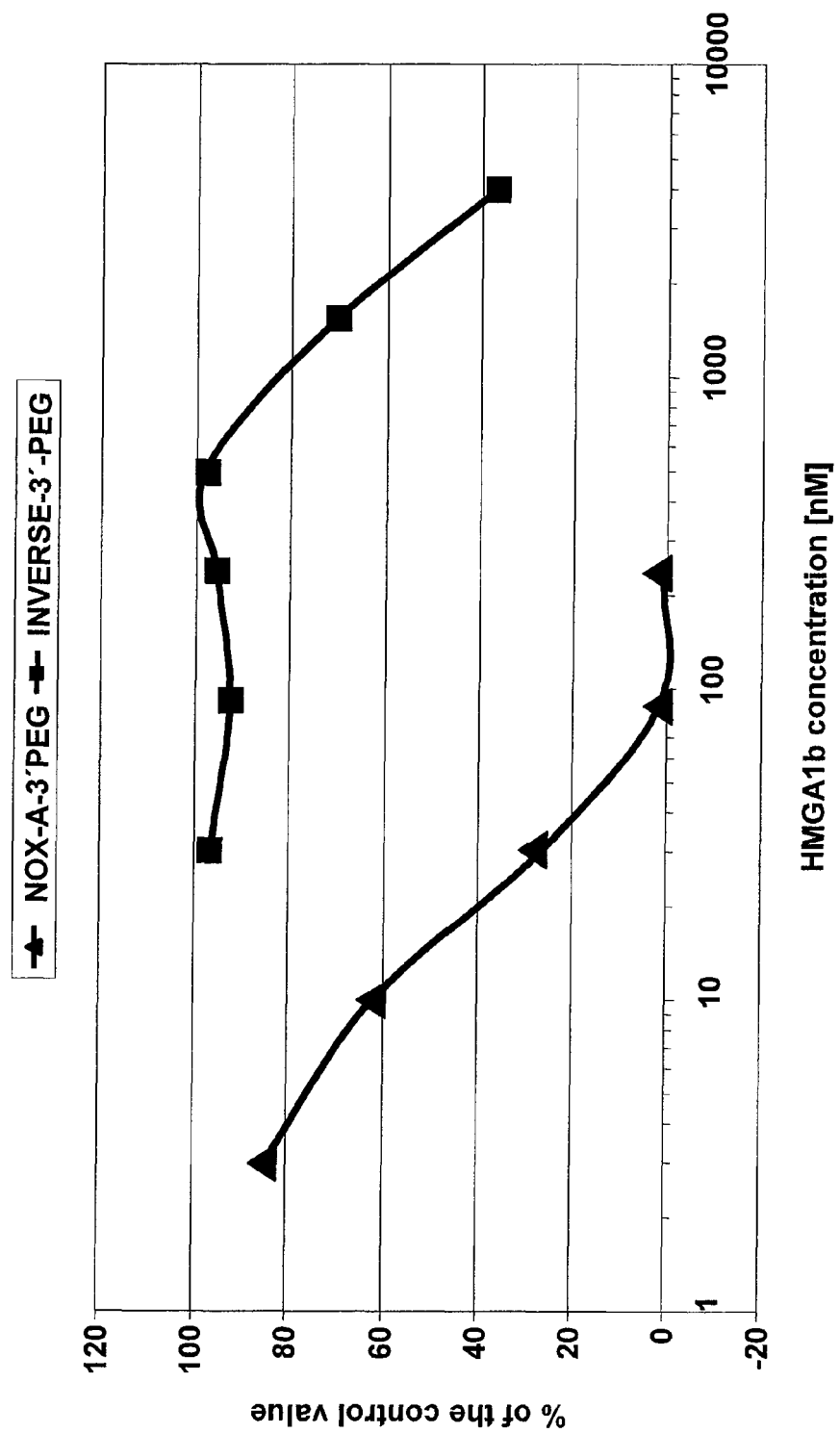
Fig. 7: Activity of 2kDa-PEG-coupled NOX-A as well as non-functional control spiegelmer in the competitive Multiwell plate assay

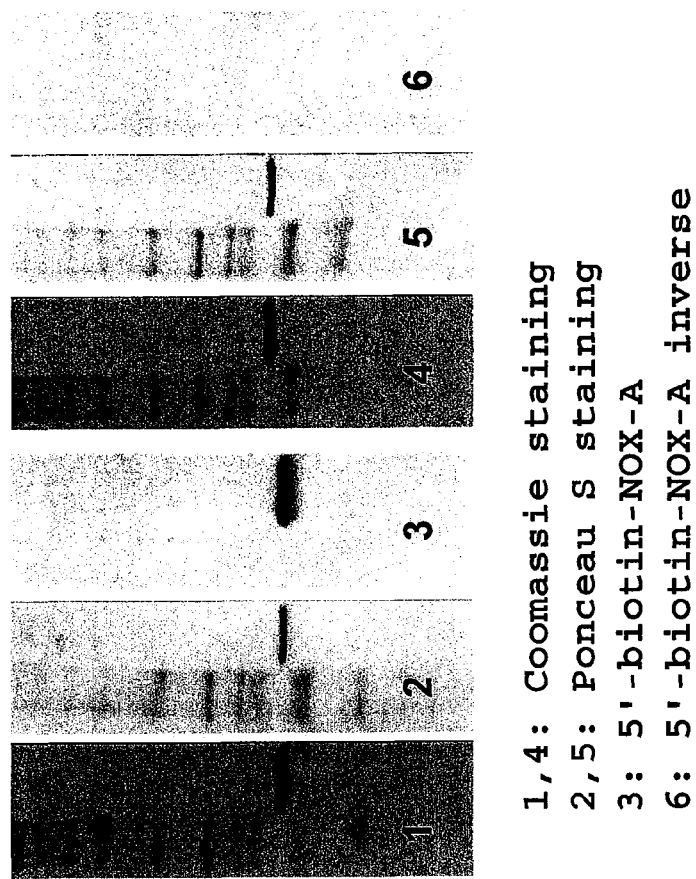
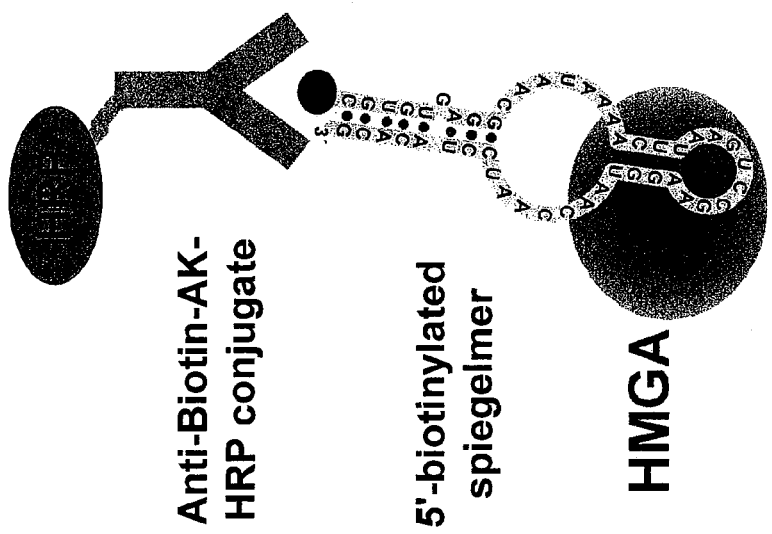
1, 4: Coomassie staining
2, 5: Ponceau S staining
3: 5'-biotin-NOX-A
6: 5'-biotin-NOX-A inverse
Fig. 8: Western Blot; Detection of immobilised HMGA1b by biotinylated spiegelmer

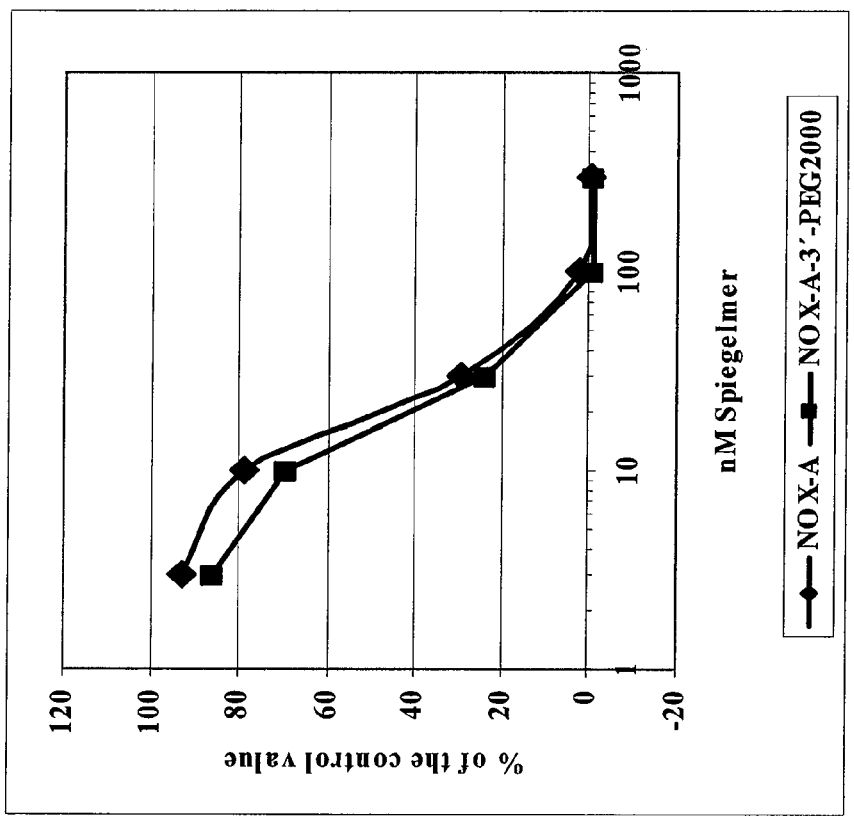
Fig. 9: Activity of free and PEGylated spiegelmer NOX-A in the competitive Multiwell plate assay

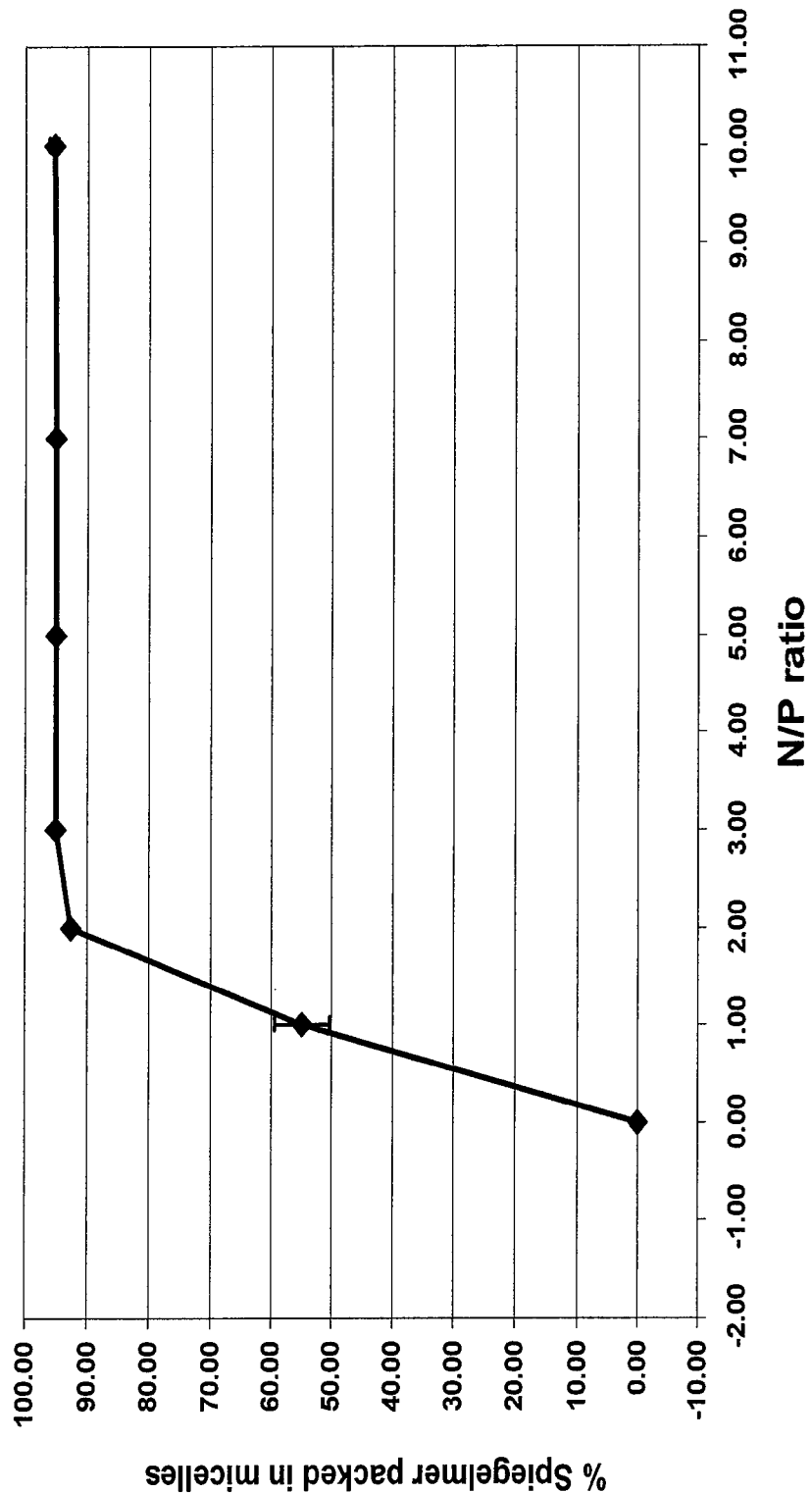
Fig. 10: Detection of the packing of PEGylated spiegelmer in micelles by "RiboGreen exclusion assay"

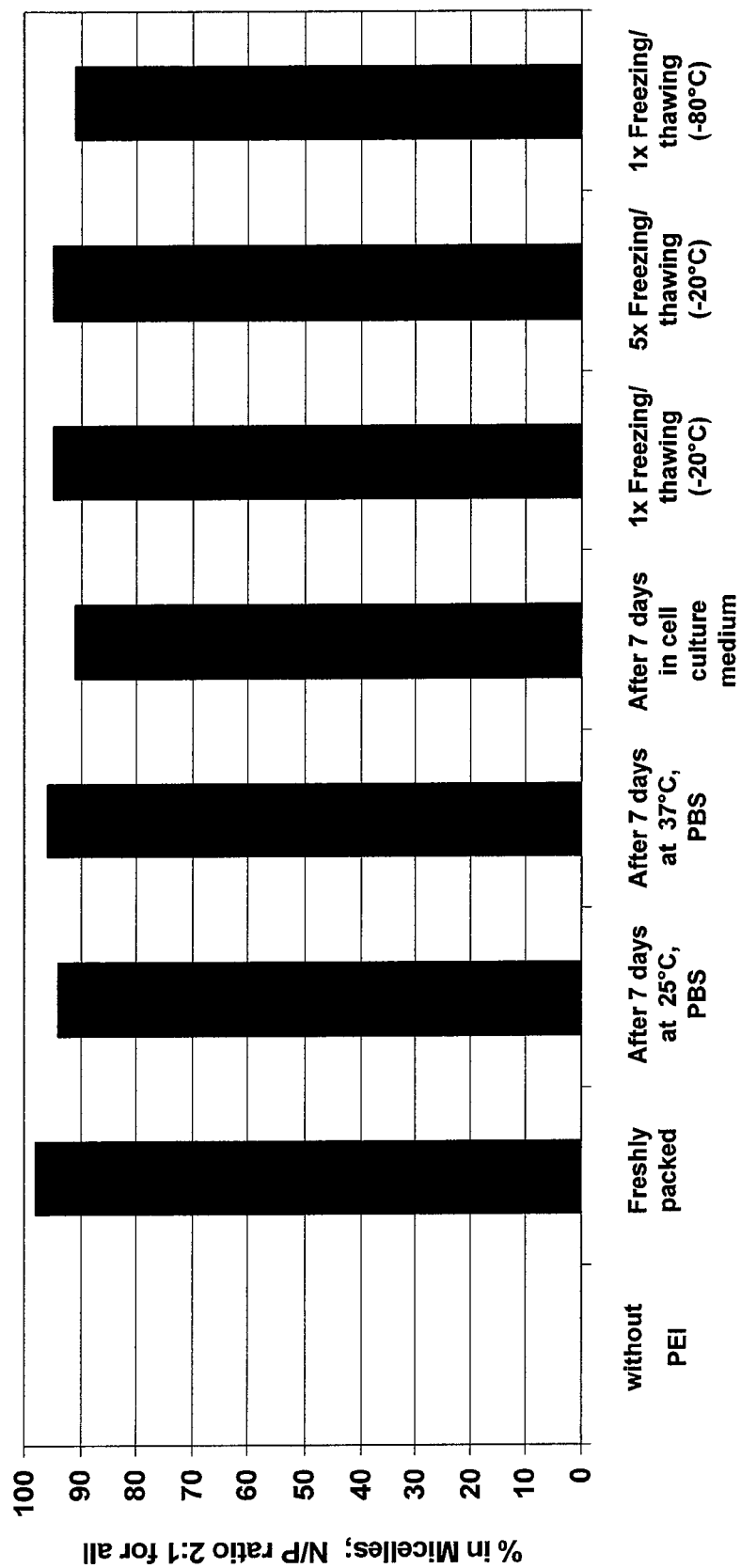
Fig. 11: Stability of PEI-spiegelmer micelles in the "RiboGreen exclusion assay"

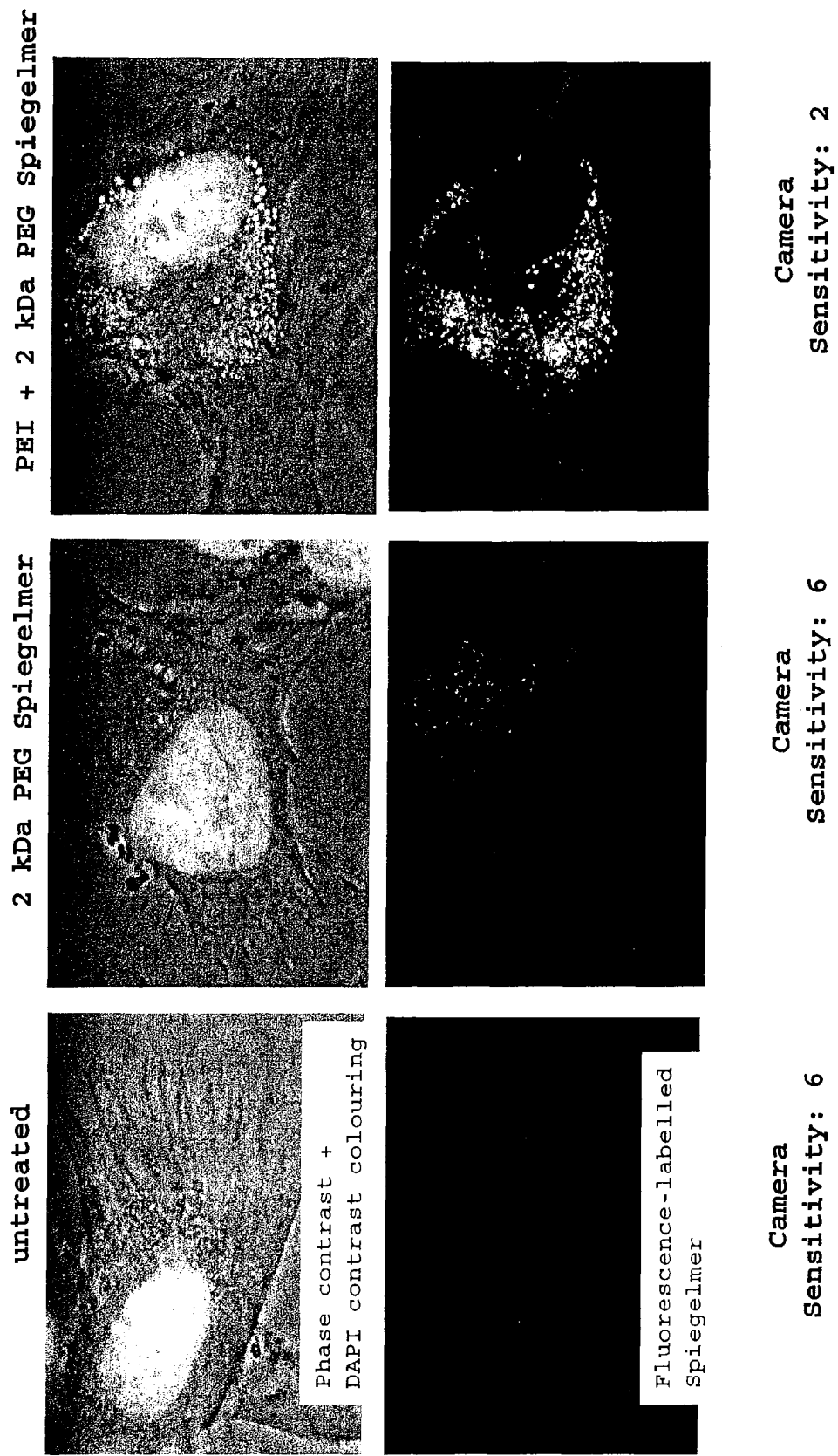
Fig. 12: Efficient uptake of spiegelmer packed in PEI micelles

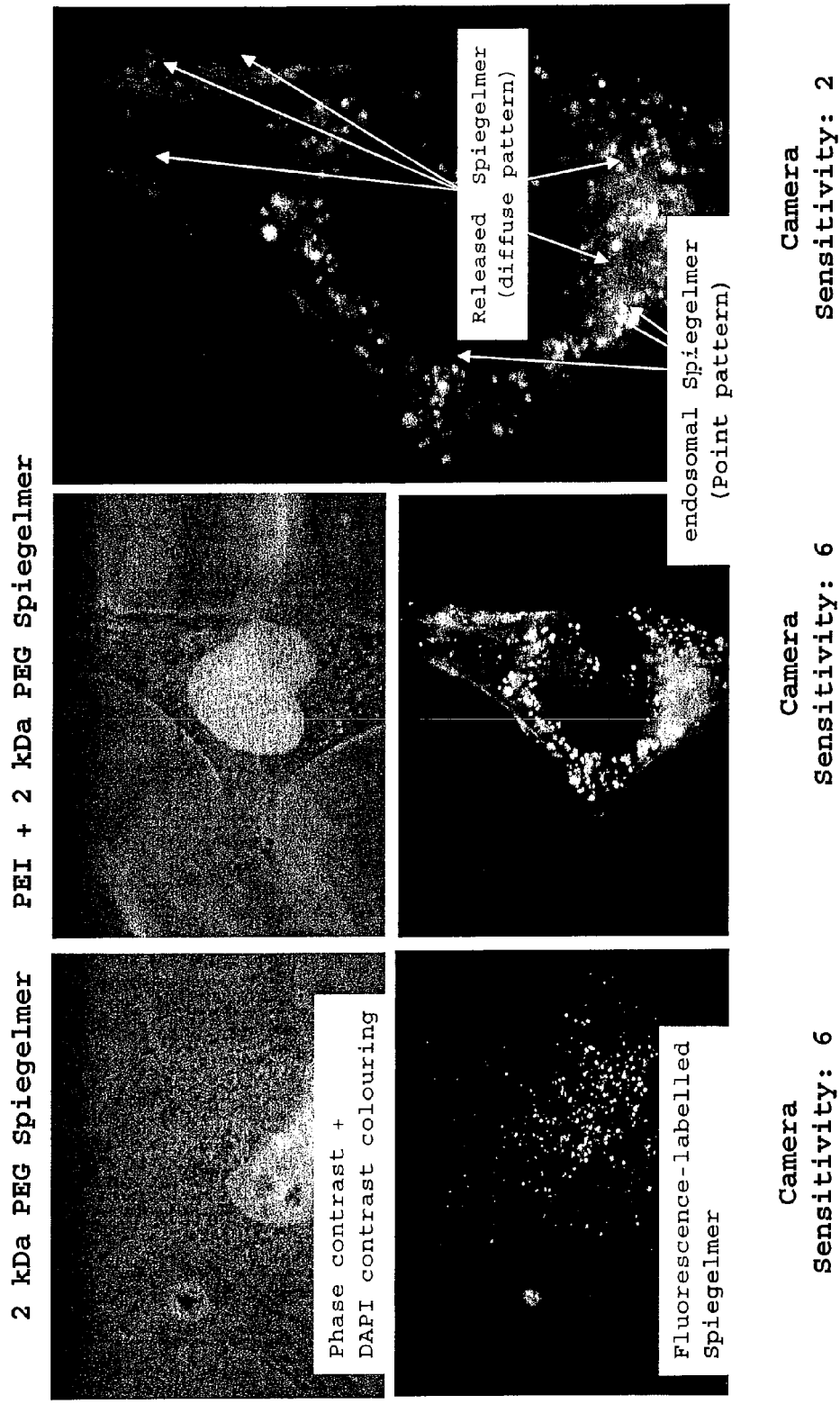
Fig. 13: Release of Spiegelmer from the endosomal compartment

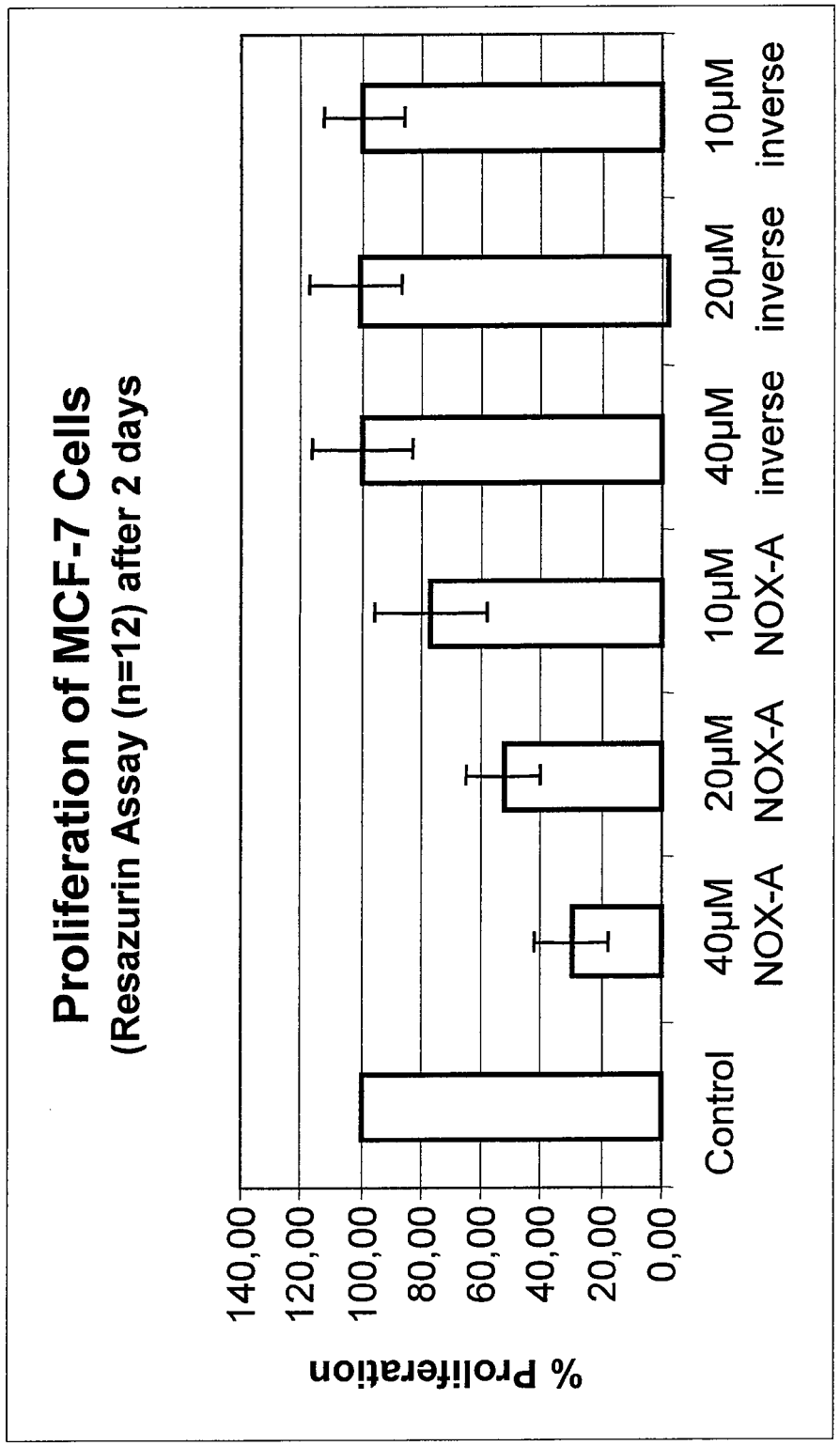
Fig. 14: Proliferation assay with "naked" Spiegelmer

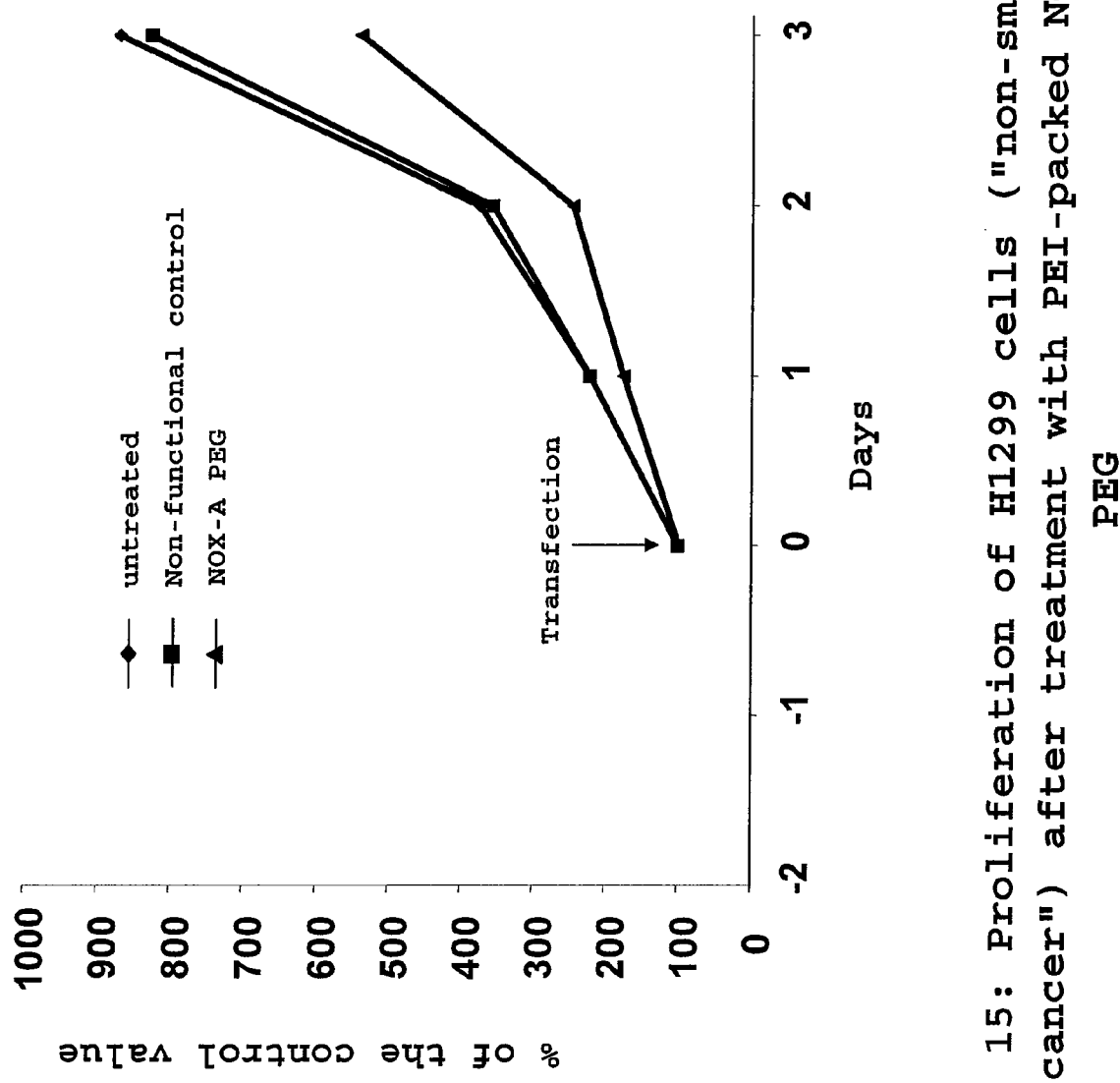
Fig. 15: Proliferation of H1299 cells ("non-small cell lung cancer") after treatment with PEI-packed NOX-A-2kDa PEG

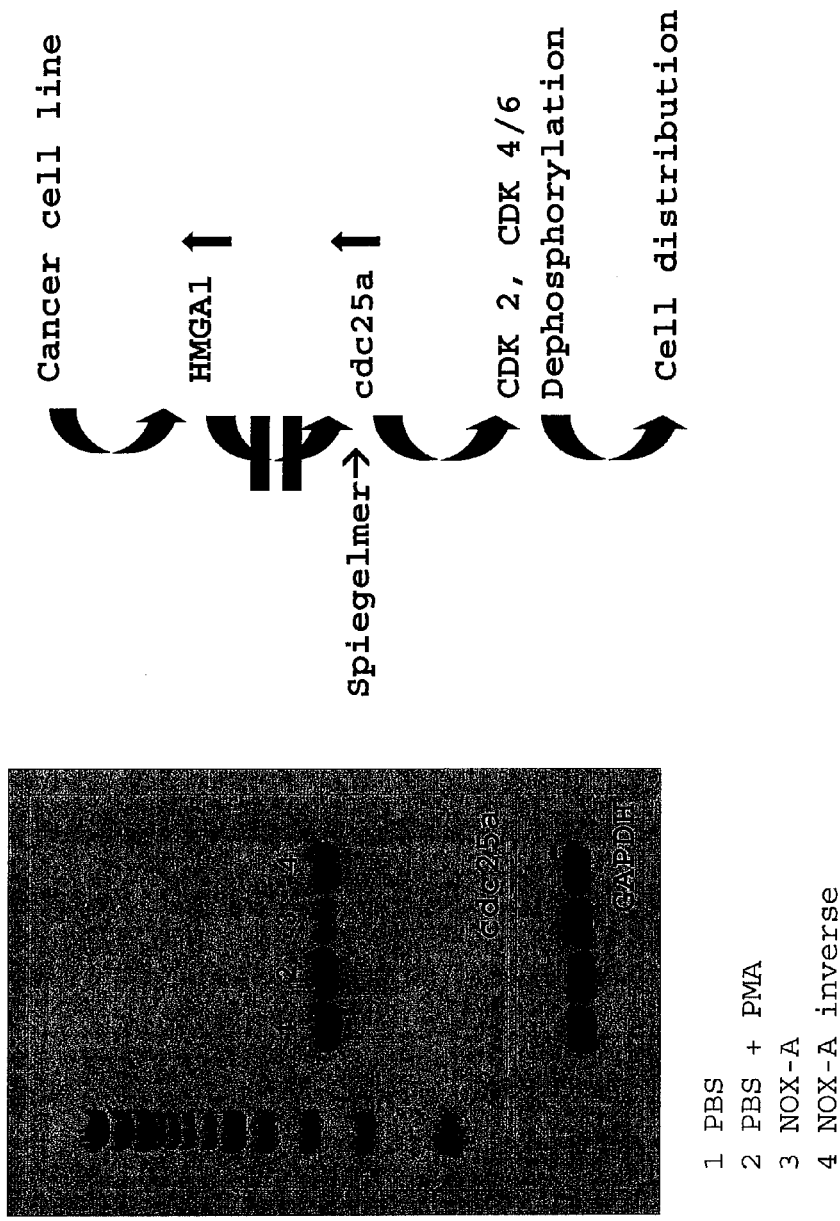
Fig. 16: Inhibition of the HMGA-induced *cdc25a* Gene expression, detected by quantitative RT-PCR

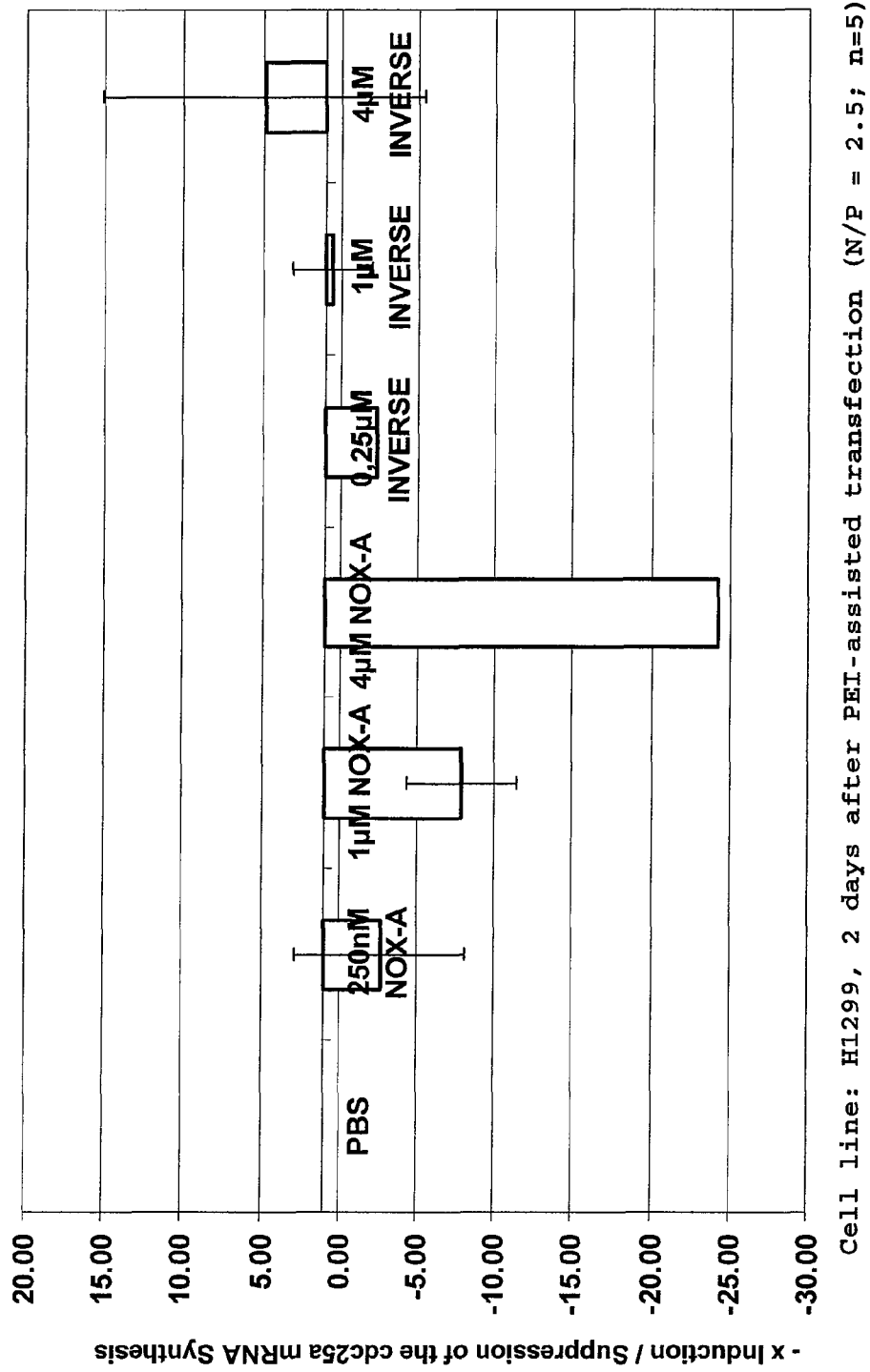
Fig.17: Dose-dependent inhibition of the cdc25a mRNA expression by NOX-A

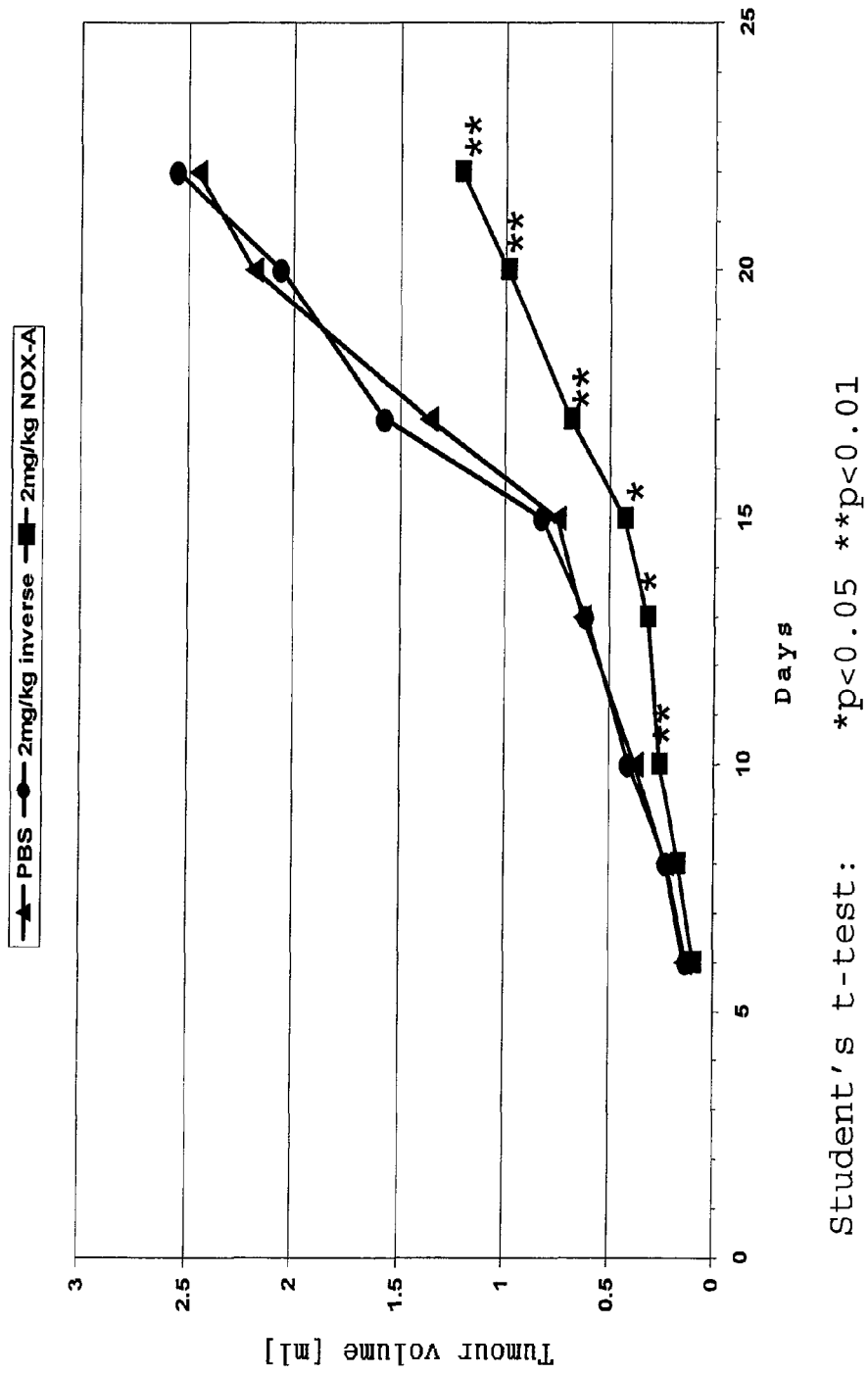
Fig.18: Inhibition of tumour growth in the xenograft model in naked mice by the Spiegelmer NOX-A

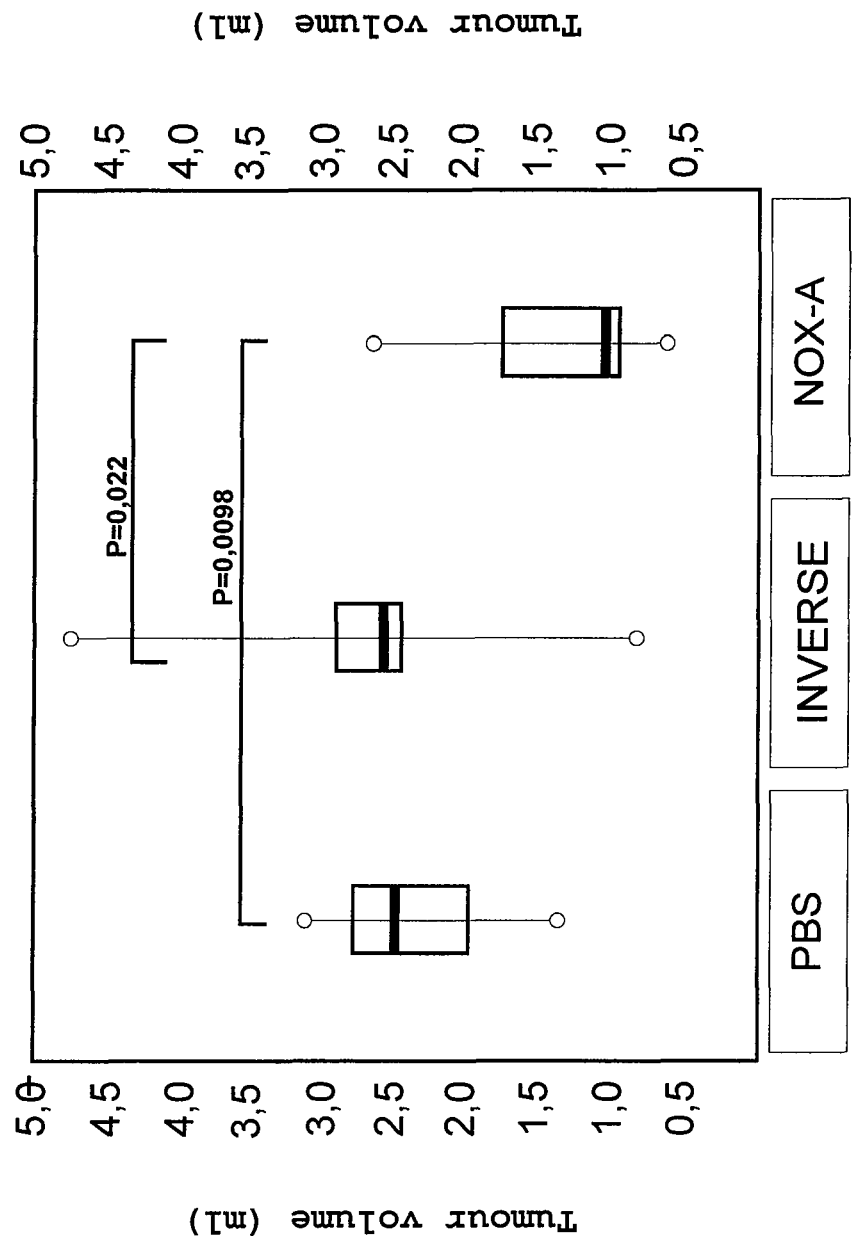
Fig.19: Statistical analysis of the data from the xenograft experiment

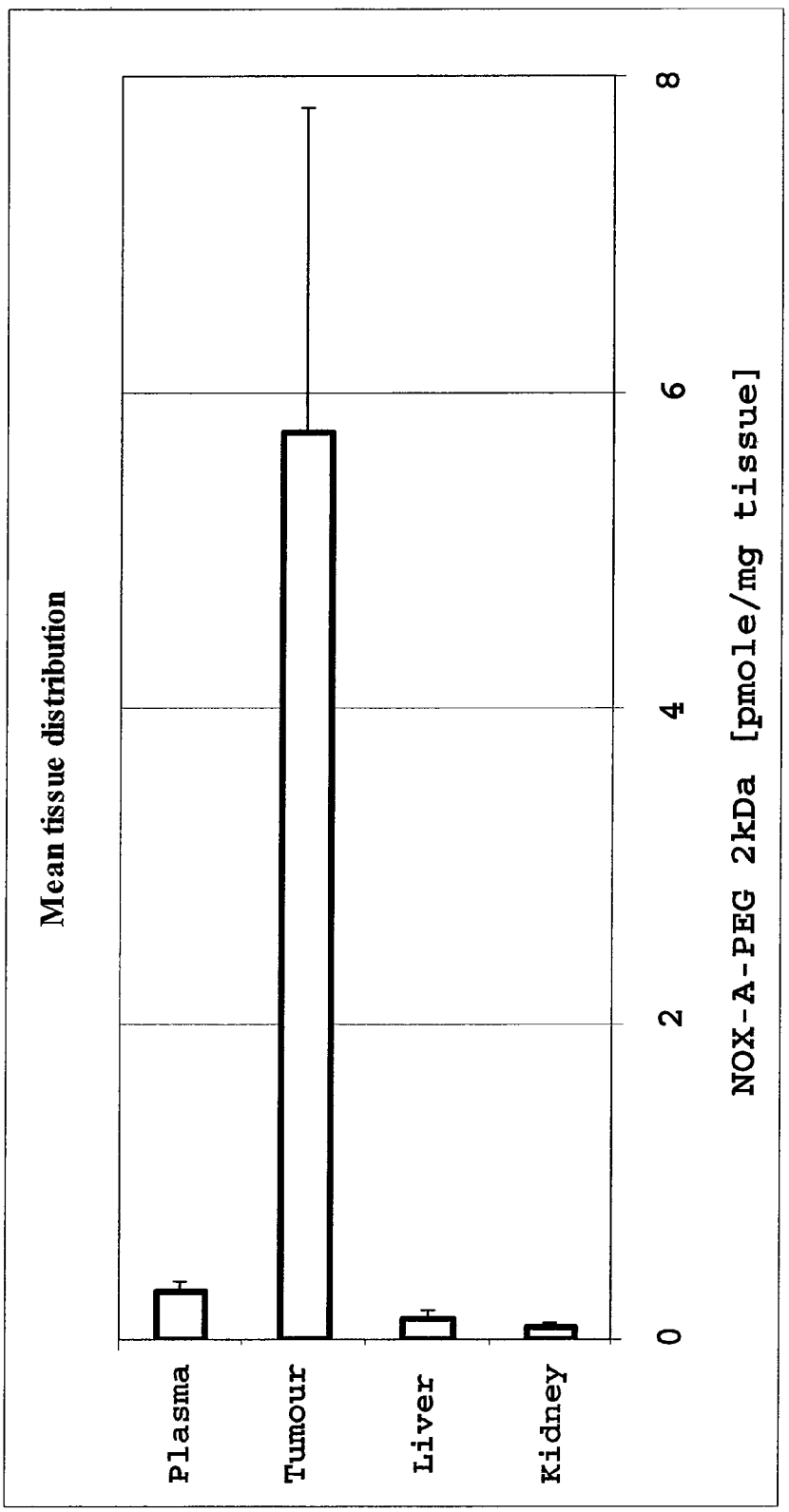
Fig. 20: Tissue distribution of NOX-A in the xenograft experiment

Tissue distribution of packed and unpacked Spiegelmer 24 and 96 hours after last injection

| | 24 hours after last injection | | 96 hours after last injection | |
|---|---|---|---|---|
| | Spiegelmer [pmole/mg tissue] | Spiegelmer Micelles [pmole/mg tissue] | Spiegelmer [pmole/mg tissue] | Spiegelmer Micelles [pmole/mg tissue] |
| Plasma | 2,950 ± 0,438 | 1,930 ± 2,729 | 0,150 ± 0,212 | 0,830 ± 0,778 |
| Brain | 0,000 ± 0,000 | 0,030 ± 0,000 | 0,000 ± 0,000 | 0,000 ± 0,000 |
| Heart | 0,055 ± 0,078 | 0,050 ± 0,000 | 0,040 ± 0,057 | 0,040 ± 0,057 |
| Lungs | 0,010 ± 0,014 | 0,000 ± 0,000 | 0,000 ± 0,000 | 0,000 ± 0,000 |
| Liver | 0,310 ± 0,014 | 0,025 ± 0,035 | 0,070 ± 0,042 | 0,070 ± 0,000 |
| Kidneys | 0,595 ± 0,092 | 0,310 ± 0,212 | 0,105 ± 0,035 | 0,160 ± 0,085 |
| Gall bladder | 0,120 ± 0,057 | 0,070 ± 0,099 | 0,000 ± 0,000 | 0,560 ± 0,792 |
| Pancreas | 0,070 ± 0,057 | 0,040 ± 0,000 | 0,000 ± 0,000 | 2,700 ± 2,531 |
| Tumour | 0,840 ± 0,255 | 24,925 ± 13,301 | 0,120 ± 0,057 | 11,325 ± 7,050 |

Fig. 21

USE OF SPIEGELMERS

One aspect of the present invention relates to a new use of spiegelmers. Another aspect of the present invention relates to spiegelmers that bind HMG proteins.

With advances in molecular medicine it has become possible to identify target molecules involved in a disease or a disease state and to act on these specifically so as thereby to treat or prevent the disease or the disease state or at least to alleviate the symptoms associated therewith. The target molecules can in principle be divided into two groups. A first group includes target molecules that are present extracellularly and can thus in principle be brought into contact with an active substance by administering the latter in a body fluid or a body cavity that contains the target molecule. The first group of target molecules is herein also referred to as extracellular target molecules. The second group of target molecules includes target molecules that are present in cells, these cells being involved in the disease to be treated or in the predisposition to the disease. It is not necessary in this connection for the target molecule to be directly responsible for the disease state or directly connected with the predisposition to the disease. Instead, it is sufficient if the respective target molecule is involved in an action cascade, the course of which is influenced by the active substance, with the result that the active substance is suitable for the treatment or prevention of the disease. The second group of target molecules is herein also referred to as intracellular target molecules.

The nature of the target molecule, i.e. extracellular or intracellular target molecule, determines in principle the binding class, with which an attempt can be made to effect the interaction, necessary for the therapeutic or preventive action, between the active substance, typically the pharmaceutical active substance, and the target molecule. In virtually all cases so-called small molecules can be used, i.e. chemical compounds with a molecular weight of typically 1000 daltons or less. These molecules can interact in the desired manner directly with extracellular target molecules, as well as with intracellular target molecules.

Against this background new classes of active substances have been developed by the biotechnology industry, such as for example antibodies, in particular monoclonal antibodies, antisense molecules, siRNA molecules, aptamers and spiegelmers. Although some of these classes of molecules are still in the preliminary stage of clinical investigations, there exist at least in the case of antibodies and antisense molecules products that are already in clinical use. However, with these new classes of substances there are also significant problems as regards addressing intracellular target molecules. Thus, for example, the intracellular use of antibodies is currently still not always possible, at least not to an extent or in a way and manner that allows a routine use in patients of antibodies directed against intracellular target molecules for the purposes of treatment and/or prophylaxis. Also, the other new classes of active substances, in particular antisense molecules and siRNA molecules, must on account of their action mechanism be introduced into the respective cell containing the target molecule or the gene coding for the target molecule. The targeted release of the active substance, also termed delivery, is also for these classes of substances the currently limiting factor for a clinical application.

The same is also true of aptamers and spiegelmers, i.e. functional nucleic acids with a defined three-dimensional structure that allows the specific interaction with the respective target molecules. The use of aptamers in order to address intracellular target molecules utilises methods of gene technology, more specifically gene therapy. The aptamers, also termed intramers, directed against an intracellular target molecule are incorporated into the respective target cell by means of gene technology methods. Such an approach is however also subject to considerable limitations, not least on account of the lack of acceptance of treatment approaches based on gene therapy. In particular the route adopted in the case of intramers, involving intracellular expression of a nucleic acid coding intracellularly for the respective aptamer, is in principle closed to spiegelmers, since no biological system exists which would be capable of synthesising spiegelmers, i.e. aptamers consisting of L-nucleotides.

The object of the present invention is accordingly to provide a class of substances that is able to interact specifically with intracellular target molecules, i.e. target molecules that are present in a cell.

According to the invention this object is achieved by the subject-matter of the accompanying independent claims. Preferred embodiments are disclosed in the sub-claims.

According to the present invention the basic object is achieved by the subject-matter of the independent claims. Preferred embodiments are disclosed in the sub-claims.

According to a first aspect of the invention the object is achieved by the use of a L-nucleic acid as intracellular active agent.

In a first embodiment of the first aspect the L-nucleic acid is a spiegelmer.

In a second embodiment of the first aspect, which is also an embodiment of the first embodiment, the L-nucleic acid interacts with an intracellular receptor.

In a third embodiment of the first aspect, which is also an embodiment of the second embodiment, the intracellular receptor is selected from the group comprising molecular receptors, enzymes, chaperone molecules, signal peptides, intracellular structures and metabolic intermediates.

In a fourth embodiment of the first aspect, which is also an embodiment of the second embodiment, the intracellular receptor is selected from the group comprising polypeptides, carbohydrates, nucleic acids, lipids and combinations thereof.

In a fifth embodiment of the first aspect, which is also an embodiment of the second, third and fourth embodiment, the L-nucleic acid interacts with an intracellular receptor within a cell.

In a sixth embodiment of the first aspect, which is also an embodiment of the second, third, fourth and fifth embodiment, the intracellular receptor is selected from the group comprising transcription factors and DNA-binding proteins binding an AT hook.

In a seventh embodiment of the first aspect, which is also an embodiment of the sixth embodiment, the intracellular receptor is selected from the group comprising HMG proteins, preferably from the group comprising HMGA1, HMGA1a, HMGA1b, and HMGA2.

According to a second aspect of the present invention this object is achieved by a method for binding an intracellular receptor, comprising:
  providing a cell containing at least one intracellular receptor,
  providing a L-nucleic acid, and
  incubating the cell with the L-nucleic acid.

In a first embodiment of the second aspect the incubation takes place under conditions so that the L-nucleic acid binds to the intracellular receptor in the cell.

In a second embodiment of the second aspect, which is also an embodiment of the first embodiment, the L-nucleic acid is a spiegelmer.

In a third embodiment of the second aspect, which is also an embodiment of the first and second embodiment, after the incubation of the cell with the L-nucleic acid it is determined whether a binding, in particular an intracellular binding, of the L-nucleic acid to the intracellular receptor has taken place.

In a fourth embodiment of the second aspect, which is also an embodiment of the first, second and third embodiment, the intracellular receptor is selected from the group comprising molecular receptors, metabolic intermediates and enzymes.

In a fifth embodiment of the second aspect, which is also an embodiment of the first, second, third and fourth embodiment, the intracellular receptor is selected from the group comprising polypeptides, carbohydrates, nucleic acids, lipids and combinations thereof.

In a sixth embodiment of the second aspect, which is also an embodiment of the first, second, third, fourth and fifth embodiment, the intracellular receptor is selected from the group comprising transcription factors and DNA-binding proteins binding an AT hook.

In a seventh embodiment of the second aspect, which is also an embodiment of the sixth embodiment, the intracellular receptor is selected from the group comprising HMG proteins, and is preferably selected from the group comprising HMGA1, HMGA1a, HMGA1b and HMGA2.

According to a third aspect of the invention this object is achieved by use of a L-nucleic acid to manufacture a medicament for the treatment and/or prevention of a disease, the target molecule of the medicament being an intracellular target molecule.

In a first embodiment of the third aspect the intracellular receptor is selected from the group comprising molecular receptors, enzymes, chaperone molecules, signal peptides, intracellular structures and metabolic intermediates.

In a second embodiment of the third aspect, which is also an embodiment of the first embodiment, the intracellular receptor is selected from the group comprising polypeptides, carbohydrates, nucleic acids, lipids and combinations thereof.

In a third embodiment of the third aspect, which is also an embodiment of the first and second embodiment, the target molecule is selected from the group comprising transcription factors and DNA-binding proteins binding an AT hook.

In a fourth embodiment of the third aspect, which is also an embodiment of the third embodiment, the target molecule is selected from the group comprising HMG proteins, and is preferably selected from the group comprising HMGA1, HMGA1a, HMGA1b and HMGA2.

In a fifth embodiment of the third aspect, which is also an embodiment of the third and fourth embodiment, the disease is selected from the group comprising tumour diseases, virus infections and arteriosclerosis.

In a sixth embodiment of the third aspect, which is also an embodiment of the fifth embodiment, the tumour disease is selected from the group comprising mesenchymal tumours, epithelial tumours, benign tumours, malignant tumours and metastasising tumours.

In a seventh embodiment of the third aspect, which is also an embodiment of the third, fourth, fifth and sixth embodiment, the target molecule is HMGA and the diseases are selected from the group comprising carcinomas of the prostate, pancreas, thyroid, cervix, stomach, breast, colon/rectum, ovaries; pneuroblastomas; lymphomas, uterine leiomyomas; lipomas; endometrial polyps; chondroid hamartomas of the lungs; pleomorphic adenomas of the salivary glands; haemangiopericytomas; chondromatous tumours; aggressive angiomyxomas; diffuse astrocytomas; osteoclastomas; skin cancer; Burkitt's lymphoma; Lewis lung cancer; leukaemia; non-small-cell lung cancer; as well as in each case metastases and/or metastasising forms thereof.

In an eighth embodiment of the third aspect, which is also an embodiment of the fifth embodiment, the arteriosclerosis is triggered or caused by formation of arteriosclerotic plaques mediated by HMGA1, HMGA1a, HMG1b and/or HMGA2.

In a ninth embodiment of the third aspect, which is also an embodiment of the first, second, third, fourth, fifth, sixth, seventh and eighth embodiment, the intracellular target molecule is present intracellularly.

According to a fourth aspect of the invention the object is achieved by the use of a L-nucleic acid for the manufacture of a diagnostic agent for diagnostic purposes, the target molecule of the diagnostic agent being an intracellular target molecule.

In a first embodiment of the fourth aspect the intracellular receptor is selected from the group comprising molecular receptors, enzymes, chaperone molecules, signal peptides, intracellular structures and metabolic intermediates.

In a second embodiment of the fourth aspect, which is also an embodiment of the first embodiment, the intracellular receptor is selected from the group comprising polypeptides, carbohydrates, nucleic acids, lipids and combinations thereof.

In a third embodiment of the fourth aspect, which is also an embodiment of the first and second embodiment, the target molecule is selected from the group comprising transcription factors and DNA-binding proteins binding an AT hook.

In a fourth embodiment of the fourth aspect, which is also an embodiment of the third embodiment, the target molecule is selected from the group comprising HMG proteins, and is preferably selected from the group comprising HMGA, HMGA1a, HMGA1b and HMGA2.

In a fifth embodiment of the fourth aspect, which is also an embodiment of the third and fourth embodiment, the disease is selected from the group comprising tumour diseases, virus infections and arteriosclerosis.

In a sixth embodiment of the fourth aspect, which is also an embodiment of the fifth embodiment, the tumour disease is selected from the group comprising mesenchymal tumours, epithelial tumours, benign tumours, malignant tumours and metastasising tumours.

In a seventh embodiment of the fourth aspect, which is also an embodiment of the third, fourth, fifth and sixth embodiment, the target molecule is HMGA and the disease is selected from the group comprising carcinomas of the prostate, pancreas, thyroid, cervix, stomach, breast, colon/rectum, ovaries; neuroblastomas; lymphomas, uterine leiomyomas; lipomas; endometrial polyps; chondroid hamartomas of the lungs; pleomorphic adenomas of the salivary glands; haemangiopericytomas; chondromatous tumours; aggressive angiomyxomas; diffuse astrocytomas; osteoclastomas; skin cancer; Burkitt's lymphoma; Lewis lung cancer; leukaemia; non-small-cell lung cancer; as well as in each case metastases and/or metastasising forms thereof.

In an eighth embodiment of the fourth aspect, which is also an embodiment of the fifth embodiment, the arteriosclerosis is triggered by formation of arteriosclerotic plaques mediated by HMGA1, HMGA1a, HMG1b and/or HMGA2.

In a ninth embodiment of the fourth aspect, which is also an embodiment of the first, second, third, fourth, fifth, sixth and seventh embodiment, the intracellular target molecule is present intracellularly.

According to a fifth aspect of the invention the object is achieved by a composition comprising a L-nucleic acid binding to an intracellular target molecule, and a delivery vehicle.

In a first embodiment of the fifth aspect the delivery vehicle is a delivery vehicle suitable for the intracellular delivery of the L-nucleic acid.

In a second embodiment of the fifth aspect, which is also an embodiment of the first embodiment, the delivery vehicle is selected from the group comprising vehicles, conjugates and physical means.

In a third embodiment of the fifth aspect, which is also an embodiment of the second embodiment, the delivery vehicle is a vehicle selected from the group comprising liposomes, nanoparticles, microparticles, cyclodextrins or dendrimers, or a vesicle consisting of polypeptides, polyethyleneimine and/or amphipathic molecules.

In a fourth embodiment of the fifth aspect, which is also an embodiment of the second embodiment, the delivery vehicle is a conjugate, wherein the conjugate is a conjugate for the receptor-mediated endocytosis, a conjugate with a fusogenic peptide, a conjugate with a signal peptide, a conjugate with a nucleic acid, preferably a conjugate with a spiegelmer, or a lipophilic conjugate.

In a fifth embodiment of the fifth aspect, which is also an embodiment of the second embodiment, the delivery vehicle is a physical means, the physical means preferably being selected from the group comprising electroporation, iontophoresis, pressure, ultrasound and shock waves.

In a sixth embodiment of the fifth aspect, which is also an embodiment of the third embodiment, the delivery vehicle comprises polyethyleneimine.

In a seventh embodiment of the fifth aspect, which is also an embodiment of the sixth embodiment, the polyethyleneimine is a branched polyethyleneimine with a molecular weight of about 25 kDa.

In an eighth embodiment of the fifth aspect, which is also an embodiment of the sixth and seventh embodiment, the polyethyleneimine forms a micelle or a micelle-like structure.

In a ninth embodiment of the fifth aspect, which is also an embodiment of the first, second, third, fourth, fifth, sixth, seventh and eighth embodiment, the L-nucleic acid is a spiegelmer.

In a tenth embodiment of the fifth aspect, which is also an embodiment of the ninth embodiment, the spiegelmer carries a modification, the said modification being selected from the group comprising PEG residues.

In an eleventh embodiment of the fifth aspect, which is also an embodiment of the tenth embodiment, the PEG residue has a molecular weight of about 1,000 to 10,000 Da, preferably a molecular weight of about 1,500 to 2,500 Da and most preferably a molecular weight of about 2,000 Da.

In a twelfth embodiment of the fifth aspect, which is also an embodiment of the tenth and eleventh embodiment, the modification is bound to the 5' terminus or to the 3' terminus of the L-nucleic acid.

In a thirteenth embodiment of the fifth aspect, which is also an embodiment of the ninth, tenth, eleventh and twelfth embodiment, in the composition the ratio of the total number of nitrogen groups of the polyethyleneimine to the total number of phosphate groups of the nucleic acid contained in the composition is about 1 to 20, preferably about 1.5 to 10, more preferably about 2 to 5 and most preferably about 2 to 3.

In a fourteenth embodiment of the fifth aspect, which is also an embodiment of the first, second, third, fourth, fifth, sixth, seventh, eighth, ninth, tenth, eleventh, twelfth and thirteenth embodiment, the composition provides the L-nucleic acid intracellularly.

According to a sixth aspect of the invention the object is achieved by the pharmaceutical composition comprising a composition according to the fifth aspect, and a pharmaceutically acceptable carrier.

In an embodiment of the use according to the first aspect the L-nucleic acid is a composition according to the fifth aspect.

In an embodiment of the method according to the second aspect the L-nucleic acid is a composition according to the fifth aspect.

In an embodiment of the use according to the third aspect the L-nucleic acid is a composition according to the fifth aspect.

In an embodiment of the use according to the fourth aspect the L-nucleic acid is a composition according to the fifth aspect.

According to a seventh aspect of the invention the object is achieved by an HMGA-binding nucleic acid, characterised in that the nucleic acid comprises a section Box A1 and a section Box A2, wherein the section Box A1 and the section Box A2 are joined to one another by an intermediate section and wherein Box A1 and Box A2 are selected individually and independently of one another from the group comprising GGGCG, GGGUG and GGGAG.

In a first embodiment of the seventh aspect the intermediate section consists either of an intermediate section Z1 comprising six or seven nucleotides, or of an intermediate section Z2 comprising 12 to 25 nucleotides.

In a second embodiment of the seventh aspect, which is also an embodiment of the first embodiment, the nucleic acid at the 5' end of the section Box A1 has a first section and at the 3' end of the section Box A2 has a second section, wherein preferably both sections independently of one another comprise four to eight nucleotides.

In a third embodiment of the seventh aspect, which is also an embodiment of the second embodiment, the two sections are at least partly or completely hybridised with one another, the hybridisation extending over four to eight nucleotide pairs.

In a fourth embodiment of the seventh aspect, which is also an embodiment of the second and third embodiments, the nucleic acid has at the 5' end of the section Box A1 a section Helix A1 and at the 3' end of the section Box A2 a section Helix A2, wherein preferably the section Helix A1 comprises four to eight nucleotides and preferably the section Helix A2 comprises four to eight nucleotides, and wherein preferably the section Helix A1 forms the first section at the 5' end of the section Box A1 or a part thereof, and wherein preferably the section Helix A2 forms the second section at the 3' end of the section Box A2 or a part thereof, the length of the section Helix A1 being independent of the length of the section Helix A2.

In a fifth embodiment of the seventh aspect, which is also an embodiment of the fourth embodiment, the sections Helix A1 and Helix A2 are at least partly or completely hybridised with one another, the hybridisation extending over four to eight nucleotide pairs.

In a sixth embodiment of the seventh aspect, which is also an embodiment of the fourth and fifth embodiment, between the 3' end of the section Helix A1 and the 5' end of the section Box A1 a section Helix B1 is arranged, and between the 3' end of the section Box A2 and the 5' end of the section Helix A2 a section Helix B2 is arranged, wherein preferably the length of the section Helix B1 and Helix B2 comprises in each case individually and independently a length of four to eight nucleotides.

In a seventh embodiment of the seventh aspect, which is also an embodiment of the sixth embodiment, the sections Helix B1 and Helix B2 are at least partly or completely hybridised with one another, the hybridisation extending over four to eight nucleotide pairs.

In an eighth embodiment of the seventh aspect, which is also an embodiment of the sixth and seventh embodiment, zero to five nucleotides are arranged between the 3' end of the section Helix A1 and the 5' end of the section Helix B1.

In a ninth embodiment of the seventh aspect, which is also an embodiment of the eighth embodiment, two nucleotides are arranged between the 3' end of the section Helix A1 and the 5' end of the section Helix B1.

In a tenth embodiment of the seventh aspect, which is also an embodiment of the sixth, seventh, eighth and ninth embodiment, zero to six nucleotides are arranged between the 3' end of the section Helix B2 and the 5' end of the section Helix A2.

In an eleventh embodiment of the seventh aspect, which is also an embodiment of the tenth embodiment, preferably insofar as this is an embodiment of the ninth embodiment, a nucleotide is arranged between the 3' end of the section Helix B2 and the 5' end of the section Helix A2.

In a twelfth embodiment of the seventh aspect, which is also an embodiment of the sixth, seventh, eighth, ninth, tenth and eleventh embodiment, the sum of the nucleotides of section Helix A1 and of section Helix B1 is ten to twelve nucleotides, and the sum of the nucleotides of section Helix A2 and of section Helix B2 is ten to twelve nucleotides.

In a thirteenth embodiment of the seventh aspect, which is also an embodiment of the twelfth embodiment, the sum of the hybridised nucleotides from the hybridisation of section Helix A1 with section Helix A2 and of section Helix B1 with section Helix B2 is ten to twelve nucleotide pairs.

In a fourteenth embodiment of the seventh aspect, which is also an embodiment of the sixth, seventh, eighth, ninth, tenth, eleventh, twelfth and thirteenth embodiment, preferably of the sixth or seventh embodiment, the nucleic acid does not comprise a section Helix A1 and Helix A2, whereby the section Helix B1 is arranged at the 5' end of the nucleic acid and the Helix B2 is arranged at the 3' end, wherein preferably the length of the section Helix B1 and Helix B2 comprises in each case individually and independently a length of four to eight nucleotides.

In a fifteenth embodiment of the seventh aspect, which is also an embodiment of the fourteenth embodiment, the sections Helix B1 and Helix B2 are at least partly or completely hybridised with one another, the hybridisation extending over four to eight nucleotide pairs.

In a sixteenth embodiment of the seventh aspect, which is an embodiment of the fourth and fifth embodiment, one to five nucleotides are arranged between the 3' end of the section Helix A1 and the 5' end of the section Box A1, and one to three nucleotides are arranged between the 3' end of the section Box A2 and the 5' end of the section Helix A2.

In a seventeenth embodiment of the seventh aspect, which is also an embodiment of the sixth, seventh, eighth, ninth, tenth, eleventh, twelfth, thirteenth, fourteenth and fifteenth embodiment, two nucleotides are arranged between the 3' end of the section Helix B1 and the 5' end of the section Box A1, and one to seven nucleotides are arranged between the 3' end of the section Box A2 and the 5' end of the section Helix B2.

In an eighteenth embodiment of the seventh aspect, which is also an embodiment of the first, second, third, fourth, fifth, sixth, seventh, eighth and tenth embodiment, insofar as this is an embodiment of the sixth, seventh and eighth embodiment, of the twelfth and thirteenth embodiment, insofar as these are embodiments of the sixth, seventh, eighth and tenth embodiments, of the fourteenth and fifteenth embodiment, insofar as these are embodiments of the sixth, seventh, eighth, tenth, twelfth and thirteenth embodiment, or of the seventeenth embodiment, insofar as these are embodiments of the sixth, eighth, tenth, twelfth, thirteenth and fifteenth embodiment, in each case in the herein restricted scope, the intermediate section Z1 comprises six or seven nucleotides.

In a nineteenth embodiment of the seventh aspect, which is also an embodiment of the eighteenth embodiment, the intermediate section Z1 comprises the sequence $N_1N_2GN_8N_3N_4N_5$, wherein
$N_1$=U, C, A or G;
$N_2$=G or U;
$N_3$=U or C;
$N_4$=U or A;
$N_5$=G or A; and
$N_8$=U or is absent.

In a twentieth embodiment of the seventh aspect, which is also an embodiment of the nineteenth embodiment, the nucleic acid comprises a section Box A1 and a section Box A2, wherein the 3' end of the section Box A1 is joined directly to the 5' end of the intermediate section Z1, and the 3' end of the intermediate section Z1 is joined directly to the 5' end of the section Box A2.

In a twenty-first embodiment of the seventh aspect, which is also an embodiment of the eighteenth, nineteenth and twentieth embodiment, in particular of the twentieth embodiment, the nucleic acid comprises a section Helix B1 and a section Helix B2.

In a twenty-second embodiment of the seventh aspect, which is also an embodiment of the twenty-first embodiment, the sections Helix B1 and Helix B2 comprise in each case individually and independently of one another four to eight nucleotides, which are preferably completely or partly hybridised with one another.

In a twenty-third embodiment of the seventh aspect, which is also an embodiment of the twenty-first and twenty-second embodiment, two nucleotides $N_6$, $N_7$ are arranged between the 3' end of the section Helix B1 and the 5' end of the section Box A1 in the 5' 3' direction, wherein $N_6$ is G, A or U, and $N_7$ is G or U.

In a twenty-fourth embodiment of the seventh aspect, which is also an embodiment of the twenty-first, twenty-second and twenty-third embodiment, there is no nucleotide between the 3' end of the section Box A2 and the 5' end of the section Helix B2, or the nucleotide sequence $GN_y$ is arranged in the 5' 3' direction, wherein $N_y$ comprises zero to six nucleotides, preferably 0 or 6 nucleotides.

In a twenty-fifth embodiment of the seventh aspect, which is also an embodiment of the eighteenth, nineteenth, twentieth, twenty-first, twenty-second, twenty-third and twenty-fourth embodiment, the nucleic acid comprises a section Helix A1 and Helix A2.

In a twenty-sixth embodiment of the seventh aspect, which is also an embodiment of the twenty-fifth embodiment, the sections Helix A1 and Helix A2 comprise in each case individually and independently of one another four to eight nucleotides, wherein preferably the sections Helix A1 and Helix A2 are completely or partly hybridised with one another.

In a twenty-seventh embodiment of the seventh aspect, which is also an embodiment of the twenty-fifth and twenty-sixth embodiment, a nucleotides sequence $N_X$ is arranged between the 3' end of the section Helix A1 and the 5' end of the section Helix B1, wherein $N_X$ comprises zero to five nucleotides.

In a twenty-eighth embodiment of the seventh aspect, which is also an embodiment of the twenty-fifth, twenty-sixth and twenty-seventh embodiment, a nucleotide sequence $N_z$ is arranged between the 3' end of the section Helix B2 and the 5' end of the section Helix A2, wherein $N_z$ comprises zero to six nucleotides.

In a twenty-ninth embodiment of the seventh aspect, which is also an embodiment of the twenty-first, twenty-second, twenty-third, twenty-fourth, twenty-fifth, twenty-sixth, twenty-seventh and twenty-eighth embodiment, the sum of the hybridised nucleotides from the hybridisation of section Helix A1 with section Helix A2 and of section Helix B1 with section Helix B2 is ten to twelve nucleotide pairs.

In a thirtieth embodiment of the seventh aspect, which is also an embodiment of the twenty-fourth, twenty-fifth, twenty-sixth, twenty-seventh, twenty-eighth and twenty-ninth embodiment, the nucleotide sequence $GN_y$ is arranged between the 3' end of the section Box A2 and the 5' end of the section Helix B2 in the 5'-3' direction, wherein $N_y$ comprises zero to six nucleotides, preferably 0 or 6 nucleotides.

In a thirty-first embodiment of the seventh aspect, which is also an embodiment of the thirtieth embodiment, the HMGA-binding nucleic acid comprises the following structure

wherein
$N_1$=U, C, A or G;
$N_2$=G or U;
$N_3$=U or C;
$N_4$=U or A;
$N_5$=G or A;
$N_6$=G, A or U;
$N_7$=G or U;
$N_8$=U or is no nucleotide;
$N_x$=zero to five nucleotides;
$N_y$=zero or six nucleotides; and
$N_z$=zero to six nucleotides;
the section Box A1 and section Box A2 are selected in each case individually and independently of one another from the group of nucleotide sequences comprising GGGCG, GGGUG and GGGAG;
the section Helix A1 and the section Helix A2 comprise in each case individually and independently of one another four to eight nucleotides, wherein preferably the sections Helix A1 and Helix A2 are completely or partly hybridised with one another, and
the sections Helix B1 and Helix B2 comprise in each case individually and independently of one another four to eight nucleotides, wherein preferably the sections Helix B1 and Helix B2 are completely or partly hybridised with one another and the hybridising region comprises four to eight nucleotides, and wherein the sum of the hybridised nucleotides from the hybridisation of section Helix A1 with section Helix A2 and of section Helix B1 with section Helix B2 is 10 to 12 nucleotide pairs.

In a thirty-second embodiment of the seventh aspect, which is also an embodiment of the thirtieth and thirty-first embodiment, the HMGA-binding nucleic acid comprises a sequence selected from the group comprising SEQ. ID. No. 1, SEQ. ID. No. 2, SEQ. ID. No. 3, SEQ. ID. No. 5, SEQ. ID. No. 6, SEQ. ID. No. 7 and SEQ. ID. No. 13.

In a thirty-third embodiment of the seventh aspect, which is also an embodiment of the twenty-fourth, twenty-fifth, twenty-sixth, twenty-seventh, twenty-eighth and twenty-ninth embodiment, the 3' end of the section Box A2 is joined directly to the 5' end of the section Helix B2.

In a thirty-fourth embodiment of the seventh aspect, which is also an embodiment of the thirty-third embodiment, the HMGA-binding nucleic acid has the following structure

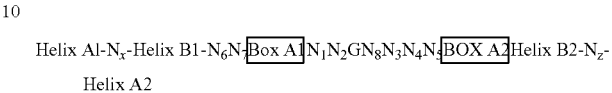

wherein
$N_1$=U, C, A or G;
$N_2$=G or U;
$N_3$=U or C;
$N_4$=U or A;
$N_5$=G or A;
$N_6$=G, A or U;
$N_7$=G or U;
$N_8$=U or is no nucleotide;
$N_x$=zero to five nucleotides; and
$N_z$=zero to six nucleotides;
the section Box A1 and Section Box A2 are selected in each case individually and independently of one another from the group of nucleotide sequences comprising GGGCG, GGGUG and GGGAG;
the section Helix A1 and the section Helix A2 comprise in each case individually and independently of one another four to eight nucleotides, wherein preferably the sections Helix A1 and Helix A2 are completely or partly hybridised with one another, and
the sections Helix B1 and Helix B2 comprise in each case individually and independently of one another four to eight nucleotides, wherein preferably the sections Helix B1 and Helix B2 are completely or partly hybridised with one another and the hybridising region comprises four to eight nucleotides, and wherein the sum of the hybridised nucleotides from the hybridisation of section Helix A1 with section Helix A2 and of section Helix B1 with section Helix B2 is 10 to 12 nucleotide pairs.

In a thirty-fifth embodiment of the seventh aspect, which is also an embodiment of the thirty-third and thirty-fourth embodiment, the HMGA-binding nucleic acid comprises a sequence including SEQ. ID. No. 3.

In a thirty-sixth embodiment of the seventh aspect, which is also an embodiment of the thirty-first embodiment, the HMGA-binding nucleic acid comprises the following structure

In a thirty-seventh embodiment of the seventh aspect, which is also an embodiment of the thirty-fourth embodiment, the HMGA-binding nucleic acid comprises the following structure

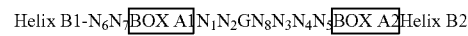

In a thirty-eighth embodiment of the seventh aspect, which is also an embodiment of the thirty-sixth embodiment, the HMGA-binding nucleic acid comprises a sequence which is selected from the group including SEQ. ID. No. 15 and SEQ. ID. No. 16.

In a thirty-ninth embodiment of the seventh aspect, which is also an embodiment of the first, second, third, fourth, fifth, sixth, seventh, eighth, ninth, tenth, eleventh, twelfth, thirteenth and sixteenth or seventeenth embodiment of the seventh aspect, the HMGA-binding nucleic acid comprises an intermediate section $Z_2$ which comprises 12 to 25 nucleotides.

In a fortieth embodiment of the seventh aspect, which is also an embodiment of the thirty-ninth embodiment, the HMGA-binding nucleic acid comprises an intermediate section Z2, a section Helix C1 and a section Helix C2.

In a forty-first embodiment of the seventh aspect, which is also an embodiment of the fortieth embodiment, a central section $N_c$ is arranged between the section Helix C1 and the section Helix C2 of the HMGA-binding nucleic acid.

In a forty-second embodiment of the seventh aspect, which is also an embodiment of the fortieth or forty-first embodiment, the length of the section Helix C1 and Helix C2 of the HMGA-binding nucleic acid are identical.

In a forty-third embodiment of the seventh aspect, which is also an embodiment of the fortieth, forty-first and forty-second embodiment, the length of the section Helix C1 and Helix C2 of the HMGA-binding nucleic acid is individually and independently three to six nucleotides.

In a forty-fourth embodiment of the seventh aspect, which is also an embodiment of the fortieth, forty-first, forty-second and forty-third embodiment, the sections Helix C1 and Helix C2 of the HMGA-binding nucleic acid are completely or party hybridised with one another.

In a forty-fifth embodiment of the seventh aspect, which is also an embodiment of the thirty-ninth, fortieth, forty-first, forty-second, forty-third and forty-fourth embodiment, the central section $N_c$ of the HMGA-binding nucleic acid comprises three to five nucleotides.

In a forty-sixth embodiment of the seventh aspect, which is also an embodiment of the thirty-ninth, fortieth, forty-first, forty-second, forty-third, forty-fourth and forty-fifth embodiment, the HMGA-binding nucleic acid comprises a section Box A1 and a section Box A2, wherein a nucleotide sequence $N_b$ is arranged between the 3' end of the section Box A1 and the 5' end of the section Helix C1 and comprises three nucleotides.

In a forty-seventh embodiment of the seventh aspect, which is also an embodiment of the thirty-ninth, fortieth, forty-first, forty-second, forty-third, forty-fourth, forty-fifth and forty-sixth embodiment, the HMGA-binding nucleic acid comprises a section Box A1 and a section Box A2, wherein a nucleotide sequence $N_d$ is arranged between the 3' end of the section Helix C2 and the 5' end of the section Box A2 and comprises two to five nucleotides.

In a forty-eighth embodiment of the seventh aspect, which is also an embodiment of the thirty-ninth, fortieth, forty-first, forty-second, forty-third, forty-fourth, forty-fifth, forty-sixth and forty-seventh embodiment, the HMGA-binding nucleic acid comprises a section Helix A1 and a section Helix A2.

In a forty-ninth embodiment of the seventh aspect, which is also an embodiment of the forty-eighth embodiment, the sections Helix A1 and Helix A2 of the HMGA-binding nucleic acid comprise in each case individually and independently of one another five to six nucleotides, wherein preferably the section Helix A1 and the section Helix A2 are completely or partly hybridised with one another.

In a fiftieth embodiment of the seventh aspect, which is also an embodiment of the forty-eighth and forty-ninth embodiment, a nucleotide sequence $N_a$ is arranged between the 3' end of the section Helix A1 and the 5' end of the section Box A1 of the HMGA-binding nucleic acid, wherein $N_a$ comprises one to five nucleotides.

In a fifty-first embodiment of the seventh aspect, which is also an embodiment of the forty-eighth, forty-ninth and fiftieth embodiment, a nucleotide sequence $GN_e$ is arranged between the 3' end of the section Box A2 and the 5' end of the section Helix A2 of the HMGA-binding nucleic acid in the 5'-3' direction, wherein $N_e$ comprises one to two nucleotides, preferably A or UU.

In a fifty-second embodiment of the seventh aspect, which is also an embodiment of the forty-eighth, forty-ninth, fiftieth and fifty-first embodiment, the section Helix C1 and the section Helix C2 of the HMGA-binding nucleic acid have in each case individually and independently of one another a length of five or six nucleotides, wherein preferably the sections Helix C1 and Helix C2 are completely or partly hybridised with one another.

In a fifty-third embodiment of the seventh aspect, which is also an embodiment of the fifty-second embodiment, the HMGA-binding nucleic acid has the following structure:

(III)

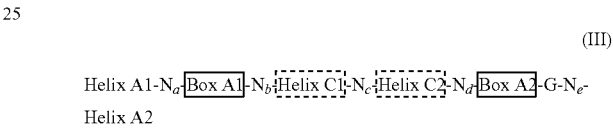

Helix A2 wherein
$N_a$=one to five nucleotides;
$N_b$=three nucleotides;
$N_c$=three to five nucleotides;
$N_d$=two to five nucleotides; and
$N_e$=one to two nucleotides, preferably A or UU;
the section Box A1 and the section Box A2 are selected in each case individually and independently of one another from the group comprising GGGCG, GGGUG and GGGAG,
the sections Helix A1 and Helix A2 comprise in each case individually and independently of one another five or six nucleotides, and
the sections Helix C1 and Helix C2 comprise in each case five or six nucleotides, which are preferably completely or partly hybridised with one another.

In a fifty-fourth embodiment of the seventh aspect, which is also an embodiment of the fifty-third embodiment, the HMGA-binding nucleic acid comprises a sequence which is selected from the group comprising SEQ. ID. No. 8, SEQ. ID. No. 9, SEQ. ID. No. 10, SEQ. ID. No. 11, SEQ. ID. No. 14, SEQ. ID. No. 22 and SEQ. ID. No. 24.

In a fifty-fifth embodiment of the seventh aspect, which is also an embodiment of the thirty-ninth, fortieth, forty-first, forty-second, forty-third and forty-fourth embodiment, the nucleic acid comprises a section Box 1 and a section Helix C1 of the HMGA-binding nucleic acid, wherein a nucleotide A is arranged between the 3' end of the section Box A1 and the 5' end of the section Helix C1.

In a fifty-sixth embodiment of the seventh aspect, which is also an embodiment of the fifty-fifth embodiment, the HMGA-binding nucleic acid comprises a section Helix C2 and a section Box A2, wherein a nucleotide G is arranged between the 3' end of the section Helix C2 and the 5' end of the section Box A2.

In a fifty-seventh embodiment of the seventh aspect, which is also an embodiment of the fifty-fifth or fifty-sixth embodiment, the central section $N_c$ of the HMGA-binding nucleic acid comprises four nucleotides, wherein $N_c$ is preferably GAUG.

In a fifty-eighth embodiment of the seventh aspect, which is also an embodiment of the fifty-fifth, fifty-sixth and fifty-seventh embodiment, the HMGA-binding nucleic acid comprises a section Helix B1 and a section Helix B2.

In a fifty-ninth embodiment of the seventh aspect, which is also an embodiment of the fifty-eighth embodiment, the sections Helix B1 and Helix B2 of the HMGA-binding nucleic acid comprise individually and independently of one another in each case five nucleotides, wherein preferably the section Helix B1 is hybridised with the section Helix B2.

In a sixtieth embodiment of the seventh aspect, which is also an embodiment of the fifty-eighth or fifty-ninth embodiment, a nucleotide sequence comprising two nucleotides $N_j$ is arranged between the 3' end of the section Helix B1 and the 5' end of the section Box A1 of the HMGA-binding nucleic acid, wherein $N_j$ is preferably AG.

In a sixty-first embodiment of the seventh aspect, which is also an embodiment of the fifty-eighth, fifty-ninth and sixtieth embodiment, a nucleotide G is arranged between the 3' end of the section Box A2 and the 5' end of Helix B2 of the HGMA-binding nucleic acid.

In a sixty-second embodiment of the seventh aspect, which is also an embodiment of the fifty-fifth, fifty-sixth, fifty-seventh, fifty-eighth, fifty-ninth, sixtieth and sixty-first embodiment, the HMGA-binding nucleic acid comprises a section Helix A1 and a section Helix A2.

In a sixty-third embodiment of the seventh aspect, which is also an embodiment of the sixty-second embodiment, the sections Helix A1 and Helix A2 of the HMGA-binding nucleic acid comprise individually and independently of one another in each case six nucleotides and preferably the section Helix A1 and the section Helix A2 are hybridised with one another.

In a sixty-fourth embodiment of the seventh aspect, which is also an embodiment of the sixty-second and sixty-third embodiment, a nucleotide sequence comprising two nucleotides $N_i$ is arranged between the 3' end of the section Helix A1 and the 5' end of the section Helix B1, wherein $N_i$ is preferably CA.

In a sixty-fifth embodiment of the seventh aspect, which is also an embodiment of the sixty-second, sixty-third and sixty-fourth embodiment, a nucleotide A is arranged between the 3' end of the section Helix B2 and the 5' end of the section Helix A2.

In a sixty-sixth embodiment of the seventh aspect, which is also an embodiment of the fifty-fifth to sixty-fifth embodiment, the sections Helix C1 and Helix C2 comprise in each case three nucleotides, wherein preferably the section Helix C1 and Helix C2 are hybridised with one another.

In a sixty-seventh embodiment of the seventh aspect, which is also an embodiment of the sixty-sixth embodiment, the HMGA-binding nucleic acid has the following structure:

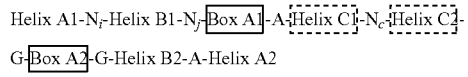

Helix A1-$N_i$-Helix B1-$N_j$-Box A1-A-Helix C1-$N_c$-Helix C2-G-Box A2-G-Helix B2-A-Helix A2 wherein
$N_i$=two nucleotides, preferably CA;
$N_j$=two nucleotides, preferably AG;
$N_c$=four nucleotides, preferably GAUG;

the sections Box A1 and Box A2 are in each case selected individually and independently of one another from the group comprising the sequences GGGCG, GGGUG and GGGAG;
the sections Helix A1 and Helix A2 comprise in each case individually and independently six nucleotides, which are preferably hybridised with one another;
the sections Helix B1 and Helix B2 comprise in each case individually and independently five nucleotides, wherein preferably the section Helix B1 and the section Helix B2 are hybridised with one another, and
the section Helix C1 and Helix C2 comprise in each case individually and independently three nucleotides, wherein preferably the sections Helix C1 and Helix C2 are hybridised with one another.

In a sixty-eighth embodiment of the seventh aspect, which is also an embodiment of the sixty-seventh embodiment, the HMGA-binding nucleic acid comprises a sequence which is selected from the group including SEQ. ID. No. 12.

In a sixty-ninth embodiment of the seventh aspect, which is also an embodiment of the second to sixty-seventh embodiment, the nucleic acid is one that binds to transcription factors, in particular transcription factors comprising an AT hook.

According to the invention the object is achieved in an eighth aspect by a nucleic acid, which binds to a transcription factor comprising an AT hook, wherein the nucleic acid has a structure according to the seventh aspect.

In an embodiment of the composition according to the sixth aspect the L-nucleic acid is a nucleic acid according to the seventh aspect.

In an embodiment of the use according to the first aspect the L-nucleic acid is a nucleic acid according to the seventh aspect.

In an embodiment of the method according to the second aspect the L-nucleic acid is a nucleic acid according to the seventh aspect.

In an embodiment of the use according to the third aspect the L-nucleic acid is a nucleic acid according to the seventh aspect.

In an embodiment of the method according to the fourth aspect the L-nucleic acid is a nucleic acid according to the seventh aspect.

According to the invention the object is achieved in a ninth aspect by a method for screening an HMGA antagonist or HMGA agonist, comprising the following steps:
providing a candidate HMGA antagonist and/or a candidate HMGA agonist,
providing a nucleic acid according to the seventh aspect,
providing a test system which delivers a signal in the presence of an HMGA antagonist and/or an HMGA agonist, and
determining whether the candidate HMGA antagonist is an HMGA antagonist and/or whether the candidate HMGA agonist is an HMGA agonist.

According to the invention the object is achieved in a tenth aspect by a method for screening an HMGA agonist and/or an HMGA antagonist, comprising the following steps:
providing an HMGA immobilised on a phase, preferably a solid phase,
providing a nucleic acid according to the seventh aspect, preferably a nucleic acid according to the seventh aspect which is labelled,
adding a candidate HMGA agonist and/or a candidate HMGA antagonist, and
determining whether the candidate HMGA agonist is an HMGA agonist and/or whether the candidate HMGA antagonist is an HMGA antagonist.

In an embodiment of the tenth aspect it is envisaged that the determination is carried out by testing whether the nucleic acid is replaced by the candidate HMGA agonist or by the candidate HMGA antagonist.

According to the invention the object is achieved in an eleventh aspect by a kit for the detection of HMGA, comprising a nucleic acid according to the seventh aspect.

According to the invention the object is achieved in a twelfth aspect by an HMGA antagonist which is obtainable by a method according to the tenth aspect.

According to the invention the object is achieved in a thirteenth aspect by an HMGA agonist which is obtainable by a method according to the tenth aspect.

According to the invention the object is achieved in a fourteenth aspect by a complex comprising an HMGA protein and a nucleic acid according to the seventh aspect.

The present invention is based on the surprising result that, contrary to the received opinion in the prior art, it is possible to use L-nucleic acids and in particular spiegelmers in order to address intracellular target molecules. The intracellular target molecules are preferably target molecules which are present in a cell. The properties inherent in the functional L-nucleic acids due to their structure of L-nucleotides, such as high specificity of the interaction with their target molecules with at the same time a high stability and absence of toxic or immunologically active decomposition products when the L-nucleic acids are used in biological systems and in particular in the animal and human body, does not however allow the cellular mechanisms to be utilised in order, as in the case of intramers, for L-nucleic acids to be coded by a plasmid or generally a vector and thus provide the actually functional nucleic acid by the intracellularly occurring process of transcription.

This inescapable dilemma is solved by the present invention: functional L-nucleic acids and in particular spiegelmers can be transported through a cytoplasmic membrane while retaining their specificity as regards their binding to their target molecule, and their activity. This permeability of the functional L-nucleic acids is inherent in spiegelmers and can be enhanced still further by the use of delivery vehicles or delivery techniques. Without hereinafter wishing to be specific in this matter, the present inventors start from the assumption that functional L-nucleic acids can per se overcome the cytoplasmic membrane, and with the participation of endosomal transport mechanisms in overcoming the cytoplasmic membrane, are able to free this from the vesicle structures that are thereby formed, with the adoption of a two-dimensional or three-dimensional structure, which allows the specific interaction of the functional nucleic acid with its target molecule. With the technical teaching disclosed herein, the principle developed for aptamers of utilising intracellular transcription mechanisms in order to create aptamers in the cell is intentionally avoided, and for the first time means are provided for using functional L-nucleic acids and in particular spiegelmers in cells.

As employed herein in a preferred embodiment, the term functional nucleic acids denotes those nucleic acids that are different from structural, in particular naturally occurring structural nucleic acids such as rRNAs or that are different from coding nucleic acids such as mRNAs. In particular functional nucleic acids are nucleic acids which, on account of their two-dimensional and/or three-dimensional structure, are able to bind to target molecules. In a particularly preferred embodiment the binding to the target molecule takes place not by hybridisation or base pairing on the basis of Watson-Crick base pairings or a Hoogsteen base pairing. Particularly preferred functional nucleic acids are aptamers and spiegelmers.

A L-nucleic acid is in a preferred embodiment a nucleic acid that is completely, substantially or partly synthesised from L-nucleotides. It is particularly preferred if the L-nucleic acid consists completely of L-nucleotides. The term "substantially" denotes in this connection an embodiment in which that part of the L-nucleic acid which is responsible for the interaction with the target molecule, or that part which mediates the binding to the target molecule, consist of L-nucleotides or is synthesised from these.

As used herein, a functional L-nucleic acid is a functional nucleic acid which is completely, substantially or partly synthesised from L-nucleotides.

The synthesis of L-nucleic acids is known to the person skilled in the art in this field and is described for example in Nolte et al., Nat. Biotech, 14, 1116-1119, 1996.; and Klussmann et al., Nat. Biotechnol, 14, 1112-1115, 1996.

The basic process for the production of aptamers is described for example in Tuerck et al. Science, 248, 505-510, 1990; or Ellington et al. Nature, 346, 818-822, 1990, while the basic process for the production of spiegelmers is described for example in Nolte et al., Nat. Biotech, 14, 1116-1119, 1996.; or Klussmann et al., Nat. Biotechnol, 14, 1112-1115, 1996. Spiegelmers are thus aptamers which consist of L-nucleotides instead of D-nucleotides. In connection with the production of aptamers and spiegelmers, the term target molecule denotes that molecule which is used in the selection process to produce aptamers and spiegelmers, or denotes that molecule which is ultimately bound by the aptamer or the spiegelmer.

In a preferred embodiment an intracellularly active agent is a chemical compound which when present in a cell is able to bind to a molecule. In this connection it is particularly preferred if the cell is a cell that exists isolated in a tissue or an organ, but preferably not in a human or animal body. If the intracellularly active agent is a spiegelmer, then preferably it is an intracellularly active agent if it is able to bind to an intracellular target molecule. Alternatively the spiegelmer is an intracellularly active agent if it is able to bind to its target molecule under conditions such as exist in a cell. Tests in order to determine these properties are known to the person skilled in the art in this field, and include for example equilibrium binding assays under buffer conditions such as exist intracellularly (ionic strength and solute composition, pH, temperature), as disclosed in Example 1.

In a preferred embodiment the target molecule of the L-nucleic acid, in particular of the functional L-nucleic acid, is an intracellular receptor. An intracellular receptor, as used herein, is preferably a chemical compound or a chemical structure or respectively a part thereof, with which the functional L-nucleic acid interacts, and is preferably a compound or structure to which the functional L-nucleic acid binds, wherein the intracellular receptor, i.e. the chemical compound or the chemical structure or respectively a part thereof, is present intracellularly, i.e. is present in a cell, as is preferably described in the preceding paragraph. In this connection it is possible within the scope of the present invention for the intracellular receptor to be the target molecule in the creation of the functional nucleic acid, in particular the functional L-nucleic acid.

In one embodiment the term "receptor" denotes any interaction partner, preferably a specifically binding interaction partner of the functional nucleic acid, i.e. denotes an interaction partner interacting with the functional nucleic acid, which has a specific spatial structure, charge distribution, hydrophobicity distribution, etc. In a particularly preferred embodiment the interaction partner corresponds to the target molecule of the functional nucleic acid, as was used in the creation of the functional nucleic acid. In this connection it is within the scope of the present invention that a receptor can also be different from the target molecule used in the creation of the functional nucleic acid, though the specific interaction is due to a cross reactivity of the functional nucleic acid between the interaction partner and the target molecule used in the creation of the functional nucleic acid.

In a preferred embodiment the term "intracellular receptor" denotes a receptor that is present in a cell, or a receptor that can be present in a cell, that occurs under natural circumstances in a cell, or that under such circumstances exist in a cell. In this connection it is particularly preferred if the cell is a cell that occurs isolated in a tissue or an organ, but preferably not in a human or animal body. As used herein, the term "intracellular receptor" however also denotes a receptor that is present under conditions such as exist in a cell.

In a preferred embodiment the term "cell" denotes a cell which is selected from the group comprising prokaryotic and eukaryotic cells. Preferably the eukaryotic cell is selected from the group comprising fungal cells, plant cells, animal cells and human cells. In an alternative embodiment the term cell generally denotes herein a compartment bounded by a phospholipid double membrane, which in a preferred embodiment corresponds to a cytoplasmic membrane, and which is separated by the membrane from the surroundings. The separation from the surroundings is in this connection not a complete separation, but allows an energy transfer and a mass transfer (substance exchange) between the cell and the surroundings. The mass transfer is preferably restricted. In the case where the cell is separated from the surroundings by a cytoplasmic membrane or by a membrane similar to a cytoplasmic membrane, the restriction of the mass transfer is defined by the transport properties of the membrane. In one embodiment the term cell herein thus also includes vesicles and/or compartments of a prokaryotic or eukaryotic cell as defined herein, which in turn are present or may be present both within a prokaryotic or eukaryotic cell, as well as outside such a prokaryotic or eukaryotic cell, for example as vesicles or parts of a prokaryotic or eukaryotic cell surrounded by a cytoplasmic membrane, which in one embodiment can be present in a body fluid. In a preferred embodiment, in a cell according to the second alternative embodiment it is envisaged that the conditions within such a cell correspond substantially to those occurring in a prokaryotic or eukaryotic cell, in particular as regards the factors which influence the binding of the functional nucleic acid to its target molecule.

In a preferred embodiment the body fluid is selected from the group comprising blood, urine, liquor (anatomical fluid), lymph fluid, serum, plasma, vaginal secretions, saliva and sperm.

In one embodiment the receptor is defined by its function in a cell. Accordingly the receptor can be selected from the group comprising molecular receptors, enzymes, metabolic intermediates, signal peptides, chaperone molecules and intracellular structures such as for example ribosomes, mitochondria, elements of the cytoskeleton such as for example tubulin and actin filaments, endosomal particles, lysosomes, other intracellular structures such as vesicles, in particular intracellular vesicles. As used herein the term molecular receptor denotes in a preferred embodiment a molecule which accepts information and transmits this within a cell, a tissue, an organ or an organism. The information is typically mediated by a molecule which interacts with the molecular receptor. As a result of the interaction the molecular receptor is able to generate a signal. Such a signal can be based on the change in the confirmation and/or of the activity of the receptor or can be manifested therein. The signal itself is able to transmit in another form the information received or processed by it. As a result of the change in the confirmation or activity of the molecular receptor, the signal can preferably be a chemical, biochemical or an electrical signal. Preferably the molecular receptor is part of a reaction cascade, and more preferably part of a signal cascade. The information transmitted by a molecular receptor can be quantitative and/or qualitative information, for example concerning the presence of a compound and/or its concentration.

In a preferred embodiment the term "metabolic intermediates" denotes all those compounds which, due to metabolic activities in a cell, occur as constituents of catabolism as well as of anabolism.

In a further embodiment the receptor is defined by its chemical nature. Preferably the receptor is selected from the group comprising polypeptides, carbohydrates, nucleic acids, lipids and combinations thereof. As used herein, the term polypeptide preferably denotes any polymer consisting of two or more amino acids. Preferably the amino acids are L-amino acids, though D-amino acids may also be used within the scope of the embodiment. As used herein the term "nucleic acids" preferably denotes a polymer of two or more nucleotides or nucleotide analogues which are known to the person skilled in the art in this field, wherein the nucleotides may be either D-nucleotides or L-nucleotides or mixtures thereof. Preferred combinations include glycosylated polypeptides and glycosylated lipids.

A particular group of intracellular receptors are transcription factors and DNA-binding proteins which bind to an AT hook. Examples of transcription factors are given in the following table 1:

TABLE 1

| Transcription factors | | |
|---|---|---|
| gamma)OBP | 14-3-3 epsilon | 70-75K protein |
| (STAT5A)4 | 14-3-3 zeta | 80-90K protein |
| 120-kDa CRE- | 50-55K protein | AAF |
| binding protein | 53BP1 | ABF-1 |
| ADA2 | AP-2alphaB | Bach1t |
| ADA3 | AP-2beta | Bach2 |
| ADA-NF1 | AP-2gamma | BAF155 |
| AFP1 | AP-2rep | BAF47 |
| AhR | AP-3 (1) | BAF53a |
| AhR: Arnt | AP-3 (2) | BAF60A |
| AIIN3 | AP-4 | Barhl1 |
| Aiolos | AP-5 | Barhl2 |
| AIRE | APC | Barx1 |
| AKNA | AR | Barx2 |
| ALF | Arnt | Bcl-3 |
| ALL-1 | Arnt (774 AA form) | BCL-6 |

TABLE 1-continued

| Transcription factors | | |
|---|---|---|
| alpha-CBF | ARNT2 | beta-catenin |
| alpha-CP2b | ASC-2 | Bin1 |
| alphaH0 | ASPP1 | BMAL2 |
| alphaH2-alphaH3 | ASPP2 | B-Myb |
| ALX3 | ATBF1-A | BNC |
| Alx-4 | ATBF1-B | BP1 |
| aMEF-2 | ATF | BP2 |
| AML1 | ATF-1 | BR140 |
| AML1a | ATF2 | Brachyury |
| AML1b | ATF-2 | BRCA1 |
| AML1c | ATF-2: c-Jun | BRCA2 |
| AML1DeltaN | ATF3 | BRG1 |
| AML2 | ATF3 deltaZIP | BRIP1 |
| AML3 | ATF4 | Brm |
| AML3a | ATF5 | BTEB1 |
| AML3b | ATF6 | BTEB2 |
| AMY-1L | ATF-a | BTEB3 |
| A-Myb | ATF-adelta | BTEB4 |
| ANF | ATOH1 | B-TFIID |
| AP-1 | ATPF1 | C/EBPalpha |
| AP-2alphaA | Bach1 | C/EBPbeta |
| C/EBPdelta | CIITA | CtBP2 |
| C/EBPepsilon | c-Jun | CTCF |
| C/EBPgamma | c-Jun: JunD | CTF |
| CA150 | CLIM1 | CTF-1 |
| c-abl | CLIM2 | CTF-2 |
| CACCC-binding factor | CLOCK | CTF-3 |
| CAR | c-Myb | CTF-5 |
| CAR: RXR-alpha | c-Myc | CTF-7 |
| Cart-1 | C-Myc 1 | CUP |
| CBAF | c-Myc: Max | CUTL1 |
| CBF (4) | CNBP | CUTL2 |
| CBF (5) | CoS | Cx |
| CBP | COUP-TF1 | cyclin A |
| CCAAT-binding factor | COUP-TF2 | cyclin T1 |
| | CP1A | cyclin T2 |
| CCF | CP1C | cyclin T2a |
| CCG1 | CP2 | cyclin T2b |
| CCK-1a | CPBP | DAP |
| CCK-1b | CPE binding protein | DAX1 |
| CD28RC | CREB | DB1 |
| Cdc5 | CRE-BPa | DBF4 |
| cdk2 | c-Rel | DBP |
| cdk9 | c-Rel: RelA | DbpA |
| Cdx-1 | CREMalpha | DbpAv |
| CDX2 | CREST | DbpB |
| Cdx-4 | CRF | DCoHm |
| c-Ets-1 | Crx | DDB |
| c-Ets-2 | CSA | DDB-1 |
| CFF | CSB | DDB-2 |
| c-Fos | CSBP-1 | DEC1 |
| ChCh | CSEN | DEC2 |
| CHOP-10 | c-Ski | DEF |
| Chx10 | CtBP1 | deltaCREB |
| deltaFosB | E2F | EllaE-Cbeta |
| deltaMax | E2F + E4 | EivF |
| DeltaN p63beta | E2F + p107 | EKLF |
| DeltaN p73alpha | E2F-1 | ELF-1 |
| DeltaN p73beta | E2F-1: DP-1 | ELFR |
| DeltaN p73gamma | E2F-1: DP-2 | elios |
| DeltaNp63alpha | E2F-2 | Elk-1 |
| DeltaNp63gamma | E2F-3a | Emx-1 |
| Dermo-1 | E2F-4 | Emx-2 |
| DF-1 | E2F-4: DP-1 | En-1 |
| DF-2 | E2F-4: DP-2 | En-2 |
| DF-3 | E2F-5 | ENH-binding protein |
| Dlx-1 | E2F-6 | ENKTF-1 |
| Dlx-2 | E2F-7 | EP400 |
| Dlx-3 | E47 | EPAS1 |
| Dlx-4 (long isoform) | E4BP4 | Epicardin |
| Dlx-4 (short isoform) | E4F | epsilonF1 |
| Dlx-5 | E4F1 | ER-alpha |
| Dlx-6 | E4TF2 | ER-alpha: ER-beta |
| DP-1 | E7; HPV-16, Papilloma Virus type 16 | ER-beta |
| DP-2 | | ER-beta1 |
| DPBF | EAR2 | ER-beta2 |
| DRIL1 | EBF | ER-beta3 |
| DSIF | EBP-80 | ER-beta4 |

TABLE 1-continued

| Transcription factors | | |
|---|---|---|
| DSIF-p14 | EC2 | ER-beta5 |
| DSIF-p160 | EF1 | ERF |
| DTF | Egr-1 | Erg-1 |
| DUX1 | Egr-2 | Erg-2 |
| DUX2 | Egr-3 | ERM |
| DUX3 | Egr-4 | ERR1 |
| DUX4 | EIIaE-A | ERR2 |
| E | EIIaE-B | ERR3 |
| E12 | EIIaE-Calpha | ERR3-1 |
| ERR3-2 | FOXB1 | FOXO1a |
| ERR3-3 | FOXC1 | FOXO1b |
| ERRalpha1 | FOXC2 | FOXO2 |
| ESE-1 | FOXD1 | FOXO3a |
| ESE-1a | FOXD2 | FOXO3b |
| ESE-1b | FOXD3 | FOXO4 |
| ESE-2 | FOXD4 | FOXP1 |
| ESE-2a | FOXE1 | FOXP2 |
| ESE-2b | FOXE3 | FOXP3 |
| ESE-3 | FOXF1 | FOXP4 |
| ESE-3a | FOXF2 | Fra-1 |
| ESE-3b | FOXG1a | Fra-2 |
| ESXR1 | FOXG1b | FTF |
| ETF | FOXG1c | FTS |
| Ets-1 deltaVII | FOXH1 | FXR |
| Evi-1 | FOXI1 | FXR: RXR-alpha |
| EVX1 | FOXJ1a | FXR-alpha |
| EZF-2 | FOXJ1b | FXR-beta1 |
| EZH1 | FOXJ2 (long isoform) | FXR-beta2 |
| EZH2 | FOXJ2 (short isoform) | G factor |
| F2F | FOXJ3 | G6 factor |
| FAC1 | FOXK1 | GAAP-1 |
| factor 2 | FOXK2a | GABP |
| FBP | FOXK2b | GABP-alpha |
| f-EBP | FOXK2c | GABPB |
| FEV | FOXL1 | GABP-beta1 |
| Fgf3 | FOXL2 | GABP-beta2 |
| FKBP59 | FOXM1a | GAF |
| FKHL18 | FOXM1b | gammaCAAT |
| FKHRL1P2 | FOXM1c | gammaCAC1 |
| FKLF | FOXN1 | gammaCAC2 |
| Fli-1 | FOXN2 | GATA-1 |
| FosB | FOXN3 | GATA-2 |
| GATA-3 | HAF | HiNF-A |
| GATA-4 | HAND1 | HiNF-B |
| GATA-5 | HAND2 | HiNF-C |
| GATA-6 | HB9 | HiNF-D |
| Gbx1 | HDAC1 | HiNF-D3 |
| Gbx2 | HDAC2 | HiNF-E |
| GCF | HDAC3 | HiNF-P |
| GCMa | HDAC4 | HIP1 |
| GCN5 | HDAC5 | HIV-EP2 |
| GCNF-1 | hDaxx | Hlf |
| GCNF-2 | HDBP1 | HLTF |
| GF1 | HDBP2 | HLTF (Met123) |
| GKLF | Heat-inducing factor | HLX |
| GLI1 | HEB | HMBP |
| GLI2 | HEB1-p67 | HMG I |
| GLI3 | HEB1-p94 | HMG I(Y) |
| GLIS2 | HEF-1B | HMG Y |
| GMEB-1 | HEF-1T | HMGB1 |
| GR | HEF-4C | HMGB2 |
| GR-alpha | HEN1 | HMGI-C |
| GR-beta | HEN2 | HMX1 |
| GRF-1 | HES-1 | HNF-1alpha-A |
| Gsc | HES-2 | HNF-1alpha-B |
| Gscl | Hesx1 | HNF-1alpha-C |
| GT-IC | Hex | HNF-1beta-A |
| GT-IIA | Hey1 | HNF-1beta-B |
| GT-IIBalpha | Hey2 | HNF-1beta-C |
| GT-IIBbeta | HeyL | HNF-3 |
| H1TF1 | HFH-1 | HNF-3alpha |
| H1TF2 | HIC-1 | HNF-3beta |
| H1TF2A | Hic-5 | HNF-3gamma |
| H4TF-1 | HIF-1 | HNF-4 |
| H4TF-2 | HIF-1 alpha | HNF-4alpha |
| HNF-4alpha1 | HOXC11 | IB1 |
| HNF-4alpha2 | HOXC12 | IBP-1 |
| HNF-4alpha3 | HOXC13 | ICER-II |

TABLE 1-continued

| Transcription factors | | |
|---|---|---|
| HNF-4alpha4 | HOXC4 | ICER-IIgamma |
| HNF-4alpha7 | HOXC5 | Id1 |
| HNF-4gamma | HOXC6 | Id1H |
| HNF-6alpha | HOXC8 | Id2 |
| hnRNP K | HOXC9 | Id3 |
| HOX11 | HOXD10 | Id3/Heir-1 |
| HOXA1 | HOXD11 | IF1 |
| HOXA10 | HOXD12 | IFI-16 |
| HOXA10 PL2 | HOXD13 | IgPE-1 |
| HOXA11 | HOXD3 | IgPE-2 |
| HOXA13 | HOXD4 | IgPE-3 |
| HOXA2 | HOXD8 | Ik-1 |
| HOXA3 | HOXD9 | IkappaB |
| HOXA4 | Hp55 | IkappaB-alpha |
| HOXA5 | Hp65 | IkappaB-beta |
| HOXA6 | HPX42B | IkappaBR |
| HOXA7 | HrpF | Il-1 RF |
| HOXA9A | HSBP1 | IL-10E1 |
| HOXA9B | HSF | IL-6 RE-BP |
| HOXB1 | HSF1 (long) | Il-6 RF |
| HOXB13 | HSF1 (short) | ING1 |
| HOXB2 | HSF2 | ING1b |
| HOXB3 | HSF4a | INSAF |
| HOXB4 | HSF4b | IPCS-BF |
| HOXB5 | HSF4c | IPF1 |
| HOXB6 | hsp56 | IPF1: Pbx |
| HOXB7 | Hsp90 | IRF-1 |
| HOXB8 | IA-1 | IRF-1: C/EBPbeta |
| HOXB9 | iASPP | IRF-2 |
| HOXC10 | iASPP-RAI | IRF-3 |
| IRF-4 | KR3 | Lmo1 |
| IRF-5 | KRF-1 | Lmo2 |
| IRF-6 | KRN | LMO3 |
| IRF-7A | KSR-1 | LMX1A |
| IRF-7B | Ku autoantigen | LMX1B |
| IRF-7H | Ku70 | L-Myc-1(long form) |
| IRF-8 | Ku80 | L-Myc-1 (short form) |
| IRF-9 | KUP | L-Myc-2 |
| irlB | LAF-4 | LUN-1 |
| IRX-1 | LANA; KSHV, Kaposi's sarcoma-associated herpes virus (herpes virus 8) | LUN-2 |
| IRX2a | | LXR-alpha |
| Irx-3 | | LXR-alpha: RXR-alpha |
| Irx-4 | | LXR-beta |
| ISGF-1 | LBP-1 | LXR-beta: RXR-alpha |
| ISGF-3 | LBP-1a | Lyl-1 |
| ISGF-3alpha | LBP-1d | M factor |
| Isl-1alpha | LBP-32 | Mad1 |
| ITF | LBP-9 | Maf |
| ITF-1 | LBX1 | MafB |
| ITF-2 | LCR-F1 | MafF |
| JRF | LEF-1 | MafG |
| JunB | LEF-1B | MafG: MafG |
| JunB: Fra-1 | LF-A1 | MafK |
| JunB: Fra-2 | LHX1 | MAML1 |
| JunD | LHX2 | MASH-1 |
| JunD: Fra-2 | LHX3a | Max |
| kappaY FaKtor | LHX3b | Max1 |
| KBP-1 | LHX5 | Max2 |
| KER1 | LHX6.1a | MAZ |
| KER-1 | LHX6.1b | MAZi |
| KLF15 | LIT-1 | MAZR |
| KLF7 | LITAF | MBF1 |
| Kox1 | LKLF | MBF2 |
| MBF3 | Miz-1 | NERF-2 |
| MBP-1 (1) | MLX | Net |
| MBP-1 (2) | MM-1 | NeuroD1 |
| MBP-2 | MondoA | NEUROD-2 |
| MDBP | MOP3 | NEUROD-3 |
| MECP-2 | MR | NF III-a |
| MEF-2A | MRF-2 | NF III-c |
| MEF-2B1 | Msx-1 | NF III-e |
| MEF-2C | Msx-2 | NF-1 |
| MEF-2C/delta32 | MTA1-L1 | NF-4FA |
| MEF-2C/delta8 | MTB-Zf | NF-4FB |
| MEF-2C/delta8,32 | MTF-1 | NF-4FC |
| MEF-2D00 | mtTFA | NF-AB |
| MEF-2D0B | Mxi1 | NF-AT1 |
| MEF-2DA0 | Myf-3 | NF-AT1 |

TABLE 1-continued

| Transcription factors | | |
|---|---|---|
| MEF-2DA'0 | Myf-4 | NF-AT2 |
| MEF-2DAB | Myf-5 | NF-AT2-alpha |
| MEF-2DA'B | Myf-6 | NF-AT2-beta |
| Meis-1 | Myocardin, Splice Form | NF-AT3 |
| Meis-2a | 1 | NF-AT4 |
| Meis-2b | MyoD | NF-AT5 |
| Meis-2c | MyoD: E12 | NfbetaA |
| Meis-2d | MyT1 | NF-CLE0a |
| Meis-2e | MZF-1 | NF-CLE0b |
| Meis-3 | NC1 | NFdeltaE3A |
| Mel-18 | NC2 | NFdeltaE3B |
| Meox1 | NCOR1 | NFdeltaE3C |
| Meox1a | NCOR2 | NFdeltaE4A |
| Meox2 | NCX | NFdeltaE4B |
| MHox (K-2) | NELF | NFdeltaE4C |
| MIF-1 | NERF | Nfe |
| MITF | NERF-1a | NF-E |
| MIXL1 | NERF-1b | NF-E2 |
| NF-E2 p45 | NF-Y | NRF |
| NF-E3 | NF-YA | Nrf1 |
| NFE-6 | NF-Zc | NRF-1 |
| NF-Gma | NF-Zz | Nrf1: MafG |
| NF-GMb | NGN3 | Nrf1: MafK |
| NFI/CTF | NHP-1 | Nrf2 |
| NFIA | NHP-2 | Nrf2: MafG |
| NFIB | NHP3 | Nrf2: MafK |
| NF-IL-2° | NHP4 | NRF-2beta1 |
| NF-IL-2B | Nkx2-1 | NRF-2gamma1 |
| NFIX | Nkx2-2 | Nrf3 |
| NF-jun | Nkx2-3 | Nrf3: MafK |
| NF-kappaB | Nkx2-5 | NRL |
| NF-kappaB(-similar) | Nkx2-8 | NRSF |
| NF-kappaB1 | Nkx3-1 | NRSF Form 1 |
| NF-kappaB1 precursor | Nkx3-1 v1 | NRSF Form 2 |
| NF-kappaB2 | Nkx3-1 v2 | NTF |
| NF-kappaB2 (p49) | Nkx3-1 v3 | Nur77 |
| NF-kappaB2 precursor | Nkx3-1 v4 | NURR1 |
| NF-kappaE1 | Nkx3-2 | OAZ |
| NF-kappaE2 | Nkx6-1 | OC-2 |
| NF-kappaE3 | Nkx6-2 | OCA-B |
| NF-MHCIIA | Nmi | Octa factor |
| NF-MHCIIB | N-Myc | Octamer |
| NF-muE1 | N-Oct-2alpha | binding factor |
| NF-muE2 | N-Oct-2beta | Oct-B1 |
| NF-muE3 | N-Oct-4 | oct-B2 |
| NF-S | NOR1 | oct-B3 |
| NF-X | NOR1/MINOR | OLIG2 |
| NF-X1 | NPA3 | Oligo1 |
| NF-X2 | NPAS1 | Otx1 |
| NF-X3 | NPAS2 | Otx2 |
| NF-Xc | NP-TCII | Otx3 |
| OZF | Pax-3 | Pbx1A: HoxD4 |
| p107 | Pax-3A | Pbx1a: IPF1 |
| p130 | Pax-3B | Pbx1b |
| p160MBP | Pax-4a | Pbx1B: HoxA5 |
| p28 Modulator | Pax-5 | Pbx1B: HoxB7 |
| p300 | Pax-6 | Pbx1B: HoxB8 |
| p38erg | Pax-6/Pd-5a | Pbx1B: HoxC8 |
| p40x; HTLV-I, T-cell | Pax-7 | Pbx1B: HoxD4 |
| Lymphotropic virus | Pax-8 | Pbx1b: PKNOX1 |
| type I | Pax-8a | Pbx2 |
| p45 | Pax-8b | Pbx2: HoxB8 |
| p49erg | Pax-8c | Pbx2: Hoxc6 |
| p50: c-Rel | Pax-8d | Pbx2: PKNOX1 |
| p53 | Pax-8e | Pbx3a |
| p55 | Pax-8f | Pbx3a: Hoxc6 |
| p55erg | Pax-9 | Pbx3b |
| p63 | Pbx | PC2 |
| p63alpha | Pbx1 | PC4 |
| p63beta | Pbx1: HoxB1 | PC5 |
| p63delta | Pbx1: HoxB2 | PCAF |
| p63gamma | Pbx1: HoxB3 | PDEF |
| p65delta | Pbx1: HoxB4 | PEA3 |
| p73 | Pbx1: HoxB5 | PEBP2alpha |
| p73alpha | Pbx1: HoxB6 | PEBP2beta |
| p73beta | Pbx1: HoxB8 | PGC-1 |
| p73delta | Pbx1: PKNOX1 | PITX1 |
| p73epsilon | Pbx1: Tcl3 | PITX2 |

TABLE 1-continued

| Transcription factors | | |
|---|---|---|
| p73eta | Pbx1a | PITX2A |
| p73gamma | Pbx1A: HoxA5 | PITX2A: Nkx2.5 |
| p73kappa | Pbx1a: Hoxb7 | PITX2B |
| p73zeta | Pbx1a: Hoxb8 | PITX2B: Nkx2.5 |
| Pax-1 | Pbx1a: Hoxc6 | PITX2C |
| Pax-2 | Pbx1A: HoxC8 | PITX2C: Nkx2.5 |
| PITX3 | POU5F1 | PU.1 |
| PKNOX1 | POU5F1A | PuF |
| PKNOX2 | POU5F1B | Pur factor |
| PLAGL1 | POU5F1C | pX; HBV, Hepatitis B |
| PLAGL2 | POU6F1 | Virus |
| PLZF | PPAR-alpha | PXR-1 |
| PML | PPAR-alpha: RXR- | PXR-1: RXR-alpha |
| PML-3 | alpha | PXR-1: RXR-beta |
| Pmx2a | PPAR-beta | PXR-2 |
| Pmx2b | PPAR-gamma1 | R1 |
| PNR | PPAR-gamma2 | R2 |
| PO-B | PPAR-gamma3 | RAR-alpha |
| Pontin52 | PPAR-gamma4 | RAR-alpha: RXR-alpha |
| POU1F1 | PPUR | RAR-alpha: RXR-beta |
| POU2F1 | PR | RAR-alpha: RXR- |
| POU2F2 | PR A | gamma |
| POU2F2 (Oct-2.1) | PR B | RAR-alpha1 |
| POU2F2B | pRb | RAR-alpha2 |
| POU2F2C | PRDI-BF1 | RAR-beta |
| POU2F3 | PRDI-BFc | RAR-beta: RXR-alpha |
| POU2F3, Isoform a | Preb | RAR-beta2 |
| POU2F3, Isoform d1 | Prop-1 | RAR-gamma |
| POU2F3, Isoform d2 | PROX1 | RAR-gamma: RXR- |
| POU3F1 | PSE1 | alpha |
| POU3F2 | P-TEFb | RAR-gamma1 |
| POU3F2 (N-Oct-5a) | PTF | Rb: E2F-1: DP-1 |
| POU3F2 (N-Oct-5b) | PTFalpha | RBP60 |
| POU3F3 | PTFbeta | RBP-Jkappa |
| POU3F4 | PTFdelta | Ref-1 |
| POU4F1(l) | PTFgamma | RelA |
| POU4F1(s) | Pu box binding factor | RelB |
| POU4F2 | Pu box binding factor | REVERB-alpha |
| POU4F3 | (BJA-B) | REVERB-beta |
| RFX1 | SHOX2b | Smad7 |
| RFX1: RFX2 | SHOXa | Smad8 |
| RFX1: RFX3 | SHOXb | SMIF |
| RFX2 | SHP | Sna |
| RFX3 | SIII-p110 | SnoN |
| RFX4 | SIII-p15 | Sox1 |
| RFX5 | SIII-p18 | Sox10 |
| RFX5: RFXAP: RFXANK | SIM1 | Sox11 |
| RFXANK | SIM2 | Sox12 |
| RFXAP | SIP1 | Sox13 |
| RFX-B-delta5 | Six-1 | Sox14 |
| RF-Y | Six-2 | Sox17 |
| RORalpha1 | Six-3 | Sox18 |
| RORalpha2 | Six-4 | Sox2 |
| RORalpha3 | Six-5 | Sox20 |
| RORbeta | Six-6 | Sox21 |
| RORgamma | SKIP | Sox3 |
| Rox | SLUG | Sox4 |
| RP58 | Smad1 | Sox5 |
| RPF1 | Smad2 | Sox7 |
| RPGalpha | Smad2 (437 | Sox8 |
| RREB-1 | amino acids) | Sox9 |
| RSRFC4 | Smad3 | Sp1 |
| RSRFC9 | Smad3: Smad4 | Sp2 |
| RVF | Smad4 | Sp3 |
| RX | Smad4delta3 | Sp4 |
| RXR-alpha | Smad4delta4 | Spi-B |
| RXR-beta | Smad4delta4-6 | SPT16 |
| RXR-gamma | Smad4delta4-7 | SRC-1 |
| SAP-1a | Smad4delta5-6 | SRC-3 |
| SAP-1b | Smad4delta6 | SRCAP |
| SF-1 | Smad5 | SREBP-1a |
| SHOX2a | Smad6 | SREBP-1b |
| SREBP-1c | TAF(II)100 | TBX19 |
| SREBP-2 | TAF(II)125 | TBX1A |
| SRE-ZBP | TAF(II)135 | TBX1B |
| SRF | TAF(II)170 | TBX2 |
| SRF: SRF | TAF(II)18 | TBX20 |
| SRY | TAF(II)20 | Tbx22 |

TABLE 1-continued

| Transcription factors | | |
|---|---|---|
| SSRP1 | TAF(II)250 | TBX3 (722 amino acids) |
| Staf-50 | TAF(II)250Delta | TBX3 (742 amino acids) |
| STAT1 | TAF(II)28 | |
| STAT1: STAT1 | TAF(II)30 | TBX4 |
| STAT1: STAT3 | TAF(II)31 | TBX5 (long isoform) |
| STAT1 alpha | TAF(II)55 | TBX5 (short isoform) |
| STAT1beta | TAF(II)70-alpha | Tbx5: Nkx2.5 |
| STAT2 | TAF(II)70-beta | TBX6 |
| STAT3 | TAF(II)70-gamma | TCF |
| STAT3: STAT3 | TAF-I | TCF-1 |
| STAT4 | TAF-II | TCF17 |
| STAT5A | TAF-L | TCF-1A |
| STAT5B | Tal-1 | TCF-1B |
| STAT5B: STAT5B | Tal-1beta | TCF-1C |
| STAT6 | Tal-2 | TCF-1D |
| SXR | TAR factor | TCF-1E |
| SXR: RXR-alpha | tat; HIV-1, Immunodeficiency virus type 1 | TCF-1F |
| SYT | | TCF-1G |
| TSR-alpha: | | TCF-2alpha |
| T3R-alpha: RXR-alpha | Tax; HTLV-I, T-cell Lymphotropic virus type I | TCF-3 |
| T3R-alpha1 | | TCF-4 |
| T3R-alpha2 | | TCF-4(K) |
| T3R-beta1 | T-bet | TCF-4B |
| T3R-beta2 | TBP | TCF-4E |
| TAF(I)110 | Tbr-1 | TEF |
| TAF(I)48 | TBR2 | TEF-1 |
| TAF(I)63 | TBX18 | TRF (2) |
| TEF-2 | TFIIH-MO15 | TRRAP |
| TEF-3 | TFIIH-p34 | TWIST |
| TEF-5 | TFIIH-p44 | TxRE BP |
| TEL1 | TFIIH-p62 | TxREF |
| Tel-2a | TFIIH-p80 | UBF |
| Tel-2b | TFIIH-p80: CAK | UBP-1 |
| Tel-2c | TFIIH-p90 | UEF-1 |
| Tel-2d | TFII-I | UEF-2 |
| Tel-2e | TFIIIA | UEF-3 |
| Tel-2f | Tf-LF1 | UEF-4 |
| TFE3 | Tf-LF2 | USF1 |
| TFEB | TFP-95 | USF1: USF2 |
| TFEB-A | TGIF | USF2 |
| TFEC | TGIF2 | USF2b |
| TFIIA | TGT3 | Vav |
| TFIIA-alpha/beta precursor (main form) | TIEG-1 | Vax-2 |
| | TIF1a | VDR |
| TFIIA-alpha/beta precursor (subsidiary form) | TIF1g | VITF; Vaccinia virus/, Homo sapiens |
| | TIF2 | |
| TFIIA-gamma | TLE1 | |
| TFIIB | TLX | Vpr; HIV-1, Immunodeficiency virus type 1 |
| TFIID | TLX3 | |
| TFIIE | TMF | |
| TFIIE-alpha | TR2-11 | WBSCR14 |
| TFIIE-beta | TR2-5 | WSTF |
| TFIIF | TR2-9 | WT1 |
| TFIIF-alpha | TR4 | WT1 I |
| TFIIF-beta | TRAP | WT1 I -KTS |
| TFIIH | TREB-1 | WT1 I-del2 |
| TFIIH* | TREB-2 | WT1 -KTS |
| TFIIH-CAK | TREB-3 | WT1-del2 |
| TFIIH-cyclin H | TREF1 | XBP-1 |
| TFIIH-MAT1 | TREF2 | XW, V |
| YAF2 | ZF1 | ZNF174 |
| YB-1 | ZF2 | ZNF-20 |
| YEBP | ZFP-37 | ZNF-24 |
| YL-1 | ZFX | ZNF33a |
| YY1 | ZFY | ZNF35 |
| ZAC | ZHX1 | ZNF43 |
| ZBP89 | ZIC2 | ZNF44 |
| ZBP99 | ZID | ZNF45 |
| ZEB (1124 AA) | ZNF11a | ZNF7 |
| ZEB (1154 AA) | ZNF124 | ZNF76 |
| ZER6 p52 | ZNF133 | ZNF83 |
| ZER6 p71 | ZNF143 | ZNF85 |

A further group of intracellular receptors are the intracellular target molecules listed in the following Table 2.

TABLE 2

| Intracellular target molecules | | |
|---|---|---|
| "long-chain" fatty acid CoA ligase | Acetyl-CoA malate-citrate synthase | Amyloid precursor protein Ankarin |
| "major basic" protein | Acetylglucosaminyl transferase | Arginase |
| "mixed function" oxygenase | Acetylspermine deacetylase | Argininosuccinate synthetase |
| 11β-hydroxylase (EC 1.14.15.4) | Acetyl transcylase | Argininosuccinate lyase |
| 18-hydroxylase | Aconitase | Aromatase |
| 1-acylglycerol-3-phosphate acyl transferase | Actin | Arylsulfatase |
| | Adenosine deaminase | Aspartate aminotransferase |
| 2,3-oxidosqualene lanosterol cyclase | Adenosyl homocysteine hydrolase | Aspartate transcarbamoylase |
| 21-steroid hydroxylase (EC 1.14.99.10) | Adenosyl methionine decarboxylase | ATPase ATP diphosphohydrolase |
| 24,28-sterol reductase | Adenylate cyclase | bcl-2 oncogene protein |
| 3-hydroxybutyrate dehydrogenase | Adenylate deaminase | Connective tissue-activating peptide |
| 3-ketothiolase | Adenylate kinase | C5a-inactivating factor |
| | Adenylo-succinate lyase | |
| | Adenylo-succinate synthase | |
| 3-β-hydroxysteroid dehydrogenase (EC5.3.3.1) | Alanine aminotransferase | Calcitonin |
| | Aldolase | Calmodulin |
| 5'-nucleotidase | Aldose reductase | Calpain I |
| 8-oxoguanosine deglycosylase | Alkaline phosphatase | Calreticulin |
| | Alcohol dehydrogenase | Carbamoyl phosphate synthetase |
| abl oncogene protein | Amidophosphoribosyl amine transferase | Carbonate anhydrase |
| Acetolactate synthase | AMP | Casein kinase 1 |
| Acetylcholine esterase | phosphodiestererase | Casein kinase 2 |
| Acetyl-CoA carboxylase | Amyloid β/A4 protein | Catalase |
| Catechol methyltransferase | Dihydrouracil dehydrogenase | Glycerol phosphate acyltransferase |
| Cathepsin | Dioxygenase | Glycerol phosphate dehydrogenase |
| Cathepsin B and L | Dopamine monooxygenase | |
| cdc 10 | Dynenin | Glycinamide ribonucleotide transformylase |
| cdc 13 p60 | Elastase | |
| cdc 2 p34 | Elastin | |
| cdc 25 p80 | Elongation factor Tu | GTP-binding protein |
| Chaparonin | Endo-rhamosidase | Haemoglobin A |
| Cholesterol esterase | Enolase | Haemoglobin A1 |
| Cholesterol mono-oxygenase | Enoyl-ACP-hydratase | Haemoglobin Barcelona |
| | Enoyl-ACP-reductase | Haemoglobin Barts |
| Citrate synthetase | ets oncogene protein | Haemoglobin Beth Israel |
| Clathrin | Ferritin | Haemoglobin Bunbury |
| Collagenase | Ferrodoxin | Haemoglobin Cochin-Port Royal |
| Cortisone dehydrogenase | Fatty acid synthetase | |
| crk oncogene protein | fgr oncogene protein | Haemoglobin Cowtown |
| Cyclin A and B | fps oncogene protein | Haemoglobin Cranston |
| Cyclophilin | Fructose bisphosphate aldolase | Haemoglobin Creteil |
| Cytidine deaminase | | Haemoglobin D |
| Cytidylate deaminase | Fumarase | Haemoglobin D Los Angeles |
| Cytochrome C peroxidase | GABA aminotransferase | |
| Cytochrome P450 | Galactosidase | Haemoglobin D Punjab |
| Cytosine methyltransferase | Gelatinase | Haemoglobin F |
| | Gelsolin | Haemoglobin Gower |
| dbl oncogene protein | Glucophosphate isomerase | Haemoglobin Hammersmith |
| Defensin | Glucosylceramide galactosyl transferase | |
| Diacyl glycerol acyltransferase | Glutaminase | Haemoglobin Hiroshima Haemoglobin Indianapolis |
| Dihydrofolate reductase | Glutamine phosphoribosyl pyrophosphate amidotransferase | Haemoglobin Kansas |
| Dihydroorotatase | | Haemoglobin Kariya |
| Dihydroorotate dehydrogenase | | Haemoglobin Kempsey Haemoglobin Kenya |
| Haemoglobin Lepore | Hydroxymethylglutaryl-CoA-reductase | Myeloperoxidase |
| Haemoglobin M | | Myofilament |
| Haemoglobin M Hyde Park | Hydroxymethylglutaryl-CoA-synthetase | myristoyl transferase Na/K ATPase |
| Haemoglobin M Iwate | Hydroxysteroid dehydrogenase | N-acetylglucuronidase |
| Haemoglobin M Saskatoon | | NAD-dependent sterol-4-carboxylase |
| Haemoglobin Nancy | Hypoxanthine-guanine-phosphoribosyl transferase | NADase |
| Haemoglobin Philly | | |
| Haemoglobin Quong Sze | IMP-dehydrogenase | NADPH-dependent 3-oxosteroid reductase |
| Haemoglobin Raleigh | Indole lyase | |
| Haemoglobin Ranier | Inositol phosphate phosphatase | Nexin |
| Haemoglobin S | | N-ras oncogene protein |

TABLE 2-continued

| Intracellular target molecules | | |
|---|---|---|
| Haemoglobin Sealy | int-1 oncogene protein | Nucleolus protein B23 |
| Haemoglobin Seattle | Isocitrate lyase | Nucleoside diphosphate |
| Haemoglobin St. Louis | Kinin-forming enzyme | kinase |
| Haemoglobin St. Mande | Ki-ras oncogene protein | Ornithine |
| Haemoglobin Titusville | Lactate dehydrogenase | aminotransferase |
| Haemoglobin Torino | Lactoferrin | Ornithine |
| Haemoglobin Wayne | Laminin | carbamoyltransferase |
| Haemoglobin York | Leukocyte elastase | Ornithine decarboxylase |
| Haemoglobin Zurich | Lipocortin | Orotate decarboxylase |
| Ha-ras oncogene protein | Lipoxygenase | Orotate |
| Hexokinase | L-myc oncogene protein | phosphoribosyl transferase |
| Histaminase | Lysozyme | p53 |
| Histidine decarboxylase | Malate dehydrogenase | Peptidyl amidoglycolate |
| HSP 27 | Malate synthase | lyase |
| Hydropyrimidine | Malonyl transacylase | Peptidyl prolyl isomerase |
| hydrolase | Mannosidase | PF4 |
| Hydroxyacyl-CoA- | met oncogene protein | Phenylalanine |
| dehydrogenase | Methaemoglobin | hydroxylase |
| Hydroxymethylglutaryl | Methionine | Phosphatidate phosphatase |
| CoA-splitting enzyme | adenosyl transferase | Phosphoenol pyruvate |
|  | mos oncogene protein | carboxykinase |
| Phosphofructokinase | rel oncogene protein | tRNA synthetase |
| Phosphoglucokinase | Ribonucleotide reductase | Tropomyosin |
| Phosphoglucomutase | Ribose phosphate- | Tryptophan synthase |
| Phosphoglycerate kinase | pyrophosphate kinase | Tubulin |
| Phosphoglyceromutase | Ricin tropoelastin | Tyrosine kinase |
| Phospholipase A2 | acid phosphatase | Ubioquinone reductase |
| Phospholipase C | acid protease | UPA |
| Phospholipase CG1 | Heavy meromyosin | Uridine monophosphate |
| Phospholipase D | serine/threonine kinase | kinase |
| Phospholipase S | Spectrin | Vitamin K reductase |
| Phosphoribomutase | Spermine synthase | wee-1 gene product |
| Phosphoribosyl phosphate | Squalene epoxidase | Xanthine dehydrogenase |
| transferase | Squalene monooxygenase | Xanthine oxidase |
| pim oncogene protein | src oncogene protein | Xylosyl transferase |
| Plasminogen activator- | Sterol methyltransferase | yes oncogene protein |
| inhibitor | suc 1 p13 | α-actin |
| Porin | Succinyl-CoA -synthetase | α-mannosidase |
| pRB (retinoblastoma gene | Superoxide dismutase | α-melogenin |
| product) | Tartrate dehydrogenase | α-tubulin |
| pRb retinablastoma gene | Thioesterase | β-actin |
| product | Thioredoxin | β-glucuronidase |
| Properdin | Thrombospondin | β-glycerophosphatase |
| Prostaglandin synthase | Thromboxane-A2- | β-ketoacyl-ACP- |
| Protein kinase C | synthetase | reductase |
| Purine nucleoside | Thymidylate synthetase | β-ketoacyl-ACP- |
| phosphorylase | Transacylase | synthetase |
| Pyruvate dehydrogenase | Triose phosphate isomerase | β-spectrin |
| Pyruvate kinase | Triose phosphate | β-tropomyosin |
| raf oncogene protein | dehyrogenase | β-tubulin |

A further particularly preferred group of intracellular receptors are the HMG proteins, such as are described for example in the International Patent Application PCT/EP96/00716, and in particular the HMGA proteins. As used herein the term HMGA proteins preferably denotes overall the following proteins: HMGA1, HMGA1a, HMGA1b and HMGA2.

The HMGA proteins have a modular structure and each comprise three DNA-binding domains, which are termed "AT hooks" and are shown as DBD1 to DBD3 in FIG. 2, as well as a very acidic C-terminal region. It is obvious to the person skilled in the art that antagonists which bind to one of the "AT hooks" recognise not only the HMGA1 proteins and thus the two splice variants HMGA1A and HMGA1B (see FIG. 2), but also exhibit cross reactivity with similar DNA-binding molecules such as HMGA2. Apart from HMGA2, many further proteins also have sequences similar to the "AT hooks" and form in each case further receptors. Such proteins are listed inter alia in Table 3:

TABLE 3

| Column 1: Protein data bank - Access codes; Column 2: Protein designation | |
|---|---|
| Q9UKB0 | Human HMG-Protein-R |
| Q9UKY1 | ZHX1_Human Zinc finger- and Homoeobox-Protein 1 |
| P55198 | AF17_HUMAN AF-17 Protein [MLLT6] |
| Q59F28 | Human Trithorax Homologon (Fragment) |
| Q6PJQ2 | Human ZNF406 Protein (Fragment) |
| Q75PJ9 | Human ZFAT-1 Protein |
| Q75PJ7 | Human ZFAT-3 Protein |
| Q75PJ6 | Human TR-ZFAT Protein |
| Q9ULG1 | Human KIAA1259 Protein |
| Q9NUK2 | Human Hypothetical Protein FLJ11314 |
| Q9NTG6 | Human Hypothetical Protein DKFZp434B0616 |
| Q8IX01 | SFR14_HUMAN Presumed Splice Factor |
| Q9H5J8 | Human Hypothetical Protein FLJ23363 |
| Q6I9Y6 | Human MGC5306 Protein |
| Q8IX01-2 | Splice Isoform 2 of Q8IX01 |
| Q8IX01-3 | Splice Isoform 3 of Q8IX01 |
| Q8IX01-4 | Splice Isoform 4 of Q8IX01 |
| Q15291 | RBBP5_HUMAN Retinoblastoma-binding Protein 5 (RBBP-5) |

TABLE 3-continued

Column 1: Protein data bank - Access codes; Column 2: Protein designation

| | |
|---|---|
| P51608 | MECP2_HUMAN Methyl-CpG-binding Protein 2 |
| Q6IPE2 | Human FLJ12800 Protein |
| Q6QHH9 | Human Methyl-CpG-binding Protein 2, Isoform B |
| Q9H8H4 | Human Hypothetical Protein FLJ13629 |
| Q7Z384 | Human Hypothetical Protein DKFZp686A24160 |
| O42043 | ENK7_HUMAN HERV-K_1q23.3 Provirus |
| P61569 | ENK16_HUMAN HERV-K_10p14 Provirus |
| Q86VM3 | Human MYB binding Protein 1a [MYBBP1A] |
| Q9UNW3 | Human Coat Protein RIC-2 |
| Q9BWE0 | Human REPIN1 Protein (Hypothetical Protein ZNF464) |
| Q9ULL5 | Human KIAA1205 Protein |
| Q9NZH2 | Human Dhfr Oribeta-binding Protein RIP60 |
| Q9NZI3 | Human Linens epithelium-containing growth factor p52 |
| Q9NY27 | Human Regulatory Sub-Unit 2 of Proteinphosphatase-4 |
| Q86U91 | Human HMGA2/RAD51L1 Fusion protein |
| O95368 | Human Transcriptional Coactivator p52 |
| Q9P015 | Human HSPC145 (Mitochondrial Ribosome protein L15) |
| Q5U071 | Human HMG Protein 'box 2' |
| Q9H0Y1 | Human Hypothetical Protein DKFZp564I206 |
| Q6ZP45 | Human Hypothetical Protein FLJ26517 |
| P17096-2 | Splice Isoform HMG-Y of P17096 [HMGA1] |
| Q9Y6X0 | SETBP_HUMAN SET-binding Protein (SEB) [SETBP1] |
| Q8TEK3 | DOT1L_HUMAN Histone-Lysine N-Methyltransferase |
| Q8TEK3-2 | Splice Isoform 1 from Q8TEK3 [DOT1L] |
| Q03164 | HRX_HUMAN Zinc finger-Protein HRX (ALL-1) |
| Q86YP1 | Human Transcription factor MLL UPN96240 |
| Q86YN9 | Human Transcription factor MLL UPN95022 |
| Q03164-2 | Splice Isoform 4P-18B from Q03164 [MLL] |
| P04920 | B3A2_HUMAN Anion Exchanger Protein 2 |
| Q59GF1 | Human Anion Exchanger-2 type a-variant |
| Q8TAG3 | Human SLC4A2 Protein |
| Q6P391 | Human PSIP1 Protein |
| O75475 | Human Linens epithelium-containing growth factor p75 |
| Q9UEY6 | Human Anion exchanger-2 type a [SLC4A2] |
| Q9UEY5 | Human Anion exchanger-2 type b2 [SLC4A2] |
| Q9UEY4 | Human Anion exchanger-2 type b1 [SLC4A2] |
| Q9UER6 | Human Transcriptional coactivator p75 |
| O00256 | Human DFS70 |
| P04920-2 | Splice Isoform B1 of P04920 [SLC4A2] |
| Q9BTB1 | Human Hypothetical Protein MGC10561 |
| Q9UKB0 | Human HMG Protein-R |
| O43167 | ZBT24_HUMAN Zinc finger- and BTB-domain-containing protein |
| Q8N455 | Human ZBTB24 Protein [ZBTB24] |
| Q5TED5 | Human Zinc finger-Protein 450 [ZNF450] |
| Q96CK0 | Human Zinc finger-Protein 653 |
| Q96AS7 | Human Zinc finger-Protein 653 |
| P51888 | PRELP_HUMAN Prolargine Precursor |
| Q5JPC9 | Human Hypothetical Protein DKFZp667H216 |
| Q6FHG6 | Human PRELP-Potein |
| Q6ZR44 | Human Hypothetical Protein FLJ46672 |
| Q8NEZ4 | MLL3_HUMAN Myeloid/lymphoid-Leukaemia protein 3 Homologon |
| Q96AC6 | KIFC2_HUMAN Kinesine-like Protein KIFC2 |
| Q9C0H5 | K1688_HUMAN Protein KIAA1688 |
| P52926 | HMGIC_HUMAN HMG Protein I-C |
| Q9UKV3 | ACINU_HUMAN Inductor of apoptotic Chromatin condensation |
| Q59F82 | Human C21orf2-Protein variant |
| Q5VYT7 | Human OTTHUMP00000021181 |
| Q96M56 | Human Hypothetical Protein FLJ32810 |
| Q69YJ6 | Human Hypothetical Protein DKFZp667N107 |
| Q8NEY3 | SPAT4_HUMAN Spermatogene-associated Protein 4 |
| Q12809 | KCNH2_HUMAN Potassium Potential-controlled Ion channel Sub-family |
| Q8IYY4 | Human protein similar to the DAZ-interacting protein 1 [DZIP1L] |
| Q6ZN04 | Human Hypothetical Protein FLJ16544 |
| Q5SXN7 | Human Serologically defined colon cancer antigen 3 |
| Q8IVG2 | Human KIAA2009 Protein (Fragment) [RKHD3] |
| Q75VX8 | Human KIAA2038 Protein (Fragment) [KIAA2038] |
| Q12809-2 | Splice Isoform 2 von Q12809 [KCNH2] |

Against this background the present invention also relates to L-nucleic acids and in particular spiegelmers, which are directed against any of the target molecules mentioned in Tables 1 to 3.

Since the L-nucleic acid is used as an intracellularly active agent, in particular within a cell, in order to bind there to an intracellular receptor, intracellularly different forms of the interactions between the intracellular receptor and its interaction partners can be influenced. Depending on the type of interaction partners of the intracellular receptor, the intracellular use of L-nucleic acids thus enables interactions of proteins, nucleic acids, lipids, carbohydrates, or combinations of proteins, nucleic acids, lipids, carbohydrates with one another and between one another to be influenced.

In connection with the use according to the invention of a L-nucleic acid, in particular a spiegelmer, as intracellular agent and the method for binding an intracellular receptor, it should be noted that this preferably relates to an in vitro application and to an in vitro method.

In connection with the use according to the invention of a L-nucleic acid, in particular a spiegelmer, for the production of a medicament for the treatment and/or prevention of a disease and/or for the production of a medicament for diagnostic purposes, the target molecule is an intracellular target molecule. In this connection the intracellular target molecule is one that is causily or non-causily involved in the disease or illness to be prevented, treated or diagnosed, but in any case its binding to a L-nucleic acid that binds specifically thereto means that, in the case of a medicament, the disease is alleviated, prevented or cured, and/or in the case of a diagnostic agent the disease or a predisposition thereto can be established or diagnosed. As used herein the concept of diagnosis include an initial diagnosis as well as subsequent diagnoses, in particular diagnoses or investigations in order for example to follow or to determine the progression of the disease or the stages of the disease. It is within the scope of the invention that the target molecule is an intracellular receptor as described herein, in particular a transcription factor, an intracellular target molecule or an HMG protein. Within the scope of the present invention it is most particularly preferred if the target molecule is present intracellularly, i.e. within a cell, and the interaction having an influence on the disease and/or diagnosis takes place intracellularly between the L-nucleic acid and in particular the spiegelmer, and the target molecule, i.e. the receptor. It is also within the scope of the present invention if the target molecule is present outside a cell and the interaction between the L-nucleic acid and in particular the spiegelmer, and the target molecule, i.e. the receptor, takes place extracellularly.

The indications for use of the medicament produced using an L-nucleic acid, in which the nucleic acid is directed against an intracellular target molecule, follow for the person skilled in the art from the involvement of the intracellular target molecule in the respective pathogenicity mechanism on which the indication is based. Thus, it is known for example for HMGA proteins that these are associated with carcinomas (inter alia of the breast, lungs, skin, thyroid) as well as leukaemias and lymphomas and other malignant tumours, such as inter alia sarcomas (rhabdomyosarcoma, osteosarcoma). Also, HMGA proteins are expressed in many types of mesenchymal tumours, including inter alia hamartomas (breast and lungs), fatty tissue tumours (lipomas), pleomorphic adenomas of the salivary glands, uterine leiomyomas, angiomyxomas, fibroadenomas of the breast, polyps of the endometrium and atherosclerotic plaques. HMGA is an interesting therapeutic target. Blockade of HMGA could be a suitable starting point for controlling cancer and preventing its metastatic spread. As described in detail herein, L-nucleic acids directed against HMGA proteins are also suitable for the diagnosis and/or treatment of virus diseases and arteriosclerosis on account of the involvement of HMGA proteins in the regulation of the transcription of a large number of viral genes or the marked expression of HMGA and in particular HMGA1 in the tissues affected by arteriosclerosis, which is associated with neointimal, vascular smooth muscle cells, macrophages and new blood vessels.

Although—as has been surprisingly found by the present inventors—nucleic acids, preferably L-nucleic acids and particularly spiegelmers, are able as such to penetrate a phospholipid double membrane such as a cytoplasmic membrane and then to be intracellularly functional in the sense of the specific interaction with the intracellular receptor, the effectiveness of the infiltration of the L-nucleic acid can be influenced and in particular enhanced by the use of various techniques. These techniques include the use of chemical compounds or molecules as well as the use of physical measures. Irrespective of the type, these techniques are herein generally referred to as delivery vehicles. It is within the scope of the present invention that the inventors have likewise established that aptamers too exhibit this property, and like the spiegelmers can similarly be used involved together with the composition according to the invention for basically the same purposes, applications and uses.

In the use of chemical compounds and molecules, a further distinction is whether the nucleic acid needs to be modified or not for the delivery. A modification for the purposes of using a delivery vehicle is generally not necessary if the delivery vehicle is or comprises a vesicle, such as for example in the case of liposomes, polypeptide vehicles, cyclodextrins, dendrimers, nanoparticles and microparticles, and also polyethyleneimine. A modification for the purposes of using a delivery vehicle is on the other hand normally necessary if the delivery vehicle uses receptor-mediated endocytosis, fusogenic peptides, signal peptides or lipophilic conjugates. The group of physical techniques includes in particular electroporation and iontophoresis. It will be recognised that further techniques for transporting a compound through a phospholipid double membrane such as a cytoplasmic membrane are known to the person skilled in the art in this field, which in principle are also suitable for the transfer of a functional nucleic acid, such as for example an aptamer and/or a spiegelmer.

The individual delivery vehicles which can be used within the scope of the various aspects of the present invention will be described in more detail hereinafter.

Liposomes consist of artificial cationic lipids such as N-[1-(2,3-dioleoyloxy)propyl]-N,N,N-trimethylammonium chloride (DOTMA) and N-[1-(2,3-dioleoyloxy)propyl]-N,N,N-trimethylammonium sulfate (DOTAP), in which the cationic groups interact with the negatively charged nucleic acids and neutralise their anionic charge. The transport takes place via endocytosis (PNAS, 93:11493-11498, 1996). However, cationic liposomes are cytotoxic, especially in higher concentrations, which restricts their use in vitro and in vivo (Biochem Biophys Res Commun, 197:818, 1993; Biochem Biophys Res Commun, 1372:55-68, 1998). On the other hand the amphiphilic pyridinium-based lipid SAINT-2 is a non-toxic formulation (Nucleic Acids Res, 29:2079-2087, 2001). Also, pH-sensitive liposomes are a possible alternative, which consist of amphiphatic molecules such as cholesteryl hemisuccinate (CHEMS) and dioleyl phosphatidyl ethanolamine (DOPE) (J Pharmacol Exp Ther, 297:1129-1136, 2001). Widely differing formulations of liposomes can be found in the review articles by Dass and Torchili (Drug Delivery, 9:169-180, 2002; Nat Rev Drug Disc, 4:145-160, 2005).

With receptor-mediated endocytosis (RME) transport mechanisms which are already present in the cell membrane are utilised. For this purpose the nucleic acid is coupled for example via a poly-L-lysine (PPL) linker covalently to a transporter protein ("carrier" protein). The choice of transporter protein depends in this connection on the ability to bind to specific receptors of the cell membrane and to accumulate in the cell by endocytosis. A cell-specific transport can thus be realised. For example, an antisense phosphorothioate directed against c-myc could be introduced into M-14 human melanoma cells (Anticancer Res, 17:29-35, 1997). However, an effective transport by means of RME depends in this case not only on the affinity of the receptor for the ligand, but also on the limitation of the selected receptor as regards the cells—especially in vivo. Furthermore the selected ligand must be inactive or have an enhancing effect as regards the therapeutic result, in order to avoid a possible toxicity of the transport vehicle. Thus, the selection and the ubiquitous propagation of the selected receptor in vivo is decisive for a successful RME-based transport. Moreover, a sequestration of nucleic acids in endosomal compartments has been observed in RME-based transport, which would appear to make this method not very promising for an intracellular transport or an intracellular release or delivery. Most important of all, the coupling between the receptor and nucleic acid must be chosen so that the function of one or other is not reduced (J Pharmaceutical Science, 92 (8):1559-1573, 2003).

Fusogenic peptides have been used to enable peptide-oligonucleotide conjugates to fuse with the cell membrane and thus effect the transport in the cell (Bioconjug Chem, 9:466-475, 1998; Bioconjug Chem, 6:43-53, 1995; Nucleic Acids Research, 25:2730-2736, 1997).

The selected import of nuclear proteins from the cytosol into the nucleus is mediated by short peptide sequences, which are termed nuclear localisation signals (NLS). Thus, various NLS peptide derivatives can be used in order to transport nucleic acids into the nucleus (Bioconjug Chem, 10:1005-1012, 1999; Bioconjug Chem, 10:598-606, 1999; Bioconjug Chem, 6:101-108, 1995). In addition there are also so-called signal import peptides (IP), which can promote the cellular uptake of nucleic acids and could be derived for example from Kaposi's fibroblast growth factor (K-FGF) (Adv Drug Deliv Rev, 44:35-49, 2000).

Vesicles similar to viral capsids can be formed by blocks of polypeptides, which can serve as possible transport vehicles for an intracellular transport (Nat Materials, 3(4):244-8, 2004).

The hydrophilic character of oligonucleotides and the anionic phosphodiester backbone reduce the cellular permeation. Lipophilic conjugates are therefore one possible way of increasing the ability of oligonucleotides to bind to lipoproteins and thereby improve intracellular delivery. The conjugate that has been most thoroughly investigated is cholesterol (Antisense and Nucleic Acid Drug Development, 12:103-128, 2002).

Cyclodextrins are cyclic oligosaccharides, which have a central hydrophobic cavity and multiple hydroxyl groups on the outer surface. Cyclodextrins have therefore already been used for the transport of anti-sense oligonucleotides in human T cell lines (Antisense Res Dev, 5:185-192, 1995) and have also been used in vivo for intracellular transport and for intracellular release or delivery of immunogenic CpG sequences (Biochem Pharmacol, 52:1537-1544, 1996). A wide variety of formulations of cyclodextrins are given in the review article by Davis and Brewster (Nature Reviews Drug Discovery 3:1023-1035, 2004).

Dendrimers are highly branched macromolecules, which are composed of repetitive units of, typically, polyamides. The molecules carry functional groups such as primary amino groups on their surface, which interact with other molecules by electrostatic interaction. A complex structure formation thus takes place rapidly and in a highly reproducible manner, which leads to complexes of low cytoxicity (Nucleic Acids Research, 28:4225-4231, 2000; Clin Cancer Res, 7:3606-3612, 2001).

Cyanacrylate nanoparticles have been tested since the beginning of the 1990s for the release or delivery of oligonucleotides. The interaction of oligonucleotides with the nanoparticles takes place through ion pairs of the anionic charge of the oligonucleotides with various hydrophobic cations, principally with charged nanoparticles. Polyisohexyl cyanoacrylate (PIHCA), polyisobutyl cyanoacrylate (PIBCA) or polyhexyl cyanoacrylate (PHCA) are commonly used for the formation of nanoparticles, although a large number of lipophilic cation-oligonucleotide pairs have also been tested (Pharm Res., 1:1370-1378, 1994; PNAS, 91:10460-10464, 1994; Pharm Res, 9:441-449, 1992). Also, nanoparticles have already been employed for in vivo use (Biochem Biophys Res Commun, 279:401-406, 2000; Pharm Res, 13:38-43, 1996).

Microparticles or so-called microspheres are typically formed from biodegradable polymers such as poly(d,l-lactide-co-glycolides [P(LA-GA)] and are used for the delayed release of oligonucleotides (J Pharm Sci, 91:790-799; 2000; J Controlled Release, 69:197-207, 2000; J Drug Traget, 5:291-302, 1998).

Electroporation is a transport technology, which uses a strong electric field in order to destabilise the lipid double membrane, and thereby permeabilise the cell membrane and thus effect a transport of the substance to be administered, which can also be present in ionised form, into the cell (iontophoresis). Electroporation has already been successfully used in order to effect transdermal transport of oligonucleotides ex vivo as well as in vivo (Int J Pharm, 184:147-156, 1999; J Drug Traget, 5:275-289, 1998; Pharm Res, 15:1596-1602, 1998; Int J Cancer, 85:260-266, 2000; Biochem Biophys Res Commun, 212:286-292, 1995; Blood, 88:731-741, 1996).

The uptake of "naked" oligonucleotides into cells can be improved in vitro and ex vivo by the use of high pressure.

The need for closed systems in order to use this technology means that it can only be used for ex vivo applications (PNAS, 96:6411-6416, 1999; Hum Gene Ther, 10:2355-2664, 1999).

Also, the use of shockwaves, acoustic high pressure pulses, effects the transport of oligonucleotides into cells (J Mol Med, 79:306-313, 2001; Cancer Res, 58:219-221, 1998). Ultrasound is an acoustic technology comparable to shockwaves, but employs higher frequencies (MHz instead of Hz) and shorter application times (from seconds to minutes), and has already been used in a supporting role in gene therapy techniques (Hum Gene Ther, 7:1339-1346, 1996; Invest Radiol, 32:723-727, 1997; Ultrasound Med Bio, 25:1451-1457, 1999).

In a further aspect of the present invention a new delivery vehicle is provided, which is suitable in particular for the transport of functional nucleic acids such as aptamers, preferably functional L-nucleic acids, and most particularly preferably spiegelmers. The delivery vehicle is in this case a micelle-like or liposome-like structure based on polyethyleneimine. Without wishing to be too specific in the following description, the present inventors start from the assumption that the nucleic acid is present embedded or contained in the micelle-like or liposome-like structure. Polyethyleneimine can in principle be present and also used as linear or branched polyethyleneimine, polyethyleneimine in the branched form being particularly preferred. Moreover, polyethyleneimine can exist and can also be used as high molecular weight or low molecular weight polyethyleneimine. Preferably high molecular weight polyethyleneimine has a molecular weight of about 800 kDa and low molecular weight polyethyleneimine has a molecular weight of about 3 kDa. Within the scope of the present invention a polyethyleneimine with a mean molecular weight of about 25 kDa is preferred, a branched polyethyleneimine with a molecular weight of about 25 kDa being particularly preferred.

Although it is not essential for an effective implementation, it is nevertheless preferred if in the delivery vehicle according to the invention the nucleic acid itself to be delivered also carries a modification. In this connection it is preferred if the modification is selected from the group comprising PEG residues. It is furthermore preferred if the PEG residue has a molecular weight of about 1000 to 10000 Da, preferably about 1200 to 5000 Da, more preferably about 1500 to 2500 Da and most particularly preferably about 2000 Da.

When mixing the nucleic acid with the delivery vehicle to produce a composition according to the invention, the ratio of the total number of nitrogen groups of the polyethyleneimine to the total number of phosphate groups of the nucleic acid to be delivered via or packaged with the delivery vehicle is adjusted to about 1 to 20, preferably about 1.5 to 10, more preferably 2 to 5, and most particularly preferably about 2 to 3.

The delivery vehicle according to the invention thus enables the mechanism of intracellular transport of nucleic acids via condensation or packing with charged particles or reagents and associated change in the charge of the overall complex, to be used also for functional nucleic acids such as aptamers, and in particular L-nucleic acids such as spiegelmers. This complex is readily taken up through endocytosis and thereby passes into the cytosol of the cell. A disadvantage of this method is the stability of the DNA/RNA and the release of the nucleic acid from the endosomal compartment. In the cytosol of the cell a lysosome is rapidly formed from the tightly constricted endosome due to the introduction of proteases or nucleases and by protonation of the compartment. There nucleases break down the nucleic acids. This does not apply however to spiegelmers, since due to their unnatural configuration these are nuclease-stable. Also, nucleic acids are not stable in the acidic environment of the lysosome. However, this is more true of nucleic acids synthesised from DNA, and less true of nucleic acid from RNA. The whole complex is rapidly transported out of the cell again by exocytosis and breakdown in the Golgi apparatus, and accordingly only a few nucleic acids pass into the cell. One of the challenges which a suitable transfection system has to overcome is thus the stabilisation as well as the release of the nucleic acid from the endosomes into the cytosol. As regards stability, RNA spiegelmers have ideal properties for a transfection of eukaryotic cells, since being enantiomers they are not split by enzymes.

The use according to the invention of L-nucleic acids and in particular in connection with the composition according to the invention is important specifically for this class of active substances, since their action mechanism is based on a stoichiometric approach and not on a catalytic approach, in which the intracellular release of just a few molecules is already sufficient to achieve the desired effect. To this extent the present invention satisfies a need that was not hitherto met by the techniques of the prior art.

The transfection system according to the invention that is provided and elaborated by the delivery vehicles according to the invention is based on the formation of micelles from nucleic acids and branched polyethyleneimine (PEI). The phosphodiester backbone of the nucleic acids interacts with the free nitrogen positions of the PEI and forms small micelles through cross-linking, which have a positive charge on account of the PEI. These micelles are readily taken up as endosomes from a cell by constriction of the plasma membrane. The PEI now buffers inflowing protons, as a result of which many chloride ions in the interior of the endosome lead to a swelling of the compartment on account of the osmotic pressure. This effect of PEI is described in the literature as the proton sponge effect, and ultimately leads to the rupture of the endosome and the release of the spiegelmers into the cytosol. (Pharm Res, 22 (3): 373-80, 2005; Eur J Cell Biol 83 (3): 97-111, 2004; Gene Ther 9(24):1700-7, 2002).

It is within the scope of the present invention to apply the composition according to the invention as an aerosol.

In addition spiegelmers can be derivatised with signal peptides for intracellular as well as intranuclear delivery, and also for organ-specific delivery. A coupling of signal peptides directly to the polyethyleneimine can be used for a targeted localisation in organs or within the cell.

In another further aspect the present invention relates to L-nucleic acids, in particular spiegelmers and more preferably RNA spiegelmers, which are directed against HMGA proteins. The spiegelmers disclosed herein directed against HMGA proteins are in particular examples of the knowledge, likewise forming the basis of the present invention, that L-nucleic acids and in particular spiegelmers are able to overcome a phospholipid double membrane or a cytoplasmic membrane of a cell and bind intracellularly with the intracellular receptor, for the specific binding to which they have been selected. As regards the configuration of the HMGA proteins and the L-nucleic acids directed against the latter, the comments made herein regarding the intracellular use of L-nucleic acids also apply in connection with the present aspect of the invention (and vice-versa), and is referred to again at this point in order to avoid unnecessary repetitions.

The HMG (high mobility group) family of DNA-binding phosphoproteins are present as non-histone components of chromatin throughout mammalian cells (Grosschedl et al. 1994). The basic HMG proteins are sub-divided into three different families—HMGB (formerly HMG-1/-2), HMGN (formerly HMG-14/-17), and the HMGA family (formerly HMG-I/Y/C). Each HMG family has its characteristic functional sequence motif: the "HMG box" (HMGB family), the "nucleosomal binding domain" (HMGN family), and the "AT hook" (HMGA family).

According to the current state of knowledge the HMGA family comprises two genes, HMGA1 and HMGA2. Three different proteins can be expressed by alternative splicing by HMGA1, (HMGA1a [formerly: HMG-I], HMGA1b [formerly: HMG-Y], HMGA1c [formerly: HMG-I/R]), whereas only one protein (HMGA2 [formerly: HMGI-C]), can be expressed by HMGA2. HMGA1a, HMGA1b and HMGA2 are polypeptides of approximately 100 amino acid length and have a modular sequence organisation: they possess three strongly basic regions ("AT hook"), which bind the narrow small channels of double-stranded AT-rich DNA (Reeves & Nissen 1990). The C-terminus on the other hand contains many acidic amino acids. The proteins do not have a stable secondary structure when free in solution, and only adopt a defined conformation when they are present in the complex with DNA or other proteins (Huth et al 1997). HMGA proteins belong to the most strongly modified proteins in the mammalian cell nucleus and are phosphorylated, acetylated and methylated (Reeves & Beckerbauer 2001).

The HMGA proteins per se do not have any transcriptional activity, but being so-called architectonic transcription factors they organise through their protein-protein and protein-DNA interactions the formation of the nucleoprotein-DNA transcription complex (Wolffe 1994). They thus exert a regulatory activating or inhibitory influence on the expression of a large number of genes. The most prominent example of a positive regulation is the involvement of HMGA1 in the regulation of IFN-β (Thanos & Maniatis, 1992). Thus, for example in the case of the IFN-β promoter HMGA1b stimulates the binding of NF-kB and ATF-2 to the DNA double helix and at the same time alters the DNA structure in such a way that NF-kB and ATF-2 can interact with one another and presumably also with the rest of the transcription machinery (Thanos & Maniatis 1992, Du et al 1993). A further transcription-activating effect in connection with arteriosclerotic pathogenesis is the CD44 gene regulation induced by HMGA1 (Foster et al 1998). CD44 is a cell surface glycoprotein and is involved in the migration and proliferation of smooth muscle cells after endothelial damage (Jain et al 1996, Cuff et al 2001). The transcriptional regulation of CD44 is induced by the binding of c-Fos and c-Jun to the AP-1 binding site in the CD44 promotor and is strengthened by the binding of HMGA1. Investigations in rats has shown that due to CD44 over-expression, there is an intensified recruitment of smooth muscle cells, which has a direct influence on the formation of arteriosclerotic lesions (Pellacani et al 1999; Foster et al. 1998; 2000).

Investigations on the expression of the HMGA1 gene localised in the chromosomal band 6p21.3 and of the HMGA2 gene localised in the region 12q14-15 showed that these are mainly active in processes of cell differentiation.

Accordingly, a strong expression of these genes can be found during embryo development and in undifferentiated cells (Chiappetta et al 1996) as well as in growth factor-stimulating cells (Friedman et al 1993; Johnson et al 1990; Ogram et al 1995; Holth et al 1997). In adult, differentiated tissue, HMGA1 is strongly expressed only in the retina, while HMGA2 is not found at all in the other tissues and HMGA1 is found only in very low concentrations (Bussemakers et al 1991; Chiappetta et al 1996; Rogalla et al 1996; Zhou et al 1995; Chau et al 2000). A reactivated expression of HMGA proteins in differentiated normal tissue is at the same time associated with the growth and differentiation of adipocytes (Zhou et al 1995; Anand & Chada 2000; Melillo et al 2001), the proliferation of smooth muscle cells in the blood vessels after vascular damage (Chin et al 1999), in the immune response in inflammatory reactions (Pellacani et al 1999), as well as in apoptotic processes (Diana et al 2001; Sgarra et al 2003). The amount of HMGA1 varies in this connection depending on the proliferation rate of the cells (Johnson et al 1990).

During the course of embryo development the HMGA1 expression is concentrated on specific organs of ectodermal, mesodermal or endodermal origin, whereas HMGA2 is restricted to mesenchymal tissue. Up to now no information exists concerning the phenotype of HMGA1 knockout mice, possibly because the lack of this factor has damaged embryo development too severely. HMGA2 knockout mice on the other hand exhibit dwarfism and have particularly little fatty tissue (Zhou et al 1995) and furthermore are resistant to diet-induced obesity (Anand & Chada 2000).

Finally, HMGA2 and HMGA1b expression is not detectable in the fatty tissue of normal mice, but is dramatically increased in the fat of fatty or diabetic mice (Chada et al. 2004), which points to a connection between adiposity/obesity and HMGA expression.

Over-expression of HMGA1 influences in particular (Reeves et al 2001):
Cell cycle and growth regulators such as cdc25A,
Intermediary filament markers such as cytokeratin, type 1
Apoptosis regulators such as TRAR15
Oncogenes and tumour suppressor genes such as MET
Genes for DNA repair and recombination such as DNase X
Cell fate and development regulators such as frizzled-5
Receptors such as FGFR1
Cell adhesions, motility and invasion genes such as collagen type 1
Angiogenesis regulators such as FGFR2
Invasion regulators such as MMP-16
Small GTPases of the Rho family and their regulators such as RhoC
cell-cell interaction genes such as cadherin 12
Growth factors and cytokines such as IL-11

Abnormal regulation of HMGA1 could therefore lead to general alterations of gene expression and thereby contribute significantly to the formation of transformed and/or metastatic phenotypes.

HMGA protein appear to play different roles in mesenchymal and epithelial tumours: in malignant epithelial tumours HMGA expression is associated rather with later stages of carcinogenesis, whereas benign tumours—more often rarely converting mesenchymal tumours—already express HMGA in early hyperplasia. This points to the fact that HMGA proteins in tissues of different embryonic origin fulfil different functions, from which also directly follows the corresponding uses of the L-nucleic acids according to the invention in the diagnosis and/or treatment of corresponding diseases, as is also illustrated in more detail hereinafter.

The expression of HMGA1 in various human and animal neoplasms was investigated in animal models. The role of HMGA1 was demonstrated in animal models of tumourigenesis (Leman et al 2003; Ram et al 1993) as well as neoplastic progression (Bussemakers et al 1991; Nestl et al 2001; Ram et al 1993).

Raised expression of the HMGA1 gene has been demonstrated in the following carcinomas
Prostate (Bussemaker et al 1991; Tamimi et al 1996; Leman et al 2003; Nestl et al 2001)
Pancreas (Nestl et al 2001; Abe et al 2000, 2002; Tarbe et al 2001)
Thyroid (Chiappetta et al 1998, 1995)
Cervix (Bandiera et al 1998)
Stomach (Xiang et al 1997)
Breast (Holth et al 1997; Baldassarre et al 2003; Reeves et al 2001; Nestl et al 2001; Ram et al 1993; Dolde et al 2002)
Colon/Rectum (Fedele et al 1996; Abe et al 1999; Kim et al 1999; Chiapetta et al 2001)
Ovaries (Masciullo et al 2003)
and furthermore in
Neuroblastoma (Giannini et al 2000; 1999) as well as
Lymphoma (Wood et al 2000a; b).

The precise reason for the increased expression and the role of the HMGA1 gene in the pathogenesis of the tumour and the process of metastasis has still not been fully clarified. Various studies indicate however that the strength of the HMGA1 expression by the respective tumour as a prognostic marker correlates with its metastasing potential and thus represents a characteristic feature of a malignant transformed cell (Giancotti et al 1987).

Further HMGA1-associated—in this case benign, mesenchymal tumours—are characterised by chromosomal changes in the chromosomal HMGA1 region 6p21.3. Such aberrations have up to now been described inter alia in
Uterine leiomyoma (Mark et al 1988; Ozisik et al 1993)
Lipoma (Sreekantaiah et al 1990)
Endometrial polyps (Fletcher et al 1992; Dal Cin et al 1995) as well as
chondroid hamartoma of the lungs (Fletcher et al 1991; Johansson et al 1992, 1993).

Aberrations in the genetic mechanisms which control growth and proliferation are the primary cause of carcinogenesis. The expression of HMGA proteins is strongly associated with tumour development, as has been shown in a number of articles and papers (Giancotti et al. 1987, 1989, 1993). Thus, a significant HMGA2 expression was found in chemically or virally caused tumours as well as in spontaneously occurring tumours, whereas this protein could not be detected in non-transformed cells or healthy tissue (Giancotti et al. 1989). In accord with this, in the case of cells infected with oncogenic retroviruses in which the synthesis of HMGA2 expression had been specifically blocked, various phenotype markers for transformation were absent (Berlingieri et al. 1995).

The key role of HMGA proteins in normal as well as pathological growth has been elucidated in mouse models: HMGA2 knockout mice exhibit stunted growth, i.e. the animals are ca. 60% smaller than wild type mice. These dwarf mice however have a high resistance to chemically induced skin tumours.

In the last few years structural aberrations of the chromosome region 12q14-15 involving the HMGA2 gene have been found with the aid of cytogenetic investigations for a whole number of benign tumours of mesenchymal origin, these being the largest group of harmless neoplasias in man. Despite a large number of aberrations (Schoenmakers et al 1995; Kottickal et al 1998; Klotzbüchel et al 1999) the altered forms nevertheless always exhibit a common feature: they retain all three DNA-binding domains, but at the same time lose the acidic C-terminal domain as well as, at the RNA level, the information of the 3' UTR.

Such changes have already been found for many (mostly benign) mesenchymal HMGA-associated tumours:
Uterine leiomyomas, the most common abdominal tumours in women and the reason for more than 200,000 hysterectomies per year in the USA (Heim et al 1988; Turc-Carel et al 1986; Vanni et al 1988)
Lipomas (Heim et al 1988; Turc-Carel et al 1986; Mandahl et al 1987; Sreekantaiah et al 1991; Belge et al 1992)
Endometrial polyps (Walter et al 1989; Vanni et al 1993; Dal Cin et al 1995)
Chondroid hamartomas of the lungs (Fletcher et al 1991, 1995; Dal Cin et al 1993)
Pleomorphic adenomas of the salivary glands (Mark et al 1980, 1986; Bullerdiek et al 1987)
Haemangiopericytomas (Mandahl et al 1993)
Chondromatous tumours (Mandahl et al 1989; Bridge et al 1992)
Benign tumours of the breast (Birdsal at al 1992; Rohen et al 1995; Staats et al 1996)
Aggressive angiomyxomas (Kazmierczak et al 1995)
Diffuse astrocytomas
Osteoclastomas (Nuguera et al 1989)

The main cause of mortality and morbidity in cancer patients is the metastatic spread of the primary neoplasm in the body. Metastasis is not a simple process, since a successful colonisation of distant organs by disseminated neoplastic cells has to pass through many stages. Neoplastic cells have to be released from the primary neoplasm, enter the bloodstream, extravasate to distant sites, and finally proliferate again in the parenchyma of the corresponding organ. Many genes which express proteins such as proteases, adhesion molecules, motility factors and angiogenic factors are involved in the various stages of this highly complex, metastatic cascade.

Which of these genes is ultimately decisive as regards metastisis is not known. The HMGA1 gene, being one of the most important factors controlling this process, is however a likely candidate. The gene products of HMGA1 influence the transcription of many genes that are important for successful metastasis. For example, it has already been shown that other metastasis-associated genes are themselves expressed at a reduced level in suppression of HMGA1 expression (Battista 1998; Vallone 1997).

HMGA1 is therefore an important therapeutic target molecule. The blockade of HMGA1 is thus in principle suitable for controlling the cancer and preventing its metastatic spread (Evans 2004; Sgarra 2004). Thus for example, by using antisense RNAs directed against HMGA transcripts, cell proliferation in cancer cells has been reduced in vitro or the cells have even undergone apoptosis (Masciullo 2003; Scala 2000; Chau 2003). It has been shown in animal models that the growth of various pancreatic cancer xenografts is dramatically reduced by gene therapy (adoenoviral expression of antisense RNAs directed against HMGA transcripts) (Trapasso et al 2004).

HMGA1 could furthermore be used as a prognostic diagnostic marker in order to determine which patients would benefit from an aggressive cancer treatment. There is a close correlation between the degree of the malignant transformation and the amount of expressed HMGA1. This can in turn be correlated with a poor prognosis in many types of human cancer, such as prostate cancer (Tamimi 1996; Bussemakers 1991) and colorectal carcinoma (Abe 1999) and neuroblastoma (Giannini 2000).

HMGA proteins are used by many viruses as well as by control factors provided by the host cell for the expression of viral genes or as co-factors, inter alia by Human papovavirus JC (Leger et al 1995)
Epstein-Barr virus (Schaefer et al 1997)
Herpes simplex virus (Panagiotidis 1999; French et al 1996)
HIV-1 virus (Henderson et al 2000).

In particular HMGA proteins are involved in the regulation of the transcription of a large number of viral genes in a host cell. Examples of this are the regulation of the expression of the early and late expressed genes of the human papovavirus JC (Leger et al. 1995), regulation of the EBNA1 (Epstein-Barr virus nuclear antigen 1) gene of the Epstein-Bar virus (EBV), which is jointly responsible for controlling viral latency (Schaefer et al. 1997), regulation of the IE-3 (immediate-early) gene of the Herpes simplex Virus-1 (HSV-1), which codes the prematurely expressed protein ICP4 (Panagiotidis et al. 1999), regulation of the promoter 2, active during the latency phase, of HSV-1 (French et al. 1996) and regulation of the LTR (long terminal repeats) promoter of the humane HIV-1 virus (Henderson et al 2000).

The requisition of HMGA by the host cell in the context of viral diseases is not only restricted to viral gene regulation. HMGA1 also appears to play a decisive role as architectonic co-factor in the integration of the viral DNA of the HIV-1 virus, of the Moloney murine leukaemia virus (MoMuLv) and sarcoma bird flu virus (ASV) into the human genome, and therefore appears to be an interesting therapeutic approach in antiviral treatment (Van Maele et al. 2006, Li et al 1998, Hindmarsh et al. 1999).

Inhibitors of HMGA proteins are therefore also suitable for the treatment and diagnosis of virus infections (Reeves & Beckerbauer 2002).

As a result of the previously demonstrated involvement of HMGA proteins in various diseases and their suitability as diagnostic markers, L-nucleic acids and in particular spiegelmers directed against these proteins can be used for the prevention, treatment and diagnosis of the above diseases. Particularly preferred spiegelmers are in this connection the spiegelmers described herein. In this connection it is recognised by those skilled in the art that although the individual spiegelmers have been developed for a specific HMGA protein, as a result of the domain approach illustrated in Example 2 these also allow a cross-reactivity with other HMGA proteins, which can be seen from the alignment illustrated in FIG. 2.

Furthermore, it is recognised by those skilled in the art in this field that the nucleic acids according to the invention contain a number of structural motifs, which define a class of spiegelmers that bind as intracellular receptors to HMGA proteins. The various structural motifs are illustrated in more detail in Example 1.

The nucleic acids according to the invention comprise in a preferred embodiment also those nucleic acids which are substantially homologous to the sequences specifically disclosed herein. The term "substantially homologous" should preferably be understood in this connection to mean that the homology is at least 75%, preferably 85%, more preferably 90% and most preferably more than 95, 96, 97, 98 or 99%.

The term nucleic acids according to the invention or nucleic acids according to the present invention should furthermore be understood to include also those nucleic acids which comprises nucleic acid sequences such as are described herein, or parts thereof, preferably to the extent that the nucleic acids or the said parts thereof are involved in the binding to HMGA proteins. Such a nucleic acid can be derived from those disclosed herein, for example by shortening or truncation. A shortening can involve either one or both ends of the nucleic acids, as are disclosed herein. A shortening can also involve the inner sequence of nucleotides, i.e. can involve nucleotide(s) between the 5' and the 3' terminal nucleotides. Furthermore the term shortening should also be understood as referring to the deletion of as few as one individual nucleotide from the sequence of the nucleic acids disclosed herein. Shortening can also involve more than one region of the nucleic acid(s) according to the invention, in which connection each of these regions may be as small as one nucleotide long.

The nucleic acids according to the present invention may furthermore be either D-nucleic acids or L-nucleic acids. Preferably the nucleic acids according to the invention are L-nucleic acids. In addition it is possible that one or more parts of the nucleic acid is/are present as D-nucleic acids, or that at least one or more parts of the nucleic acids is/are L-nucleic acids. The term "part" of the nucleic acids is understood to denote as little as one nucleotide. Such nucleic acids are generally referred to herein as D-nucleic acids or L-nucleic acids.

Accordingly, in a preferred embodiment the nucleic acids according to the present invention consist of L-nucleotides and include at least one D-nucleotide. Such a D-nucleotide is preferably fixed to a part that is different from the region or regions that define the nucleic acids according to the present invention, and is preferably fixed to those parts thereof which are involved in an interaction with other parts of the nucleic acids. Preferably such a D-nucleotide is fixed to the end of each region or to each nucleic acid according to the present invention. In a preferred embodiment such D-nucleotides can act as a spacer or a linker, which preferably binds modifications such as PEG and HES to the nucleic acids according to the present invention.

Within the scope of the present invention, in one embodiment the nucleic acids according to the invention also include those acids which are part of a longer nucleic acid, wherein these longer nucleic acids can include several parts, at least one part being a nucleic acid according to the present invention or a part thereof. The other part or the other parts of these longer nucleic acids can either be a D-nucleic acid or a L-nucleic acid. Any combination can be used in conjunction with the present invention and for the purposes and uses such as have been described herein for the nucleic acids according to the invention. This other part or these other parts of the longer nucleic acid can have a function that is different from the binding function, and in particular from the binding to HMGA protein. A possible function is to allow an interaction with other molecules, e.g. for the purposes of immobilisation, cross-linking, detection, amplification, modification or increasing the molecular weight.

In particular in this connection L-nucleic acids as used herein are nucleic acids which consist of L-nucleotides, and preferably consist completely of L-nucleotides.

Accordingly, in particular D-nucleic acids as used herein are nucleic acids which consist of D-nucleotides, and preferably consist completely of D-nucleotides.

Irrespective of whether the nucleic acid according to the invention consists of D-nucleotides, L-nucleotides or a combination of the two, the combination being for example a random combination or a defined sequence of regions which consist of at least one L-nucleotide and at least one D-nucleic acid, the nucleic acid can consist of one or more deoxyribonucleotides, ribonucleotides and combinations thereof.

In a further aspect the present invention relates to a pharmaceutical composition which consists of at least one of the nucleic acids according to the invention in combination with one or more other nucleic acids, in which the other nucleic acid(s) preferably binds to target molecules other than HMGA protein or exerts a function different to that of the nucleic acids according to the invention.

The construction of the nucleic acids according to the invention as L-nucleic acids is advantageous for several reasons. L-nucleic acids are enantiomers of naturally occurring nucleic acids. D-nucleic acids are however not very stable in aqueous solutions and in particular in biological systems and in biological samples, on account of the extensive presence of nucleases. Naturally occurring nucleases, in particular nucleases from animal cells, are not able to break down L-nucleic acids. As a result of this the biological half-life of the L-nucleic acid in such a system, including the human and animal body, is significantly increased. On account of the lack of degradability of L-nucleic acids no nuclease breakdown products are produced and thus no resultant side effects are observed. This aspect in fact demarcates L-nucleic acids from all other compounds that are used in the treatment of diseases and/or disorders and include the presence of HMGA or its causal involvement. L-nucleic acids that bind specifically to a target molecule through a mechanism different from the Watson-Crick base pairing, or aptamers which consist partly or completely of L-nucleic acids, in particular those parts of the aptamer that are involved in the binding of the aptamer to the target molecule, are termed spiegelmers.

It is also within the scope of the present invention for the nucleic acids according to the invention to be in the form of single-strand or double-strand nucleic acids, regardless of whether they are present as D-nucleic acids, L-nucleic acids or D-L-nucleic acids, and whether they are DNA or RNA. Typically the nucleic acids according to the invention are single-strand nucleic acids, which on account of the primary sequence contain defined secondary structures and can therefore also form tertiary structures. The nucleic acids according to the invention may however also be double-stranded, in the sense that two strands which are complementary or partly complementary to one another are hybridised with one another. This imparts stability to the nucleic acids, which becomes important particularly if the nucleic acid exists in the naturally occurring D-form instead of the L-form.

The nucleic acids according to the invention can be modified. Such modifications can involve individual nucleotides of the nucleic acid and are well-known in the prior art. Examples of such a modification are described inter alia in Venkatesan N. et al. (2003) Curr Med Chem. October; 10(19):1973-91; Kusser, W. (2000) J Biotechnol, 74: 27-38; Aurup, H. et al. (1994) *Nucleic Acids Res,* 22, 20-4; Cummins, L. L. et al, (1995) *Nucleic Acids Res,* 23, 2019-24; Eaton, B. E. et al. (1995) *Chem Biol,* 2, 633-8; Green, L. S. et al., (1995) *Chem Biol,* 2, 683-95; Kawasaki, A. M. et al., (1993) *J Med Chem,* 36, 831-41; Lesnik, E. A. et al., (1993) *Biochemistry,* 32, 7832-8; Miller, L. E. et al., (1993) *J Physiol,* 469, 213-43. Such a modification may for example be an H atom, a F atom or a $O-CH_3$ group or $NH_2$ group at the 2' position of an individual nucleotide that is contained in the nucleic acid. Furthermore the nucleic acid according to the present invention can include at least one LNA nucleotide. In one embodiment the nucleic acid according to the present invention consists of LNA nucleotides, and preferably completely of LNA nucleotides.

In one embodiment the nucleic acids according to the present invention can be a multi-part nucleic acid. A multi-part nucleic acid as used herein is a nucleic acid that consists of at least two nucleic acid strands. These at least two nucleic acid strands form a functional unit, the functional unit being a ligand for a target molecule. The at least two nucleic acid strands can be derived from one of the nucleic acids according to the invention either by cleavage of the nucleic acid in order to produce two strands, or by synthesis from a nucleic acid corresponding to a first part of the total nucleic acid, i.e. nucleic acid according to the invention, and a further nucleic acid corresponding to the second part of the total nucleic acid. It is recognised that cleavage as well as synthesis can be used in order to produce a multi-part nucleic acid where more than the two strands described above by way of example can be present. In other words, the at least two nucleic acid strands are preferably different from two strands that are complementary to one another and hybridise with one another, although a complementarity can exist to a certain extent between the various nucleic acid parts.

The present inventors have established that the nucleic acids according to the present invention have a very advantageous $K_D$ value range or dissociation value range, and therefore a very advantageous binding constant. One way of determining the binding constant is to use an equilibrium binding assay, as is described in Example 1.

The $K_D$ value of the nucleic acids according to the invention is preferably less than 1 µM. A $K_D$ value of about 1 µM should be characteristic of a non-specific binding of a nucleic acid to a target. As will be recognised by those skilled in the art, the $K_D$ value of a group of compounds such as for example the nucleic acids according to the present invention varies within a certain range. The $K_D$ of about 1 µM mentioned above is a preferred upper limiting value for the $K_D$ value. The preferred lower limiting value for the $K_D$ of nucleic acids binding the target molecule can be about picomolar or less. It is within the scope of the present invention for the $K_D$ values of the individual nucleic acids which bind to HMGA, preferably to lie within this range. Preferred ranges can be selected by choosing a first number within this range and a second number within this range. Preferred upper values are 0.25 µM, 0.1 µM, and preferred lower values are 100 nM, 10 nM, 1 nM and 0.05 nM.

The nucleic acids according to the invention preferably bind to HMGA1b at 37° C. in solution with a dissociation constant $K_D$<20 nM, as illustrated in Example 2.

The nucleic acids according to the present invention can be of arbitrary length, provided that they are still able to bind to the target molecule. It is recognised in the prior art that specific lengths of the nucleic acids according to the present invention are preferred. Typically the length is between 15 and 120 nucleotides. It is also recognised by those skilled in the art that any whole number between 15 and 120 is a preferred possible length for the nucleic acids according to the present invention. Preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

In one embodiment the nucleic acids according to the invention are present in modified form. A particularly preferred form of modification is PEGylation. In this, the modification of the nucleic acids according to the invention involves coupling with polyethylene glycol (PEG) or other groups.

On account of the high stability of the nucleic acids according to the invention, in particular in the embodiment in which these exist as L-nucleic acids, it is possible to administer the nucleic acids according to the invention directly to a patient requiring such a treatment. Preferably the nucleic acids according to the invention are prepared as a physiological solution for topical or systemic application.

Apart from the direct use of the nucleic acids according to the invention for the treatment, prevention and diagnosis of the diseases described herein, these can be present or used individually or in combination with others in a pharmaceutical composition. The pharmaceutical composition according to the present invention accordingly comprises at least one of the nucleic acids according to the present invention and preferably a pharmaceutically acceptable binder. Such a binder may be any known binder or one known in the field. In particular such a binder is any binder, as is described in connection with the production of the medicament, as disclosed herein. In a further embodiment the pharmaceutical composition includes a further pharmaceutically active agent. It is within the scope of the present invention for the medicament described herein to constitute the pharmaceutical composition as is described herein.

Preferably the pharmaceutical composition is intended for intravenous administration. It is however also within the scope of the present invention for such pharmaceutical compositions to be administered intramuscularly, intraperitoneally or subcutaneously. Other administration routes are orally or intranasally, in which connection that form of administration is preferred that is least invasive, but at the same time retains the effectiveness of the pharmaceutical composition and the pharmaceutically active agent.

The nucleic acids according to the invention are preferably contained as such, or in connection with the pharmaceutical composition according to the invention, dissolved in a pharmaceutically acceptable solvent. Such solvents are in particular those that are selected from the group comprising water, physiological saline, PBS or a glucose solution, in particular a 5% glucose solution. Such a carrier can be for example water, buffer, PBS, glucose solution, preferably a 5% glucose solution (iso-osmotic), starch, sugars, gelatin or any other acceptable carrier substance. Such carriers are generally known to those skilled in the art in this field.

It is within the scope of the present invention for the pharmaceutical composition to contain at least one of the nucleic acids according to the invention in its various embodiments, including, but not restricted thereto, the nucleic acid as conjugate, as described herein.

In a further embodiment the medicament comprises a further pharmaceutically active agent. Such further pharmaceutical active agents are for example protease inhibitors, proliferation inhibitors and angiogenesis inhibitors and/or agents that have a cytostatic effect. Alternatively or in addition, such a further pharmaceutically active agent is a further nucleic acid according to the present invention. Alternatively, the medicament comprises at least one or more nucleic acids that bind to a target molecule that is different from HMGA, or has a function that is different from one of the nucleic acids according to the present invention.

The pharmaceutical composition according to the present invention can be used for the treatment, diagnosis and/or prevention of each of the diseases or disorders described herein.

In a further aspect the present invention relates to a method for the treatment of a living organism requiring such a treatment, wherein the method includes the administration of a pharmaceutically active amount of at least one of the nucleic acids according to the present invention. In one embodiment the living organism suffers from a disease, or there is a risk that it will suffer from such a disease, the disease being one of those mentioned herein, in particular a disease that is described in connection with the use of one of the nucleic acids according to the present invention for the production of a medicament.

Although the use of the nucleic acids according to the invention already follows from the involvement illustrated above of HMGA proteins in the various diseases and states, this aspect will be discussed further hereinafter for illustrative purposes.

HMGA proteins and their genes have in particular become increasingly involved in the diagnosis and prognosis of neoplastic diseases and have been proposed as potential biomarkers. In healthy tissue the expression level of HMGA1a/b proteins is very low, if detectable at all. Raised HMGA1a/b protein expression is characteristic of the phenotype of a large number of tumours and metastases of very many types of cancer (Sarhadi et al. 2006, Balcercak et al. 2005, Briese et al. 2006, Chang et al. 2005, Peters et al. 2005, Sato et al. 2005, Chiappetta et al. 2004, Li et al. 2004, Chuma et al. 2004, Donato et al. 2004, Czyz et al. 2004, Kettunen et al. 2004, Lee et al. 2004, Chen et al. 2004, Abe et al. 2003, Blacerczak et al. 2003, Flohr et al. 2003, Masciullo et al. 2003, Nam et al. 2003, Pierantoni et al. 2003). High HMGA protein expression correlates significantly with a poor prognosis and the formation of metastases. The detection of the HMGA1a/b expression level in biopsies and its histological characterisation is a diagnostic approach to the early detection, prognosis and identification of neoplastic diseases, in particular the diseases and conditions discussed hereinbefore.

Furthermore an association between HMGA1 proteins and arteriosclerotic plaques is described in the literature (Schlueter et al. 2005.). HMGA1 regulates CD44, one of the principal target genes for the formation of plaques. In this connection it was found, compared to the surrounding tissue, that the affected regions such as neo-intimal, vascular smooth muscle cells, macrophages and new blood vessels have a high expression of HMGA1. HMGA1 appears therefore to be one of the mediators in the formation of plaque and is thus a target molecule for diagnostic purposes.

The L-nucleic acids described here and in particular the spiegelmers, which bind HMGA1a/b, can within the scope of the methods known to the person skilled in the art be used in a similar way to antibodies. Up to now only very few specific (differentiating) and affine antibodies against HMGA1 have been identified and are commercially obtainable. This appears to be due to the non-existent secondary structure of HMGA1, which is not a suitable target for the MHC complex in the generation of antibodies.

Against this background it was however surprisingly found that the biotinylated HMGA1a/b-binding spiegelmer 5'-bio-NOX-A50 recognises in the western blot procedure HMGA1a/b as individual bands in cancer cell lines. Furthermore, as described in Example 2, recombinantly expressed HMGA1b protein could be detected. The detection of the biotinylated spiegelmer is carried out for example by an anti-biotin antibody conjugated by means of horseradish peroxidase (HRP).

The in vivo diagnosis of HMGA1a/b is a further approach, in which the nucleic acids according to the invention can be used. Tumours and metastases are often embedded in necrotic tumour cells, which release HMGA1a/b to the surrounding tissue. The detection of the extracellular HMGA1a/b is one approach to the diagnosis of tumours and metastases embedded in healthy tissue.

As preferably used herein, a diagnostic tool or diagnostic agent or diagnostic means is able to detect either directly or indirectly an HMGA protein, preferably HMGA1a/b, as described herein, and preferably HMGA1a/b as described herein, in connection with the various disorders and diseases. The diagnostic tool is suitable for detecting and/or searching for any of the diseases and conditions described herein. Such a detection is possible by the binding of the nucleic acids according to the present invention to HMGA1a/b. Such a binding can be detected either directly or indirectly. The corresponding methods and means are known to those skilled in the art in this field. The nucleic acids according to the present invention can inter alia be labelled, which permits the detection of the nucleic acids according to the present invention, preferably the nucleic acid that is bound or can bind to HMGA protein and preferably HGMA1a/b. Such a labelling is preferably selected from the group comprising radioactive, enzymatic and fluorescence labelling. In principle all known tests that have been developed for antibodies can be adapted to the nucleic acids according to the present invention, the target molecule-binding antibody being replaced by a target molecule-binding nucleic acid. In antibody tests which employ unlabelled target molecule-binding antibodies, the detection is preferably performed with a secondary antibody, which has been modified with radioactive, enzymatic or fluorescence labels and binds to the target molecule-binding antibody at its Fc fragment. In the case of a nucleic acid, preferably a nucleic acid according to the present invention, the nucleic acid is modified with such a label, the said label preferably being selected from the group consisting of biotin, CY-3 and CY-5, and such a label is detected by an antibody directed against such a label, for example an anti-biotin antibody, an anti-CY-3 antibody or an anti-CY-5 antibody, or in the case where the label is biotin, the label is detected by streptavidin or avidin, which naturally binds to biotin. Such an antibody, i.e. streptavidin or avidin, is in turn preferably modified with a corresponding label, for example a radioactive, enzymatic or fluorescence label, similarly to a secondary antibody.

In a further embodiment the nucleic acids according to the present invention are detected or analysed by a second detection agent, this detection agent being a molecular beacon. The technique of molecular beacons is known to those skilled in the art in this field. In brief, these molecular beacons are nucleic acid probes which are a reverse complement of the nucleic acid probe to be detected, and accordingly hybridise with a part of the nucleic acid probe to be detected. After the binding of the nucleic acid probe the fluorophore groups of the molecular beacon are separated from one another, which leads to a change in the fluorescence signal, preferably a change in intensity. This change correlates with the amount of nucleic acid probe that is present.

It is within the scope of the present invention that the nucleic acids according to the invention can appropriately be used as L-nucleic acids within the scope of the various aspects disclosed herein.

The nucleic acids according to the invention can furthermore be used as starting material for the design of pharmaceutical active substances (drug design). In principle there are two possible approaches to this problem. One approach consists in screening libraries of compounds, wherein such libraries of compounds are preferably libraries of low molecular weight compounds (low or small molecules). Such libraries are known to those skilled in the art in this field. In one embodiment the screening is a high throughput screening. Preferably high throughput screening is fast, efficient, and is carried out as a trial-and-error evaluation of active substances in a target molecule-based assay.

Alternatively, according to the present invention the nucleic acids can be used for the rational design of active substances. Preferably the rational design of active substances is the design of a pharmaceutical active substance candidate. Starting from the three-dimensional structure of the target molecule, which is normally determined by methods such as X-ray structure analysis or nuclear magnetic resonance spectroscopy (NMR), computer programs are used to search through data banks containing structures of a large number of different chemical compounds. The selection is carried out by computer. The selected compounds are in addition tested in the laboratory.

The rational design of active substances can take as its starting point any of the nucleic acids according to the present invention, and comprises a structure, in particular a three-dimensional structure, which is similar to the structure of the nucleic acid(s) according to the invention or is identical to that part of the structure of the nucleic acid(s) according to the invention that mediates the binding to HMG proteins. In any case, such a structure also exhibits the same or at least a similar binding behaviour to the nucleic acid(s) according to the invention. In either a further step or as an alternative step, in the rational design of active substances the preferably three-dimensional structure of those parts of the nucleic acids binding to HMG proteins is imitated by chemical groups, which are preferably different to nucleotides and nucleic acids. By means of this imitation, also termed mimicry, a compound can be constructed which is different from the nucleic acid or the nucleic acids which was/were used as starting materials for the rational design of the active substance. Such a compound or active substance is preferably a small molecule or a peptide.

In the case of screening libraries of compounds using competitive tests which are known to those skilled in the art in the field, suitable HMG analogues, HMG agonists and HMG antagonists can be found. Such competitive assays can be designed as follows. The nucleic acid according to the invention, preferably a spiegelmer, i.e. a L-nucleic acid binding the target molecule, is coupled to a preferably solid phase. In order to identify HMG analogues, a labelled HMG protein is added to the test system. Alternatively, the HMG protein could also be coupled to a solid phase and the nucleic acid according to the invention could be labelled. A potential analogue or a potential agonist or antagonist would compete with the HMG molecules which bind to the spiegelmer, which would result in a decrease in the signal received from the corresponding label. The screening for agonists or antagonists can include the use of a cell culture test system which is known to those skilled in the art in the field.

In a further aspect the nucleic acids according to the invention can, on account of their characteristic binding behaviour to HMG protein, be used for target (target molecule) validation. The nucleic acids according to the invention can be used in an ex vivo organ model in order to study the function of HMG protein. In principle there exist ex vivo models in which HMG agonists/antagonists can be tested.

A kit according to the present invention can comprise at least one or more of the nucleic acids according to the invention. In addition the kit can include at least one or more positive or negative controls. HMG protein against which the nucleic acid according to the invention has been screened, or to which this binds, preferably in liquid form, can be used as positive control. As negative control there can be used inter alia a peptide that behaves as regards its biophysical properties similarly to HMG protein, but which is not recognised by the nucleic acids according to the invention, or a peptide can be used having the same amino acid composition but a different sequence to HMG protein.

Furthermore the kit can include one or more buffers. The various constituents can be present in the kit in dry or lyophilised form, or dissolved in a liquid. The kit can include one or more containers, which in turn can contain one or more of the constituents of the kit. Preferably the vessels contain reaction batches, such as are necessary for a single execution of an experiment using one or more constituents of the kit.

It will be acknowledged that, unless stated to the contrary, the sequences listed herein are given in the 5'-3' direction. It will furthermore be seen that the term "the two sections hybridise with one another" is understood herein to mean that the sections can hybridise in vitro on the basis of general base pairing rules, or that the sections hybridise or can hybridise under the conditions of use, but are not necessarily hybridised with one another or are present in hybridised form under the conditions of use.

The various SEQ. ID., the chemical structure of the nucleic acids as disclosed herein and the target molecule HMGA1a/1b as used herein, the actual sequences and the internal references are summarised in the following table.

| Seq. ID | Internal Reference | RNA/Peptide | Sequence |
|---|---|---|---|
| 1 | 132-C3, NOX-h | L-RNA (spiegelmer) | GCUGCUGCAAAUUGACGGGGGCGUGGUUGGGGCGGGUCGAUUGCAGC |
| 2 | 132-B3, NOX-f (48nt) | L-RNA (spiegelmer) | GCUGAAUGAGGAUCGCAGGGGCGUGGCUGGGGUGGGCGACCGUUCAGC |
| 3 | 132-C4 | L-RNA (spiegelmer) | GCUGCGCAAGGAGAGGGGCGCGGUUGGGGAGGCUCUAAGCGCUGCAGC |
| 4 | 132-E2 | L-RNA (spiegelmer) | GCUGGCGCUAUAGGACAGGGGUGCGGUUGGGGCGGUCCGCUGUCAGC |
| 5 | 132-A2 | L-RNA (spiegelmer) | GCUGGAUAGAACGCAGGGGUGCGGUUUGGGGUGGGCGUGAUAUGCAGC |
| 6 | 132-H1, NOX-I | L-RNA (spiegelmer) | GCUGCCGUAAAGAGGGGUGAGGUUGGGGAGGCUUUACGGUUUCAGC |
| 7 | 132-F1 | L-RNA (spiegelmer) | GCUGCAUGCCGCGAUCAGGGGAGCGGUUGGGGCGGGAUCCGGCUCAGC |
| 8 | 132-G2, NOX-g | L-RNA (spiegelmer) | GCUGCGAGGGAGGUAGCGGCUCUGCGCCGUGACGUGGGUGGAUGCAGC |
| 9 | 122-A1, NOX-A | L-RNA (spiegelmer) | GGCUGAUACGUGGGUGGAUAUGGGGCAGUUCCAUGUGGGUGGUUUCAGCC |
| 10 | 122-C1, NOX-B | L-RNA (spiegelmer) | GGCUGAUACGUGGGUGAAUAUGGGGCAGUUCCAUGUGGGUGGUUUCAGCC |
| 11 | 122-B2 | L-RNA (spiegelmer) | GGCUGAUACGUGGGAGGAAAGGUGUAACUACCUGUGGGAGGUUUCAGCC |
| 12 | 122-E2, NOX-C | L-RNA (spiegelmer) | GGCUGGCACUCGCAGGGGUGAAGUGAUGAUUGGGGUGGGCGAGACCAGCC |
| 13 | 122-G2, NOX-E | L-RNA (spiegelmer) | GGCUGCCGAGUGGUUGGGUGGUGUAAGGGAGGUGGAAUCCGCGGGCAGCC |
| 14 | 122-B4, NOX-D | L-RNA (spiegelmer) | GGCUGUUCGUGGGAGGAAGGCUCUUGGAUAGAGUCGUGGGUGGUUCAGCC |

| Seq. ID | Internal Reference | RNA/Peptide | Sequence |
|---|---|---|---|
| 15 | 132-B3 32nt, NOX-f 32nt | L-RNA (spiegelmer) | GGAUCGCAGGGGCGUGGCUGGGGUGGGCGACC |
| 16 | 132-B3 33nt, NOX-f 33nt | L-RNA (spiegelmer) | GGAUCGCAGGGGCGUGGCUGGGGUGGGCGAUCC |
| 17 | HMGA1a/b target molecule domain, Biotinyl-D-HMGA1a/b-21 mer | D-peptide | Biotin-EPSEVPTPKRPRGRPKGSKNK |
| 18 | HMGA1a (human) | L-peptide | (M)SESSSKSSQPLASKQEKDGTEKRGRGRPRKQPPVSPGTALVGSQKEPSEVPTPKRPRGRPKGSKNKGAAKTRKTTTTPGRKPRGRPKKLEKEEEEGISQESSEEEQ |
| 19 | HMGA1b (human) | L-peptide | (M)SESSSKSSQPLASKQEKDGTEKRGRGRPRKQPPKEPSEVPTPKRPRGRPKGSKNKGAAKTRKTTTTPGRKPRGRPKK-LEKEEEEGISQESSEEEQ |
| 20 | HMGA2 human | L-peptide | (M)SARGEGAGQPSTSAQGQPAAPAPQKRGRGRPRKQQQEPTGEPSPKRPRGRPKGSKNKSPSKAAQKKAEATGEKRPRGRPRKWPQQVVQKKPAQEETEETSSQESAEED |
| 21 50 | bio-dsDNA (AT hook) | D-DNA | 5'biotin-TCGAAAAAGCAAAAAAAAAAAAAAAAACTGGC) and 5'GCCAGTTTTTTTTTTTTTTTTTGCTTTTTT |
| 22 | NOX-A-3'PEG, NOX-A-3'PEG2000, NOX-A-2 kDa PEG, NOX-A PEG | L-RNA | GGCUGAUACGUGGGUGGAUAUGGGGCAGUUCCAUGUGGGUGGUUUCAGCC-2 kDa-PEG |
| 23 | INVERSE-3'-PEG INV 3'-PEG | L-RNA | CCGACUUUGGUGGGUGUACCUUGACGGGGUAUAGGUGGGUGCAUAGUCGG-2 kDa-PEG |
| 24 | 5'-biotin-NOX-A | L-RNA | Biotin-GGCUGAUACGUGGGUGGAUAUGGGGCAGUUCCAUGUGGGUGGUUUCAGCC |
| 25 | 5'-biotin-NOX-A inverse | L-RNA | Biotin-CCGACUUUGGUGGGUGUACCUUGACGGGGUAUAGGUGGGUGCAUAGUCGG |
| 26 | INVERSE | L-RNA | CCGACUUUGGUGGGUGUACCUUGACGGGGUAUAGGUGGGUGCAUAGUCGG |
| 27 | POC-3'-PEG | L-RNA | UAAGGAAACUCGGUCUGAUGCGGUAGCGCUGUGCAGAGCU-2 kDa-PEG |
| 28 | Capture probe NOX-A | L-RNA | CCCATATCCACCCACGTATCAGCCTTTTTTTT-NH$_2$ |
| 29 | Detector probe NOX-A | L-RNA | Biotin-TTTTTTTTGGCTGAAACCACCCACATGG |
| 30 | Capture probe POC | L-RNA | NH$_2$(C7)-TTTTTTTTTAGCTCTGCACAGCGCT |
| 31 | Detector probe POC | L-RNA | CCGCATCAGACCGAGTTTCCTTATTTTTTTT-Biotin |
| 32 | HMG_fwd1 Primer | D-DNA | TCGACACCATGGGTGAGTC |
| 33 | HMG_rev1 Primer | D-DNA | GTCTAGAAAGCTTCCCAACTG |
| 34 | 132-C3, NOX-h | D-RNA (aptamer) | GCUGCUGCAAAUUGACGGGGGCGUGGUUGGGGCGGGUCGAUUGCAGC |
| 35 | 132-B3, NOX-f (48nt) | D-RNA (aptamer) | GCUGAAUGAGGAUCGCAGGGGCGUGGCUGGGGUGGGCGACCGUUCAGC |
| 36 | 132-C4 | D-RNA (aptamer) | GCUGCGCAAGGAGAGGGCGCGGUUGGGGAGGCUCUAAGCGCUGCAGC |
| 37 | 132-E2 | D-RNA (aptamer) | GCUGGCGCUAUAGGACAGGGGUGCGGUUGGGGCGGUCCGCUGUCAGC |
| 38 | 132-A2 | D-RNA (aptamer) | GCUGGAUAGAACGCAGGGGUGCGGUUUGGGGUGGGCGUGAUAUGCAGC |
| 39 | 132-H1, NOX-i | D-RNA (aptamer) | GCUGCCGUAAAGAGGGGUGAGGUUGGGGAGGCUUUACGGUUUCAGC |
| 40 | 132-F1 | D-RNA (aptamer) | GCUGCAUGCCGCGAUCAGGGGAGCGGUUGGGGCGGGAUCCGGCUCAGC |

-continued

| Seq. ID | Internal Reference | RNA/Peptide | Sequence |
|---|---|---|---|
| 41 | 132-G2, NOX-g | D-RNA (aptamer) | GCUGCGAGGGAGGUAGCGGCUCUGCGCCGUGACGUGGGUGGAUGCAGC |
| 42 | 122-A1 , NOX-A | D-RNA (aptamer) | GGCUGAUACGUGGGUGGAUAUGGGGCAGUUCCAUGUGGGUGGUUUCAGCC |
| 43 | 122-C1, NOX-B | D-RNA (aptamer) | GGCUGAUACGUGGGUGAAUAUGGGGCAGUUCCAUGUGGGUGGUUUCAGCC |
| 44 | 122-B2 | D-RNA (aptamer) | GGCUGAUACGUGGGAGGAAAGGUGUAACUACCUGUGGGAGGUUUCAGCC |
| 45 | 122-E2, NOX-C | D-RNA (aptamer) | GGCUGGCACUCGCAGGGGUGAAGUGAUGAUUGGGGUGGGCGAGACCAGCC |
| 46 | 122-G2, NOX-E | D-RNA (aptamer) | GGCUGCCGAGUGGUUGGGUGGUGUAAGGGAGGUGGAAUCCGCGGGCAGCC |
| 47 | 122-B4, NOX-D | D-RNA (aptamer) | GGCUGUUCGUGGGAGGAAGGCUCUUGGAUAGAGUCGUGGGUGGUUCAGCC |
| 48 | 132-B3 32nt, NOX-f 32nt | D-RNA (aptamer) | GGAUCGCAGGGGCGUGGCUGGGGUGGGCGACC |
| 49 | 132-B3 33nt, NOX-f 33nt | D-RNA (aptamer) | GGAUCGCAGGGGCGUGGCUGGGGUGGGCGAUCC |

It is within the scope of the present invention that, if no sequences are explicitly given for the individual sections of the nucleic acids according to the invention, these can be freely chosen according to the technical teaching disclosed herein, i.e. can be chosen so that they exhibit the necessary binding behaviour to the respective target molecule and/or are able to form the structures, in particular secondary structures, described herein.

Furthermore, it is within the scope of preferred embodiments of the present invention that in the case where, in sequences that are identified as RNA sequences, T is given instead of U, then T shall denote U.

The present invention is described in more detail hereinafter with the aid of the following Figures and Examples, which disclose further features, embodiments and advantages. In this connection:

FIG. 1A shows aptamers generated by in vitro selection against D-21AS-HMGA1a/b, which bind the 21AS-HMGA1a/b domain;

FIG. 1B is a representation of the identified, repeatedly occurring sequence regions of the aptamers generated by in vitro selection against D-21AS-HMGA1a/b, which bind the 21AS-HMGA1a/b domain;

FIG. 2 is a sequence comparison of HMGA1a/b and HMGA2;

FIG. 3 is a shortening of HMGA1a/b-binding aptamer NOX-f;

FIG. 4 shows the binding properties of shortened HMGA1a/b-binding aptamer NOX-f;

Figure 22:
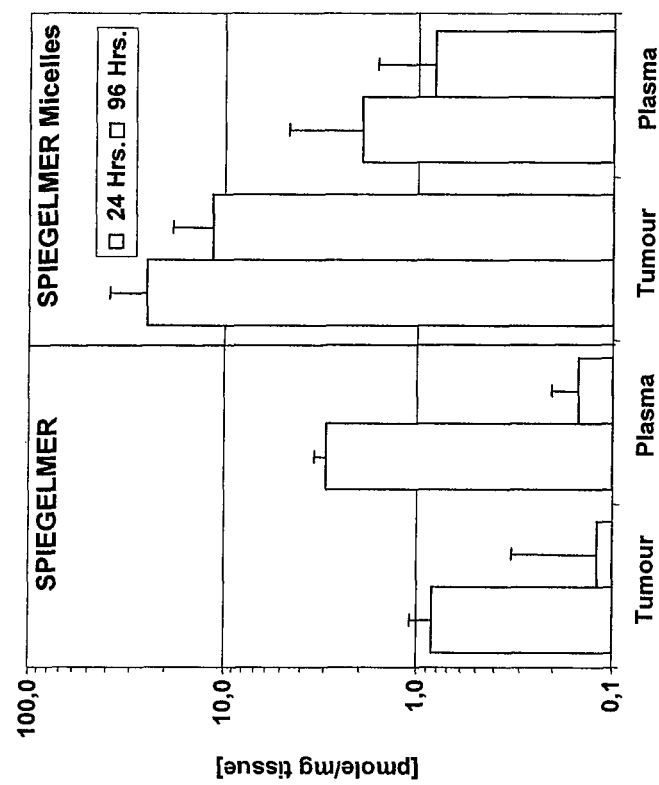

FIG. 5 shows a competition assay for measuring the binding of HMGA to the double-strand natural target DNA in the multi-well plate assay; the binding of the spiegelmer competes with the binding of the recombinant HMGA1b to the biotinylated dsDNA (AT hook motif). The detection of the bound HMGA1b is carried out through the His-Tag via nickel HRP, which converts a substrate into a fluorescing signal;

FIG. 6 shows a comparison of spiegelmer NOX-A and spiegelmer NOX-f (48 nt; 33 nt) in the competitive multi-well plate assay; in the plate assay, spiegelmer NOX-A as well as spiegelmer NOX-f and its shortened variant spiegelmer NOX-f33 prevent the binding of recombinant HMGA1b to its naturally occurring binding partner in the low nanomolar range.

FIG. 7 shows the activity of 2kDa-PEG-coupled spiegelmer NOX-A as well as non-functional control spiegelmer in the competitive multi-well plate assay; the PEGylated spiegelmer NOX-A competes with the binding of recombinant HMGA1b to the AT hook motif of the dsDNA with an IC50 of 15 nM; the inverse control spiegelmer of NOX-A shows at high spiegelmer concentrations a non-specific interaction with HMGA1b;

FIG. 8 shows a western blot; detection of immobilised HMGA1b by biotinylated spiegelmer; recombinant HMGA1b migrates in the electrophoretic field like a 20kDa large protein and can be recognised at low concentration (3 nM) by the biotinylated spiegelmer (here with the example of NOX-A); an inverse control spiegelmer could not recognise HGMGA1b;

FIG. 9 shows the activity of free and PEGylated spiegelmer NOX-A in the competitive multi-well plate assay;

FIG. 10 is an investigation of the packing of PEGylated spiegelmer in micelles in the "RiboGreen exclusion assay";

FIG. 11 shows the stability of PEI spiegelmer micelles in the "RiboGreen exclusion assay";

FIG. 12 shows the efficient uptake of spiegelmer packed in PEI micelles, in particular a comparison of the transfection of "naked" spiegelmer compared to spiegelmers packed in micelles, with the example of the spiegelmer NOX-A-3'PEG2kDa.; the cells which have been transfected with spiegelmer micelles exhibited at a lower setting of the camera sensitivity (camera gain) a stronger fluorescence in the cytosol compared with cells that had been incubated only with pure spiegelmer; the efficiency with both transfection methods is >95%;

FIG. 13 shows the release of spiegelmer from the endosomal compartment; spiegelmer micelles exhibited a significantly higher fluorescence compared to pure spiegelmer; spiegelmer micelles exhibited a point-like, perinuclear, and also cytoplasmic distribution pattern; the point-like distribution indicates a localisation in endosomal compartments; the diffuse distribution in the cytosol and on the plasma membrane indicates spiegelmer released from endosomes;

FIG. 14 is a proliferation assay with "naked" spiegelmer; dose-dependent inhibition of the proliferation of MCF-7 cells at high spiegelmer concentrations after 2 days in the cell culture medium (quantification via resazurin);

FIG. 15 shows the proliferation of H1299 cells ("non-small cell lung cancer") after treatment with PEI packed NOX-A-2kDa PEG; inhibition of the proliferation of H-1299 cells at 1 μM spiegelmer, applied as PEI-spiegelmer micelles (N/P 2.5); NOX-A showed a slight inhibition of the proliferation compared to the control spiegelmer;

FIG. 16 shows the inhibition of the HMGA1a/b-induced cdc25a gene expression, detected by quantitative RT-PCR; determination of the specific inhibition of the cdc25a mRNA expression in H-1299 cells by 1 μM NOX-A spiegelmer micelles (N/P 2.5) by means of RT-PCR;

FIG. 17 shows the dose-dependent inhibition of the cdc25a mRNA expression by spiegelmer NOX-A; quantification of the dose-dependent inhibition of the cdc25a mRNA expression in H1299 cells by means of RT-PCR; NOX-A spiegelmer micelles (N/P 2.5) showed starting at 250 nM a specific inhibition of the cdc25a mRNA expression; at a concentration >4 μM a non-specific effect of the control spiegelmer was found, as well as toxic effects due to the polyethyleneimine (PEI) at >10 μM (data not shown);

FIG. 18 shows the inhibition of the tumour growth in the xenograft model in naked mice by the spiegelmer NOX-A; inhibition of the tumour growth after subcutaneous injection of PSN-1 cells by 2 mg/kg spiegelmer micelles (N/P 2.5). Spiegelmer NOX-A produced a significant reduction in tumour growth;

FIG. 19 shows the statistical analysis of the data from the xenograft experiment; inhibition of the tumour growth after subcutaneous injection of PSN-1 cells by 2 mg/kg spiegelmer micelles (N/P 2.5); end point analysis and representation as box-and-whisker plot. NOX-A produced a highly significant reduction of the tumour growth (p=0.0098 compared to PBS and p=0.022 compared to inverse control spiegelmer);

FIG. 20 shows the tissue distribution of spiegelmer NOX-A in the xenograft experiment; quantitative analysis of the distribution of spiegelmer NOX-A in the plasma and tissues; a high concentration of spiegelmer NOX-A could be detected in the tumour tissue, compared to the other tissues and plasma.

FIG. 21 shows tissue distribution of spiegelmer packed in micelles and unpacked spiegelmer, 24 and 96 hours after the last injection in the xenograft experiment; quantitative analysis of the distribution of non-functional spiegelmers in plasma and tissues; in the tumour tissue a significantly raised concentration of spiegelmer could be detected in the case of a spiegelmer packed in micelles compared to the other tissues and plasma, after 24 hours and 96 hours.

FIG. 22: shows distribution of spiegelmer packed in micelles and unpacked spiegelmer in plasma and in the tumour 24 and 96 hours after the last injection in the xenograft experiment; quantitative analysis of the distribution of a non-functional spiegelmer in plasma and tumour; in the tumour tissue a significantly raised concentration of spiegelmer could be detected in the case of a spiegelmer packed in micelles compared to the unpacked spiegelmer, after 24 hours and 96 hours.

EXAMPLE 1

HMGA1a/b-Binding Spiegelmers 1.1 HMGA1a/b-Binding Sequences

The HMGA1a/b-binding RNA spiegelmers were generated by in vitro selection against D-21AS-HMGA1a/b and subsequent shortening steps. The generated aptamers, which bind the 21AS-HMGA1a/b domain, are shown in FIG. 1A.

1.1.1 Ranking and Aptamer Level

The different clones (see FIG. 1A) were prepared as aptamers (D-RNA) by means of standard phosphoramidite synthesis and were radioactively labelled at the 5' end by kinasing (see below). The clones were then analysed as regards their affinity and activity by means of equilibrium binding assay at two concentrations of D-bio-21aa HMGA1a/b.

Radioactive Labelling by Kinasing:

| Substance | [final] |
|---|---|
| RNA | 5 μM |
| T4 forward reaction buffer (Invitrogen) | 1x |
| T4 polynucleotide kinase (Invitrogen) | 10 U/10 $\mu l_{Reaction\ batch}$ |
| [γ-$^{32}$P]-ATP | 1 μl/10 $\mu l_{Reaction\ batch}$ |

The reaction ran for 1 hour at 37° C. and was then stopped by heating (10 minutes at 65° C.). The separation of radioactive nucleotides from labelled oligonucleotides was carried out by an analytical polyacrylamide gel electrophoresis (PAGE) (see hereinafter). A "crush-and-soak" gel elution was then carried out with ammonium acetate and precipitation with ethanol (see hereinafter). The amount of purified RNA was estimated from the radioactivity of the pellets (after the precipitation) compared to the radioactivity of the cut-out strip.

Polyacrylamide Gel Electrophoresis (PAGE)

For the preparative purification of oligonucleotides, ½ to 2 volumes of concentrated sample buffer for denaturing PAGE were added to the reaction batches. In addition large-scale standards were prepared as necessary (each 250 pmole) and taken up in sample buffer. The batches were denatured for 5 minutes at 95° C. and cooled on ice. A preparative, denaturing 7% or 10% PAA gel (200×200×1.5 mm) was preheated (ca. 1 hour) by applying a maximum voltage of 600 V at 40-50 W. After rinsing the cups with 1×TBE the samples were plotted. After completion of the separation (50 minutes at 50 W) the gel was placed on a fluorescing thin-layer chromatography plate protected by transparent film (dye 60F$_{254}$). The bands were visualised as shadows ("UV shadowing") by means of UV light (254 nm) and were cut out with a scalpel. A "crush-and-soak" gel elution with ammonium acetate was then performed.

"Crush-and-Soak" Gel Elution

To elute oligonucleotides from PAA gels, after comminuting the cut-out PAA gel strips 500 μl of ammonium acetate (2 M) was added using a pipette tip or a spatula. The "crush-and-soak" elution was carried out 2×1.5 hours at 68° C. in a thermoshaker (1000 rpm). The supernatants were freed from gel residues by "Ultrafree-MC" small columns (Millipore/Amicon, Schwalbach, Germany) in a table centrifuge (16, 100×g). The RNA eluted in this way was then desalted by precipitation with ethanol.

Ethanol Precipitation

For the ethanol precipitation 1-2 μl of glycogen were used as precipitation auxiliary. After adding 2.5 volumes of absolute ethanol and vortexing, the oligonucleotides were precipitated for 30 minutes at −80° C. and centrifuged off for 30 minutes at 16,100 g, 4° C. The pellet was washed once with 70% ethanol and centrifuged for 5 minutes at 16,100 g, 4° C.

Recording of Binding Isotherms in the Equilibrium Binding assay 2 pmole of each of the 5' radioactively labelled aptamers were complexed in biotinyl-D-HMGA1a/b-21mer (EPS-EVPTPKRPRGRPKGSKNK [Seq. ID. 17]; see FIG. 2), produced by Bachem (Weil am Rhein, Germany). Solutions in the concentration range 1-3000 nM (or for the two-point measurement with 300 nM and 30 nM or 100 nM and 10 nM peptide) were incubated for 1 hour at 37° C. in selection buffer (10 mM Tris HCl pH7.4, 5 mM KCl, 0.8 mM MgCl$_2$, 0.1% Tween). A solution without biotinylated D-HMGA1a/b-21mer served as background control. The peptide and complexes were then immobilised within 30 minutes at 37° C. with 10 µl of streptavidin UltraLink gel. The radioactivity of the suspension was measured. The supernatant was removed. The matrix was then washed once with 100 µl of selection buffer and then precipitated with selection buffer. By measuring the radioactivity the aptamer fraction present together with biotinyl-D-HMGA1a/b-21mer in the complex was determined for each peptide concentration. The dissociation constants of the active species and the proportion of active molecules were determined by graphical plotting and fit (GraFit, Version 4.0.10, Erithacus Software).

Results

For all clones synthesised as aptamers (D-RNA) a dissociation constant for the binding to the 21 amino acid-long D fragment of HMGA1a/b (Biotinyl-D-HMGA1a/b-21mer) of 8-22 nM was determined in the equilibrium binding assay (FIG. 1A).

1.1.2 Shortening in Example 132-B3

All selection candidates exhibited a repetitively occurring sequence motif GGGCG or GGGUG or GGGAG, which is stabilised at the 5' end and at the 3' end by a helix/stem motif (FIG. 3).

An analysis of the probable structure and precipitation of the RNA aptamers according to Zuker (Nucleic Acids Res. 2003 Jul. 1; 31(13):3406-15) showed that the predetermined stem/helix structure had lengthened in some cases (132-C3, 132-33, 132-C4, 132-E2, 132-A2, 132-H1, 132-F1, 122-G2, 122-E2, see FIG. 1A). This stem-Helix structure formed the basis for the further shortening of these candidates. This further shortening of the candidates was carried out by identifying and stabilising the minimal binding motif by precipitation analysis followed by deletion analysis of the synthetic D-RNAs with respect to the binding to the HMGA1a/b fragment. These binding properties were determined by equilibrium binding assay. FIG. 3 shows by way of example in the candidate NOX-f (132-B3) the shortening of the aptamer on the basis of the stabilising stem structure, which can be found in lengthened form in the candidates 132-C3, 132-B3, 132-C4, 132-E2, 132-A2, 132-H1, 132-F1, 122-G2, 122-E2 (see FIG. 1A). A shortening to a 32 nucleotide-long aptamer variant of NOX-f with a 6 nucleotide-long stem (NOX-f 32 nt) did not lead to any loss of the binding properties to the 21aa HMGA1a/b fragment (FIGS. 3 and 4). The artificial insertion of an adenosine at the third position of the 5'-position stem led to a theoretical formation of a 7 nucleotide-long stem without a looped-out region and served to complete the stem in the 3' region (NOX-f 33 nt, FIGS. 3 and 4). The measurement of the binding properties (affinity and activity) by means of equilibrium binding assay on the 21 amino acid-long domain of HMGA1a/b was not influenced by these changes.

The sequences 132-G2, 122-A1, 122-C1, 122-B2 and 122-B4 have on the other hand at the 5' end and 3' end of the repetitively occurring sequence motif (GGGCG or GGGUG or GGGAG) a significantly shorter stem structure. A shortening of the stem structure led to a binding loss. A possible shortening of the central region, which is longer for these sequences, between the repetitive sequence motif (GGGCG or GGGUG or GGGAG) was not carried out.

The Seq. IDs of the aptamer sequences of the HMGA-binding nucleic acids disclosed herein are as follows:

| Seq. ID | Internal Reference | RNA/Peptide |
|---------|-------------------|-------------|
| 34 | 132-C3, NOX-h | D-RNA (aptamer) |
| 35 | 132-B3, NOX-f (48 nt) | D-RNA (aptamer) |
| 36 | 132-C4 | D-RNA (aptamer) |
| 37 | 132-E2 | D-RNA (aptamer) |
| 38 | 132-A2 | D-RNA (aptamer) |
| 39 | 132-H1, NOX-i | D-RNA (aptamer) |
| 40 | 132-F1 | D-RNA (aptamer) |
| 41 | 132-G2, NOX-g | D-RNA (aptamer) |
| 42 | 122-A1, NOX-A | D-RNA (aptamer) |
| 43 | 122-C1, NOX-B | D-RNA (aptamer) |
| 44 | 122-B2 | D-RNA (aptamer) |
| 45 | 122-E2, NOX-C | D-RNA (aptamer) |
| 46 | 122-G2, NOX-E | D-RNA (aptamer) |
| 47 | 122-B4, NOX-D | D-RNA (aptamer) |
| 48 | 132-B3 32 nt, NOX-f 32 nt | D-RNA (aptamer) |
| 49 | 132-B3 33 nt, NOX-f 33 nt | D-RNA (aptamer) |

As has already been discussed herein and is known to those skilled in the art in this field the enantiomer, consisting of L-nucleotides, of an aptamer, i.e. of a D-nucleic acid which was generated against a D-peptide, binds to the mirror-image enantiomer of the D-peptide, i.e. the naturally occurring L-peptide. This L-nucleic acid is herein also referred to as spiegelmer and otherwise exhibits in principle the same binding properties as the aptamer.

1.2 Characteristic Properties of HMGA/b-Binding Spiegelmers 1.2.1 Repetitive Sequence Elements: Box A1 and Box A2

A repetitive sequence element of the sequence GGGCG or GGGUG or GGGAG is characteristic of all spiegelmers that bind to HMGA1a/b. This sequence element appears twice in HMGA1a/b-binding spiegelmers (FIGS. 1A and 1B). The sequence element lying closer to the 5' end of the spiegelmers is herein referred to as Box A1. The sequence element lying closer to the 3' end of the spiegelmers is on the other hand referred to herein as Box A2. Box A1 and Box A2 and their mutual arrangement probably represent the decisive feature of HMGA1a/b-binding spiegelmers.

1.2.2 Sequence Section Between Box A1 and Box A2

Between Box A1 and Box A2 there is either a sequence section with a length of six to seven nucleic acids or 12 to 22 nucleotides (FIGS. 1A and 1B). Since these sequence sections differ not only in their length, they are discussed separately.

Case 1: Sequence Section Comprises Six to Seven Nucleotides

If the sequence section lying between Box A1 and Box A2 has a length of six nucleotides, then the sequence section exhibits the sequence UGGUUG, UGGCUG, CGGUUG, AGGUUG or GUGUAA. An insertion of one nucleotide (uracil) into the sequence CGGUUG, which leads to the sequence CGGUUUG, has neither a negative nor a positive influence on the binding properties of the spiegelmers.

Case 2: Sequence Section Comprises 12 to 22 Nucleotides

If the sequence section lying between Box A1 and Box A2 has a length of 12 to 22 nucleotides, then this sequence section comprises two sequence regions of equal length, which can possibly hybridise with one another (Helix C). The hybridisation is in this case effected by in each case three to six nucleotides. Three to five unpaired nucleotides are located between the nucleotides forming the Helix C. One to three nucleotides are present unpaired between the 3' end of Box A1 and the 5' end of Helix C. One to five nucleotides can be present unpaired between the 3' end of Helix C and the 5' end of Box A2.

1.2.3 Helical Structure at the 5' End and 3' End of the Spiegelmers

All HMGA1a/b-binding spiegelmers are characterised at their 5' and 3' ends by sequence sections which can hybridise with one another (Helix A1 and Helix A2, (FIGS. 1A and 1B). The number of nucleotides hybridising with one another in each case can vary from four to eight. In this connection, this presumably double-strand region can extend to the 5' end of Box A1 and the 3' end of Box A2. Should this not be the case, then Box A1 and Box A2 can be flanked by nucleotides that additionally hybridise with one another (Helix B1 and Helix B2). This can involve regions of in each case four to eight nucleotides (FIGS. 1A and 1B).

Within the scope of the invention forming the basis of the present application, various classes of nucleic acids and in particular L-nucleic acids which bind to the target molecule have been identified. The following illustration and description of these classes, which are herein also termed cases, is to this extent an integral part of the present invention. For each class their principal structure and exemplary L-nucleic acids for this class are specified hereinafter using the respective abbreviations of the L-nucleic acids.

Case 1: 132-C3, 132-B3, 132-C4, 132-E2, 132-A2, 132-H1, 132-F1, 122-G2, 132-B3 32nt, 132-B3 33nt Helix-A1-$N_x$-Helix B1-$N_6N_7$-Box A1-$N_1N_2GN_8N_3N_4N_5$-Box A2-G-$N_y$-Helix B2-$N_z$-Helix A2 (Case 1A)    or Helix-A1-$N_x$-Helix B1-$N_6N_7$-Box A1-$N_1N_2GN_8N_3N_4N_5$-Box A2-Helix B2-$N_z$-Helix A2 (Case 1B)

$N_1$=U, C, A, G;
$N_2$=G, U;
$N_3$=U, C;
$N_4$=U, A;
$N_5$=G, A;
$N_6$=G, A, U;
$N_7$=G, U;
$N_8$=U or no nucleotide;
$N_x$=zero to five nucleotides;
$N_y$=zero or six nucleotides;
$N_z$=zero to six nucleotides;

Box A1 = Box A2 = GGGCG or GGGUG or GGGAG;

Helix A1 and Helix A2=in each case four to eight nucleotides, which completely or partly hybridise with one another, in which the sum of the in each case mutually hybridising nucleotides of Helix A1 and Helix A2 and Helix B1 and Helix B2 is 10 to 12 nucleotides;

Helix B1 and Helix B2=in each case four to eight nucleotides, which hybridise with one another, in which the sum of the in each case mutually hybridising nucleotides of Helix A1 and Helix A2 and Helix B1 and Helix B2 is 10 to 12 nucleotides.

The molecules are active also after the shortening at the 5' end and at the 3' end. After the removal of the Helix A1 and A2 as well as the regions $N_6N_7$ and $GN_y$, the shortened molecules retain their binding properties. This was demonstrated for the shortened variants 132-B3 32nt (NOX-f 32nt) and 132-B3 33nt (NOX-f 33nt) (see FIGS. 3 and 4).

Case 2A: 132-G2, 122-A1, 122-C1, 122-B2, 122-B4

Helix A1-$N_a$-Box A1-$N_b$-Helix C1-$N_c$-Helix C2-$N_d$-Box A2-G-$N_e$-Helix A2

$N_a$=one to five nucleotides
$N_b$=three nucleotides
$N_c$=three to five nucleotides
$N_d$=two to five nucleotides
$N_e$=one to two nucleotides, preferably A or UU Box A1 = Box A2 = GGGCG or GGGUG or GGGAG Helix A1 and Helix A2=in each case five to six nucleotides, which completely or partly hybridise with one another, Helix C1 und Helix C2

=in each case five to six nucleotides, which hybridise with one another.

Case 2B: 122-E2

Helix A1-$N_f$-Helix B1-$N_f$-Box A1-A-Helix C1-$N_c$-Helix C2-G-Box A2-G-Helix B2-A-Helix A2

$N_i$=two nucleotides, preferably CA
$N_j$=two nucleotides, preferably AG
$N_c$=four nucleotides, preferably GAUG Box A1 = Box A2 = GGGCG or GGGUG or GGGAG Helix A1 and Helix A2=in each case six nucleotides, which hybridise with one another, Helix B1 and Helix B2=in each case five nucleotides, which hybridise with one another, Helix C1 and Helix C2

=in each case three nucleotides, which hybridise with one another.

EXAMPLE 2

Domain Approach 2.1 Determination of the Interaction of HMGA1a/b Spiegelmers and Recombinant HMGA1b in the Competition Assay Execution/Method Cloning of His6-Labelled HMGA1b The BD-Freedom™ ORF clone GH00552L1.0 (high mobility group AT hook1) with the sequence coding for HMGA1b was purchased from BioCat Heidelberg. The sequence had already been changed therein so that the stop codon is converted into a codon coding for leucine, in order to permit C-terminal fusions. The sequence of the clone corresponds generally to the sequence stored in the RefSeq data bank under No. NM002131. The sequence coding for HMGA1b was amplified by means of a standard PCR with the primers HMG_fwd1 (TCGACACCATGGGTGAGTC, Seq. ID 34) and HMG rev1 (GTCTAGAAAGCTTCCCAACTG, Seq. ID 35). In this connection the base after ATG was changed from A to G, in order thereby to introduce a NcoI interface. The PCR product was cleaved according to the manufacturer's instructions with the restriction enzymes NcoI and HindIII (both from NEB, Frankfurt am Main, Germany) and purified via an agarose gel. The vector pHO2d (Fasshauer et al. (1997) J. Biol. Chem. 272:28036-28041)) was similarly cleaved with NcoI and HindIII and purified via an agarose gel. The Vector pHO2d permits the expression of a protein fused to the C-terminal end with a sequence of six histidine residues (His6-tag), under the control of a T7-promotor (Fasshauer et al., 1997, JBC 272:28036).

The purified and cleaved PCR product was ligated into the prepared vector overnight at 15° C. with the aid of a T4 ligase, corresponding to the manufacturer's instructions (MBI Fermentas, St. Leon-Roth, Germany). Bacteria of strain DH5☐ were transformed with the ligation product. The correctness of the plasmids from obtained colonies was checked by sequencing. The fusion protein HMGA1b-His6 coded by pHO2d/HMGA1b has, compared to the natural HMGA1b protein, a glycine (G) instead of serine (S) at position 2, and after the C-terminal glutamine (Q) a leucine (L) (see above), followed by five further amino acids (G S L N S) (coded by the vector), to which the six histidines (H) are joined.

Expression and Purification of HMG1b-His6

For the expression of the fusion protein bacteria of strain BL21 were transformed with the plasmid pHO2d/HMGA1b. The expression of the fusion protein was induced with isopropylthio-β-D-galactoside (IPTG). After 4 hours the bacteria were centrifuged off for 15 minutes at 10,000×g and the pellet was stored at −20° C. until further use.

For the extraction of the fusion protein 25 ml of extraction buffer (1% n-octyl-β,D-thioglucopyranoside (OTG) in 50 mM $Na_xPO_4$ buffer, pH 8.0, 250 mM NaCl, 10 mM imidazole and MiniProtease inhibitor tablets (Roche, Mannheim, Germany) (5 hrs/50 ml)) were added to a frozen bacteria pellet from 500 ml of culture, followed by 5 µl of benzonase (gradel; MERCK, Darmstadt, Germany), homogenised by pipetting and pipetting off, and incubated for 5 min at RT. This was followed by centrifugation for 15 mins at 10,000×g (RT). The supernatant was filtered through a fluted filter and then added to a HIS-SELECT column (HIS-SELECT Cartridge, Sigma, Deisenhofen, Germany) equilibrated with wash buffer (50 mM $Na_xPO_4$ buffer, pH 8.0, 250 mM NaCl, 10 mM imidazole, all from MERCK, Darmstadt, Germany). After washing the column with 10-15 ml of wash buffer the fusion protein was eluted with elution buffer (250 mM imidazole in wash buffer) in 0.5-1 ml size fractions. Protein-containing fractions were checked for purity by means of gel electrophoresis (16% polyacrylamide gel according to Schäger & Jagow, 1987, Anal. Biochem. 166:368-379). Fractions with fusion protein were purified, if necessary dialysed using a suitable buffer, and after protein determination were tested again for purity. The purified fusion protein was stored in aliquots at −20° C.

Determination of the Interaction of HMGA1a/b Spiegelmers and HMGA1b-His6

A test based on the 96-well format was used for a more detailed analysis of the affinity of the HMGA1a/b-spiegelmers for HMGA1b. In this test the binding of the HMGA1a/b spiegelmers to HMGA1b-His6 prevents its interaction with a DNA oligonucleotide that has a binding site for HMGA1a/b. This DNA oligonucleotide (dsDNA AT hook) (Fashena et al., 1992) is labelled on one strand with a biotin molecule, via which it can be bound to plates coated with streptavidin. The detection of HMGA1b-His6 bound to DNA is carried out with horseradish peroxidase modified with nickel (Nickel-HRP), which transforms a fluorogenic substrate. In this assay the spiegelmer displaces the recombinant HMGA1b from its natural binding partner. On account of the 1:1:1 stoichiometry of spiegelmer/rHMGA1b/dsDNA AT Hook, a direct prediction can be made regarding the affinity of the spiegelmers for HMGA1b. The principle of the assay is illustrated in FIG. 5.

To carry out this test spiegelmers in various concentrations and HMGA1b-His6 (0.36 µg/ml; ca. 30 nM) in a total volume of 100 µl are incubated for 10 minutes in a tapered floor plate at room temperature while shaking. The incubation solution also contains: 25 mM Tris/HCl, pH 7.0 (Ambion, Austin, Tex., USA), 140 mM KCl (Ambion, Austin, Tex., USA), 12 mM NaCl (Ambion, Austin, Tex., USA), 0.8 mM MgCl2 (Ambion, Austin, Tex., USA), 0.25 mg/ml BSA (Roche, Mannheim, Germany), 1 mM DTT (Invitrogen, Karlsruhe, Germany), 18-20 µg/ml poly(dGdC) (Sigma, Deisenhofen, Germany)), 0.05% Tween 20 (Roche, Mannheim, Germany). 2 µl of biotinylated DNA oligonucleotides dsDNA AT hook (equimolar mixture of 5'biotin-TCGAAAAAAG-CAAAAAAAAAAAAAAAAAACTGGC (34 nt) and 5'GCCAGTTTTTTTTTTTTTTTTTTGCTTTTTT (31 nt); 75 µM in 150 mM NaCl (Ambion, Austin, Tex., USA)) are then added and incubated for a further 10 mins at RT while shaking. The batches are then transferred to a black 96-well plate coated with streptavidin (ReactiBind from Pierce, Bonn, Germany)) and incubated for 30 mins at RT while gently shaking. Following this the wells of the plate are washed three times, each time with 200 µl of TBSTCM (20 mM Tris/HCl, pH 7.6 (Ambion, Austin, Tex., USA); 137 mM NaCl (Ambion, Austin, Tex., USA), 1 mM MgCl2 (Ambion, Austin, Tex., USA), 1 mM CaCl2 (Sigma, Deisenhofen, Germany), 0.05% Tween 20 (Roche, Mannheim, Germany)). 50 µl of a dilute nickel-HRP solution are added to each well (ExpressDetector nickel-HRP, (Medac, Hamburg, Germany) 1:1000 in 10 mg/ml BSA (Roche, Mannheim, Germany) in TBSTCM) and incubated for 1 hour at RT while gently shaking. The wells are then washed again three times with 200 µl TBSTCM each time. 100 µl of the fluorogenic HRP substrate (QuantaBlue, Pierce, Bonn, Germany) are then added to each well and the fluorescence is measured after 15 mins (ex: 340/em:405 nm).

Result

It was shown that the spiegelmers NOX-A (50nt), NOX-f (33nt) and NOX-f (48nt) compete in a concentration-dependent manner with the binding of HMGA1b-His6 to the biotinylated DNA-Oligonucleotide (FIG. 6). A IC50 of ca. 15 nM is found for spiegelmer NOX-A.

In contrast to the active spiegelmer, a control spiegelmer with a inverse sequence to NOX-A showed in a concentration of up 0.5 µM no effect on the binding of HMGA1b-His6 to the DNA oligonucleotide, and non-specific interactions with HMGA1b-His6 occur only at concentrations above 1 µM (FIG. 7).

2.2 Use of Spiegelmers to Detect HMGA1b by Western Blot

Execution/Methods

The recombinantly expressed HMGA1b was separated by gel electrophoresis on a 16% PAA-tricin gel and transferred by means of electroblotting to nitrocellulose membranes. The membrane was then blocked with 5% skimmed milk and 100 nM non-specific spiegelmer in 1×TBST (20 mM Tris/HCl pH 7.6, 137 mM NaCl, 0.1% Tween) for 1 hour and washed three times for 10 minutes with 1×TBST. The detection of the recombinant HMGA1b was carried out with spiegelmer NOX-A biotinylated at the 5' end (5'bioNOX-A). 5'bioNOX-A was diluted in 1×TBST with 1 mM each of calcium and magnesium (TBST+Ca/Mg) and 100 nM non-specific spiegelmer and incubated for 1.5 hours. The blot was then washed three times for 10 minutes with 1×TBST+Ca/Mg and the bound biotinylated spiegelmer was incubated with an anti-biotin antibody in TBST+Ca/Mg for 45 minutes. The blot was then washed five times for 10 minutes with 1×TBST+Ca/Mg and the secondary antibody coupled with horseradish peroxidase (HRP) was detected by means of LumiGLO detection reagent (Cell Signaling Technology).

Result

The binding of a 5'-terminal biotinylated spiegelmer to the recombinantly expressed HMGA1b was demonstrated by means of the aforedescribed process. Similarly to a detection based on antibodies, 5 μg of HMGA1b were detected with 3 nM bio-NOX-A after transfer to a blot membrane. The inverse spiegelmer of NOX-A could not recognise HMGA1b, which confirms the specific binding of NOX-A (FIG. 8).

EXAMPLE 3

PEI-Spiegelmer Formulation 3.1 Principle of the Polyethyleneimine-Mediated Transfection of Spiegelmers The target molecule HMGA1a/b is expressed in the cytosol and finds as transcription factor its natural binding partner, the double-strand DNA in the cell nucleus. The HMGA1a/b-mediated cellular responses should be antagonised by binding of the spiegelmer to HMGA1a/b in the cytosol, and competition of the HMGA1a/b bound by the AT hooks to the DNA in cell nucleus. On account of the negative charge of the plasma membrane DNA and RNA molecule are not readily taken up by passive transport from a cell. One of the approaches to the intracellular transport by nucleic acids is the condensation or packing with charged particles or reagents, resulting in a charge of the overall complex. This complex is easily taken up through endocytosis and thus passes into the cytosol of the cell. Disadvantages of this method are the stability of the DNA/RNA and the release of the nucleic acid from the endosomal compartment. In the cytosol of the cell a lysosome is quickly formed from the constricted endosome by the introduction of proteases or nucleases and by protonation of the compartment. Nucleases digest the nucleic acids there and in addition the nucleic acid is not stable in the acidic medium. The whole complex is rapidly transported again out of the cell by exocytosis and decomposition in the Golgi apparatus, and therefore only a few nucleic acids pass into the cell. One of the preconditions for a suitable transfection system is thus the stabilisation as well as the release of the nucleic acid from the endosome into the cytosol. As regards stability RNA spiegelmers have ideal properties for a transfection of eukaryotic cells, since being unnatural enantiomers they are not cleaved by enzymes.

The selected transfection system is based on the formation of micelles of nucleic acids with branched polyethyleneimine (PEI). The phosphate backbone of the nucleic acids interacts with the free nitrogen positions of the PEI and forms small micelles by cross-branching, which have a positive charge on account of the PEI. In this connection PEI with a molecular weight of 3 to 800 kDa is used. The smaller the PEI, the smaller are the formed micelles. The use of 25 kDa cross-branched PEI (Sigma-Aldrich Cat. No. 40; 872-7) leads on addition of nucleic acids to the formation of polyplexes of size 100 nm up to 500 nm, though typically to polyplexes of size 100 to 200 nm. As a rule a nitrogen/phosphate ratio of 2:1 to 5:1 is used, in some cases even up to 20:1. The packing of the nucleic acid in micelles results in a change of the zeta potential of the complex to ~(+)21 mV with a N/P ratio of 3. It is known that with increasing, positive zeta potential of complexes the toxicity to culture cells rises. These micelles are however easily taken up as endosomes by a cell by constriction of the plasma membrane. The PEI now buffers inflowing protons, as a result of which many chloride ions in the interior of the endosome lead to a swelling of the compartment on account of the osmotic pressure. This effect of PEI is described in the literature as the proton sponge effect (Sonawane et al., JBC, 2003, Vol. 278; No. 45(7) pp. 44826-44831) and ultimately leads to the rupture of the endosome and to the release of the spiegelmers into the cytosol.

The nucleic acid-PEI complex has a tendency on account of a strongly positive charge to interaction and aggregation with serum proteins, and also to exhibit the aforedescribed cell toxicity. Thus, it has been described in the literature that high doses of nucleic acid-PEI micelles after subcutaneous and intravenous injection in rats can rapidly lead to an accumulation in the lungs and thus to embolisms/infarcts. The solution to this problem is to derivatise the nucleic acid with 2 kDa polyethylene glycol (PEG). These residues surround the micelles like a shield and prevent the binding to serum proteins (Ogris et al., Gene Therapy, 1999, 6(595-605). Furthermore, the zeta potential is reduced to +/−0 mV, which leads to a lower cell toxicity while retaining the buffer capacity of the PEI as regards the proton sponge effect.

3.2 Spiegelmer Activity with PEG2000

The lead candidates NOX-A and NOX-f were produced synthetically as aptamer and spiegelmer with a 3'-terminal amino group, and were then PEGylated via the amino radical. It was shown by means of equilibrium binding assays that PEGylation has no influence on the binding properties of the aptamers to the HMGA1a/b fragment. Furthermore, it was shown by means of competition assays with recombinant full-length HMGA1a/b that also the binding of spiegelmers to the full-length HMGA1a/b is independent of the 3'-terminal PEGylation (FIG. 9).

3.3 Spiegelmer Packing

The packing of sterile, PEGylated spiegelmer was carried out in PBS by adding 25 kDa of cross-branched polyethyleneimine (PEI) (ALDRICH, Cat.: 40,872-7) in a ratio of the absolute nitrogen fraction of the PEI to the absolute phosphate of the ribonucleic acid backbone of 2.5:1 (N/P 2.5). The sterile, autoclaved PEI solution had a concentration of 200 mM free nitrogen groups and was adjusted to a pH of 7.4 with 1 M hydrochloric acid. The sterile filtered spiegelmer was taken in a concentration of up to 700 μM in 1×PBS with Ca/Mg and after addition of sterile filtered PEI was incubated for 30-60 minutes at room temperature. Ideally the complex formation takes place with the smallest possible adjusted concentration of added spiegelmer, since high concentrations of spiegelmer lead to randomly large aggregates. The formation of spiegelmer micelles was measured by means of a dye exclusion assay. For this, it was determined how much spiegelmer can be detected by the dye before and after packing in micelles. RiboGreen (M. Probes) was used as dye, and the fluorescence was measured with an ELISA reader. 1 μM spiegelmer was added in each case to 100 μl 1×PBS and increasing amounts of PEI were added. 100 μl of 0.2 μg/μl RiboGreen were placed in a 96-well microtitre plate suitable for fluorescence, and after incubating the micelle batch for 30 minutes at room temperature 10 μl were pipetted into the microtitre plate. Starting from a N/P ratio of 2, more than 90% of the spiegelmers were present as micelles (FIG. 10). In this connection PEI alone had no influence on the fluorescence of the dye.

3.4 Stability of Spiegelmer Micelles

1 µM of spiegelmer micelles were stored under conditions specified in FIG. 11. The stability of spiegelmer micelles was measured by the dye exclusion assay described in Section 3.3 A stability study of the micelles showed that the storage of micelles in different media as well as at different temperatures has no influence on the spiegelmer micelles. The freeze drying of ribozyme/PEI complexes without any loss of the properties of the ribozyme is also described in the literature (Brus-C et al., J. Control Release, 2004, Feb., 20, 95(1), 199-31).

3.5 Uptake of Spiegelmer Micelles

The intracellular uptake of spiegelmer micelles was established in a cell culture system of HS578T cells. $1 \times 10^4$ HS578T cells were allowed to grow on sterile 20 mm size cover classes to a confluence of 30-40%. 5'-labelled spiegelmer NOX-A-3'-PEG was packed with a N/P ratio 2.5:1 in micelles, added in a concentration of 1 µM to the cells, and incubated for 16 hours at 37° C. As control for the passive uptake of spiegelmers, 1 µM of pure fluorescence-labelled spiegelmer was in each case incubated with the cells. The cells were then washed three times with 1 ml of PBS and fixed for 30 minutes with 3% paraformaldehyde. The preparations were again washed three times with 1 ml of PBS, incubated for a further 10-20 seconds with a DAPI solution (1 µl stock to 10 ml 1×PBS) to stain the chomatin in the cell nucleus, washed once more, and covered with a mounting solution. The preparations prepared in this way were analysed in a fluorescence microscope (emission 488 nm/extinction 514-522 nm).

It was shown that spiegelmer micelles have a higher transfection rate compared to "naked", unpacked spiegelmers (FIG. 12)

The transfection efficiency was in this connection >95% of all cells and had no influence on the morphology of the cells. The 5'-FITC-coupled spiegelmer was mainly to be found in the cytosol and associated with the plasma membrane. The point-like distribution indicates an inclusion in compartments and the diffuse pattern points to released spiegelmer. Only a slight spiegelmer signal could be detected in the cell nucleus.

3.6 Release of Spiegelmer

The point-like distribution of the spiegelmer in the cytosol and perinuclear space of the H578T cells points to an accumulation in compartments of the cells, for example endosomes. To check the release of the spiegelmers from these compartments the distribution pattern of individual, greatly enlarged cells was analysed (FIG. 13). In addition to the point-like localisation of the spiegelmers, a diffuse distribution pattern in the cytosol and on the plasma membrane was detected, which points to the endosomal release of the spiegelmers. This pattern was not found in the case of "naked" spiegelmers.

EXAMPLE 4

Bioactivity In Vivo 4.1 Proliferation Assay without PEI

Effect on the Proliferation of MCF-7 Cells

The potential role of HMGA1a/b in cell division was investigated by means of proliferation assays. First of all spiegelmer was added in a high dose as "naked" nucleic acid to the cell culture medium and the growth of the cells was followed over time The breast cancer cell line MCF-7 was used as model, since in these cells a smaller (antagonising) expression of HMGA1a/b was found, and the role of HMGA1a/b in the proliferation of these cells had already been described in the literature. Reeves et al. (Reeves-R et al., Molecular and Cellular Biology, January 2001, p 575-594) showed that the over-expression of HMGA1a/b in MCF-7 cells leads to an increased proliferation, and the inhibition of HMGA1a/b by means of expressed antisense constructs inhibits the proliferation of MCF-7 cells.

Execution/Method $0.5 \times 10^4$ MCF-7 cells (ATCC) were seeded out in 96-well plates (Costar) with a flat, transparent base and cultured for 16-24 hours in 100 µl RPMI 1640 medium with 10% foetal calf serum (FCS). The cells were then washed with PBS and cultured for a further 48 hours with standard cell culture medium with the direct addition of sterile filtered spiegelmer. This was followed by the addition of 10 µl of a resazurin solution (0.44 mM in PBS) to the respective batches and further incubation for 2 hours at 37° C. The transformation of resazurin by the cell metabolism correlates directly with the number of cells. The change in colour was measured in a Fluostar Optima multidetection plate reading device (BMG) (emission 544 nm, extinction 590 nm). Each value was determined three times per experiment and referred to the values of untreated control cells.

Result

NOX-A inhibited after two days in a dose-dependent manner the proliferation of MCF-7 cells (n=12) (FIG. 14). The maximum inhibition of the proliferation to ca. 30% of the value of untreated cells was found at 40 µM. At concentrations up to 40 µM no non-specific effect of the inverse control spiegelmer was found.

4.2 Proliferation Assay with PEI

Effect of Spiegelmer Micelles on the Proliferation of H-1299 Cells

Execution/Method $1 \times 10^4$ NCI-H-1299 cells (lung carcinoma cells; ATCC) were seeded out in 24-well plates (Costar) with a flat, transparent base and cultured for 16-24 hours in 1 ml RPMI 1640 medium with a 10% FCS. The cells were then washed twice with PBS and cultured for a further three days with cell culture medium containing 1% FCS and spiegelmer micelles. The packing of sterile, PEGylated spieglemer was carried out beforehand in PBS by adding 25 kDa cross-branched polyethyleneimine (PEI) (Sigma) in a ratio of the absolute nitrogen fraction of the PEI to the absolute phosphate of the ribonucleic acid backbone of 2.5:1 (N/P 2.5). The sterile spiegelmer was used in a concentration of 30 µM and after the addition of the PEI was incubated for 30-60 minutes at room temperature. The spiegelmer micelles were then diluted to 1 µM with cell culture medium containing 1% FCS, added directly to the washed cells, and incubated for three days at 37° C.

This was followed by addition of 100 µl resazurin solution to the respective batches and further incubation for 2 hours at 37° C. The transformation of resazurin by the cell metabolism correlates directly with the number of cells. 100 µl were removed from the batches, transferred to a 96-well plate, and the colour change was measured in a Fluostar Optima multidetection plate reading device (BMG) (emission 544 nm, extinction 590 nm). Each value was determined twice per experiment and referred to the values of untreated control cells.

Result

The use of PEI (N/P 2.5) with 1 µM spiegelmer did not initially have any effect on cell proliferation. By reducing the amount of FKS in the cell culture medium to below 1% it was shown that the transfection with spiegelmer micelles has an influence on the proliferation of H-1299 cells, which was not previously visible with $10^96$ FKS (FIG. 15). Possibly FKS stimulates the proliferation to such an extent that the slight effect could not be observed. The reduction of the FKS concentration in MCF-7 cells lead to the death of the cells over a period of 3 days.

4.3 Inhibition Tumour Marker cdc25a (with PEI)

Effect on the HMGA1a/b-mediated regulation of cell cycle factors, in the example of the potential oncogene cdc25a.

Reeves et al. (Molecular and Cellular Biology, January 2001, p 575-594) showed by means of cDNA arrays through over-expression of HMGA1a/b in MCF-7 cells that HMGA1a/b induces the expression of a large number of genes. At the same time cell cycle factors and growth factors such as for example cdc25a, identified as a potential oncogene (cell division cycle 25a phosphotase), which plays a decisive role in the control of the transition from the G1 phase to the S phase of the cell cycle, are over-expressed by a factor of up to 100. The activation of such control points leads after inhibition of the cell cycle progression either to the transcription of genes which are involved in DNA repair or, if the DNA damage is irreparable, to the induction of apoptosis. As cell culture test system H-1299 cells were chosen for this purpose, since they have already exhibited an increased expression of HMGA1a/b.

Execution/Method $1\times10^4$ H-1299 cells were seeded out in 24-well plates (Costar) with a flat, transparent floor and cultured for 16-24 hours in RPMI 1640 medium containing 10% FCS (volume 1 ml). The cells were then washed twice with PBS and cultured for a further three days in cell culture medium with spiegelmer micelles containing 10% FCS. The packing of sterile, PEGylated spiegelmer was carried out beforehand in PBS by adding 25 kDa cross-branched polyethyleneimine (PEI) (Sigma) in a ratio of the absolute nitrogen fraction of the PEI to the absolute phosphate of the ribonucleic acid backbone of 2.5:1 (N/P 2.5). The sterile spiegelmer was used in a concentration of 30 µM and, after adding PEI, was incubated for 30-60 minutes at room temperature. The spiegelmer micelles with cell culture medium containing 1% FCS were then diluted to the respective concentration, added directly to the washed cells, and incubated for three days at 37° C. The cells were washed twice with PBS and harvested by means of a cell scraper. The mRNA of the cells was then isolated from the cells by means of Roti-Quick-Kits (Roth, Cat. No. 979.1) and 0.2-1 µg of total RNA was used as template for the PCR of cdc25a and GAPDH.

The primers for the amplification of GAPDH were as follows: forward primer: 5'-ACATGTTCCAATATGATTCC-3' and reverse primer: 5-TGGACTCCACGACGTACTCAG-3' at an annealing temperature of 51° C., and for the amplification of cdc25a: forward primer: 5'-GAGGAGTCTCACCTG-GAAGTACA-3' and reverse primer 5'-GCCATTCAAAAC-CAGATGCCATAA-3' at an annealing temperature of 59° C. The PCR conditions were as follows: 0.2-0.75 µM primer, 1.5 mM MgCl2 and 0.2 mM dNTPs. Every two PCR cycles an aliquot of 5 µl was quantified by PicoGreen and evaluated by correlation with GAPDH as load control: for this, in the first step for each investigated sample the so-called "crossing point" value (CP) of the reference gene is subtracted from the CP value of the gene being investigated (dCP=CP target gene minus CP reference gene). CP is defined as the number of PCR cycles that are required in order to reach a constantly defined fluorescence value. The same amount of newly synthesised DNA is found at the CP in all reaction vessels. After this standardisation the dCP value of a control (in this case GAPDH) is subtracted from the dCP value of the experimentally treated samples; one arrives at the so-called "delta-delta CT" calculation model. The relative expression difference of a sample between the treatment and the control (ratio), normalised to the reference gene and referred to a standard sample, is found from the arithmetic formula $2^{-ddCP}$.

$$dCP=CP(cdc25a)-CP(GAPDH)$$

$$ddCP=dCP(\text{treatment spiegelmer NOX-}A)-dCP(\text{control: PBS or NOX-A inverse})$$

$$\text{Ratio}=2^{-ddCP}$$

Result cdc25a and HMGA1a/b were detected in MCF-7 and H-1299 cells by means of RT-PCR. MCF-7 cells showed with a low expression of HMGA1a/b also a low expression of cdc25a, whereas HMGA1a/b and cdc25a were strongly expressed in H-1299 cells. The transfection of H-1299 cells for two days with HMGA1a/b-binding spiegelmers led to a significant, dose-dependent reduction of the expression of cdc25a mRNA (FIG. 16 and FIG. 17).

Up to a concentration of 4 µM a control speigelmer exhibited no non-specific effect, neither on the GAPDH nor on the cdc25a mRNA expression. From this it can be concluded that the HMGA1a/b-induced over-expression of the potential oncogene cdc25a can be inhibited by means of spiegelmers.

EXAMPLE 5

Effectiveness Study: Xenograft Model

Effect of Spiegelmers on Tumour Growth In Vivo

In order to test the hypothesis that HMGA1a/b-binding spiegelmers inhibit the growth of tumours in vivo, a xenograft model was developed for the strongly HMGA1a/b-expressing pancreatic carcinoma cells PSN-1. On the basis of this model a therapeutic experiment was carried out with 2 mg/kg NOX-A spiegelmer micelles at a N/P of 2.5 (see Example 3, paragraph 3.3).

Execution/Method

Male naked mice (NMRI: nu/nu) (group size n=8) were subcutaneously injected in the side with in each case $10^7$ PSN-1 cells (ECACC) and the tumour growth was observed over 22 days. The animals had a mean weight of 25-27 g and were 6-8 weeks old. The active spiegelmer NOX-A-3'PEG and the inverse control spiegelmer in INV-3'PEG were packed in micelles as described above by adding PEI in a N/P ratio of 2.5. 100 µl of the spiegelmer micelle suspension (corresponding to 3.46 nmole/animal or 2 mg/kg) were in each case subcutaneously injected daily into the vicinity of the tumour. The tumour volume and bodyweight were measured three times a week. The animals were sacrificed on day 22 and the distribution of NOX-A in the plasma, liver, kidneys and tumour was quantified.

For this purpose the tissues were homogenised in hybridisation buffer (0.5×SSC pH 7.0; 0.5% (w/v) SDSarcosinate) and centrifuged for 10 mins at 4000×g. The supernatants obtained were stored at −20° C. until further use.

The amount of spiegelmer in the plasma samples and in the tissue homogenates was investigated by means of a hybridisation assay (Drolet et al. (2000) Pharm. Res. 17:1503). The hybridisation assay is based on the following principle: the spiegelmer to be detected (L-RNA molecule) is hybridised on an immobilised L-DNA oligonucleotide probe (=capture probe NOX-A; in this case: 5'-CCCATATCCACCCACG-TATCAGCCTTTTTTTT-NH2-3'; complementary to the 5' end of HMGA1a/b-NOX-A) and detected with a biotinylated detection L-DNA probe (=detector probe NOX-A; in this case: 5'-biotin-TTTTTTTTGGCTGAAACCACCCA-CATGG-3'; complementary to the 3' end of HMGA1a/b-NOX-A). For this purpose a streptavidin alkaline phosphatase conjugate is in a further step bound to the complex. After adding a chemiluminescence substrate light is generated and measured in a luminometer.

Immobilisation of the oligonucleotide probe: 100 µl of the capture probe (0.75 pmole/ml in coupling buffer: 500 mM $Na_2HPO_4$, pH 8.5, 0.5 mM EDTA) were transferred to each well (depression in a plate) in DNA-BIND plates (Corning Costar) and incubated overnight at 4° C. The probe was then washed three times with 200 µl of coupling buffer each time and incubated for 1 hour at 37° C. with in each case 200 µl of blocking buffer (0.50 (w/v) BSA in coupling buffer). After washing again with 200 µl of coupling buffer and 3×200 µl hybridisation buffer the plates can be used for the detection.

Hybridisation and detection: 10 µl EDTA plasma or tissue homogenate were mixed with 90 µl of detection buffer (2 pmole/µl of detector probe in hybridisation buffer) and centrifuged. Further purifications were carried out as necessary. The batches were then denatured for 10 mins at 95° C., transferred to the suitably prepared DNA-BIND wells (see above) and incubated for 45 mins at ca. 40° C. The following wash steps were then carried out: 2×200 µl hybridisation buffer and 3×200 µl 1×TBS/Tween 20 (20 mM Tris-Cl pH 7.6, 137 mM NaCl, 0.1% (v/v) Tween 20). 1 µl streptavidin alkaline phosphatase conjugate (Promega) was diluted with 5 ml of TBS/Tween 20. 100 µl of the diluted conjugate were added to each well and incubated for 1 hour at room temperature. The following wash steps were then carried out: 2×200 µl TBS/Tween 20 and 2×200 µl of assay buffer (20 mM Tris-Cl pH 9.8, 1 mM $MgCl_2$). 100 µl of CSPD "Ready-To-Use Substrate" (Applied Biosystems) were then added, incubated for 30 mins at room temperature, and the chemiluminescence was measured in a Fluostar Optima multidetecton plate reading device (BMG).
Result In a preliminary experiment it was shown that H-1299 cells after transplanting as a tumour grew significantly more slowly than PSN-1, and on comparing the individual animals exhibited an inhomogeneous tumour growth and therefore appeared unsuitable as xenograft model for a treatment study. PSN-1 cells exhibited an aggressive tumour growth within 22 days. It was shown that NOX-A nicelles at a dose of 2 mg/kg reduced the growth of PSN-1 tumours significantly compared to the PBS control (FIG. 18). The weight of the animals was unaffected by the treatment with spiegelmer micelles. The control spiegelmer did not exhibit any non-specific inhibition of the tumour growth and likewise had no effect on the weight of the animals. The differences in tumour sizes were, from day 10 of the treatment with NOX-A3'PEG micelles, significant or highly significant compared to untreated animals (PBS control (student's t-test). The end point analysis after 22 days showed a highly significant, specific reduction in tumour growth (p=0.0098 compared to PBS and p=0.022 compared to inverse control spiegelmer) (FIG. 19). Mice treated with PBS showed an average tumour growth of 2.5 $cm^3$, animals treated with controlled spiegelmer had an average tumour volume of 2.6 $cm^3$ and animals treated with NOX-A had an average tumour volume of 1.2 $cm^3$ after 22 days (box-and-whisker analysis). This corresponds to a reduction of the tumour growth of more than 50%.

The analysis of the tissue distribution of NOX-A showed a high concentration in the tumour (FIG. 20).

EXAMPLE 6

Comparison of the In Vivo Tissue Distribution of Packed and Unpacked Spiegelmer

In order to check the efficient incorporation of spiegelmer micelles, a non-functional spiegelmer (Proof Of Concept=POC) was PEGylated at the 3' end with PEG 2 kDa and packed with a nitrogen/phosphate ratio (N/P) of 2.5 in micelles (see Example 3, paragraph 3.3). In a similar way to the protocol described in Example 5, this approach was adopted for spiegelmer packed in micelles as well as for free, unpacked spiegelmer.
Execution/Method Male naked mice (NMRI: nu/nu) (group size n=8) were in each case injected subcutaneously in the side with $10^7$ PSN-1 cells (ECACC) and the tumour growth was observed over 25 days. The animals had a mean weight of 25-27 g and were 6-8 weeks old. The non-functional spiegelmer POC-3'PEG was packed in micelles by adding PEI in a N/P ratio of 2.5, as described above. Spiegelmer POC-3'PEG not packed in micelles served as control for the incorporation not mediated by PEI. 100 µl of the spiegelmer-micelle suspension or spiegelmer solution (corresponding to 1500 nmole/kg and 2000 nmole/kg) were injected daily subcutaneously into the vicinity of the tumour. The tumour volume and body weight were measured three times a week. 24 and 96 hours after the last injection two animals from each group were sacrificed and the distribution of POC-3'PEG (packed/unpacked) in the plasma, brain, heart, lungs, liver, kidneys, gallbladder, pancreas and tumour was quantified.

For this purpose the tissue was homogenised in hybridisation buffer (0.5×SSC pH 7.0; 0.5% (w/v) SDSarcosinate) and centrifuged for 10 mins at 4000×g. The resultant supernatants were stored at −20° C. until further use.

The amount of spiegelmer in the plasma samples and in the tissues homogenates was investigated by means of a hybridisation assay (Drolet et al. (2000) Pharm. Res. 17:1503). The assay is based on the following principle: the spiegelmer (L-RNA molecule) to be detected is hybridised on an immobilised L-DNA oligonucleotide probe (=capture probe POC; here: 5'-NH2(C7) -TTTTTTTTTTAGCTCTGCACAGCGCT-3'; complementary to the 3' end of POC) and is detected with a biotinylated detection L-DNA probe (=detector probe POC; here: 5'-CCGCATCAGACCGAGTTTCCTTATTTTTTTT-Biotin-3'; complementary to the 5' end of POC). For this, a streptavidin alkaline phosphatase conjugate was bound in a further step to the complex. After addition of a chemiluminescence substrate, light is generated and measured in a luminometer.

Immobilisation of the oligonucleotide probe: 100 µl of the POC capture probe (0.75 pmole/ml in coupling buffer: 500 mM $Na_2HPO_4$ pH 8.5, 0.5 mM EDTA) were transferred to each well (depression in a plate) in DNA-BIND plates (Corning Costar) and incubated overnight at 4° C. The probe was then washed three times with 200 µl of coupling buffer and incubated for 1 hour at 37° C. with 200 µl of blocking buffer (0.5% (w/v) BSA in coupling buffer). After washing again with 200 µl of coupling buffer and 3×200 µl of hybridisation buffer, the plates can be used for the detection.

Hybridisation and detection: 10 µl of EDTA plasma or tissue homogenate were mixed with 90 µl of detection buffer (2 pmole/µl POC detector probe in hybridisation buffer) and centrifuged. Further purifications were carried out as necessary. The batches were then denatured for 10 mins at 95° C., transferred to the suitably prepared DNA-BIND wells (see above), and incubated for 45 mins at ca. 40° C. The following wash steps were then carried out: 2×200 µl of hybridisation buffer and 3×200 µl 1×TBS/Tween 20 (20 mM Tris-Cl pH 7.6, 137 mM NaCl, 0.1% (v/v) Tween 20). 1 µl of streptavidin alkaline phosphatase conjugate (Promega) was diluted with 5 ml of 1×TBS/Tween 20. 100 µl of the dilute conjugate were added to each well and incubated for one hour at room temperature. The following wash steps were then carried out: 2×200 µl of 1×TBS/Tween 20 and 2×200 µl of 1× assay buffer (20 mM Tris-Cl pH 9.8, 1 mM $MgCl_2$). 100 µl of CSPD "Ready-To-Use Substrate" (Applied Biosystems) were then added, incubated for 30 mins at room temperature, and the chemiluminescence was measured in a Fluostar Optima multidetection plate reading device (BMG).

Result

The analysis of the weight distribution of the non-functional spiegelmer POC-3'PEG, which was packed in micelles, showed after 24 hours a significantly higher concentration in the tumour tissues (24.925+/−13.301 pmole/mg) compared to the unpacked spiegelmer (0.840+/−0.255 pmole/mg) (FIG. 21 A). Whereas the concentration of the packed spiegelmer had halved (11.325+/−7.050 pmole/mg) after a further three days (96 hours), only a very small amount of the unpacked spiegelmer could be detected (0.120+/−0.057 pmole/mg).

The plasma level of unpacked spiegelmer (2.950+/−0.438 pmole/ml) after 24 hours was comparable to that of the PEI-packed spiegelmer (1.930+/−2.729 pmole/ml). After 96 hours clear differences were found, in which about four times the amount of packed spiegelmer compared to the unpacked spiegelmer was detected.

A slight accumulation in the kidneys was observed after 24 hours for both formulations, whereas a slight accumulation in the liver and gallbladder was found only for unpacked spiegelmer. After 96 hours, for both formulations only minor amounts of spiegelmer were detected in the liver and kidneys. On the other hand, slightly raised values were found in the gallbladder and pancreas (but with a high standard deviation) for packed spiegelmer compared to unpacked spiegelmer.

To summarise, compared to the weight distribution (24 and 96 hours after the last injection) of spiegelmers in the presence and absence of PEI, it was found that spiegelmer micelles have a significantly prolonged residence time in the plasma and tumour compared to unpacked material (FIG. 21B) and thus represent a promising approach to the use of spiegelmers directed against intracellular target molecules.

The following citations are incorporated herein by way of reference.

Abe et al. J Gastroenterol. 2003; 38, 1144-9
Abe N et al (1999). Cancer Res 59:1169-1174
Abe N et al (2000). Cancer Res 60:3117-3122
Abe N et al (2002). Pancreas 25:198-204
Anand A & Chada K (2000). Nat Genet 24 :377-380
Balcercak et al, Postepy Biochem, 2005; 51(3):261-9
Balcerczak et al Pathol Res Pract 2003; 199, 641-6
Baldassarre G et al (2003). Mol Cell Biol 23:2225-2238
Bandiera S et al (1998). Cancer Res 58:426-431
Battista S et al (1998) Oncogene 17:377-385
Belge G et al (1992). Cell Biol Int Rep 16 :339-347
Berlingieri M T et al. (1995). Mol Cell Biol 15:1545-1553
Birdsal S H et al (1992). Cancer Gen Cytogen 60:74-77
Bridge J A et al (1992). Cancer Detect Prevent 16:215-219
Briese et al. Int. J Gynevol Pathol 2006 January, 65-9
Bullerdiek J et al (1987). Cytogenet Cell Genet 45 :187-190
Bussemakers M J G et al (1991). Cancer Res 51:606-611
Chada K et al (2004). U.S. Pat. No. 6,756,355
Chang et al. Dig Dis Sci, 2005 October, 1764-70
Chau K Y et al (2000). J Neurosci 20 :7317-7324
Chau K Y et al (2003). Mol Med 9 :154-165
Chen et al. Cancer Epidemiol Biomarkers Prev 2004 January, 30-3
Chiappetta et al. Clin Cancer Res. 2004 November, 7634-44
Chiappetta G et al (1995). Oncogene 10:1307-1314
Chiappetta G et al (1996). Oncogene 13:2439-2446
Chiappetta G et al (1998). Cancer Res 58:4193-4198
Chiappetta G et al (2001). Int J Cancer 91:147-151
Chin M T et al (1999). J Mol Cell Cardiol 31:2199-2205
Chuma et al, Keio J Med 2004 June, 90-7
Cuff C A et al (2001). J Clin Invest 108 :1031-1040
Czyz et al. Langenbecks Arch Surg 2004, June, 193-7
Dal Cin P et al (1993). Genes Chromosomes Cancer 8:131-133
Dal Cin P et al (1995). Cancer Res 55:1565-1568
Diana F et al (2001). J Biol Chem 276 :11354-11361
Dolde C E et al (2002). Breast Cancer Res Treat 71:181-191
Donato et al. Oncol Rep 2004 June, 1209-13
Du W et al (1993). Cell 74 :887-898
Evans A et al (2004). J Surg Oncol 88 :86-99
Fedele M et al (1996). Cancer Res 56:1896-1901
Fletcher A J et al (1991). Am J Pathol 138:1199-1207
Fletcher A J et al (1992). Cancer Res 52 :6224-6228
Fletcher A J et al (1995). Genes Chromosomes Cancer 12:220-223
Flohr et al. Histol Histopathol 2003 October, 999-1004
Foster L C et al (1998). J Biol Chem 273 :20341-20346
Foster L C et al (2000). FASEB J 14 :368-378
French et al. Mol Cell Biol 1996, 5393-9
Friedman M et al (1993). Nucleic Acids Res 21:4259-4267
Giancotti V et al (1987). EMBO J 6:1981-1987
Giancotti V et al (1989). Exp Cell Res 184:538-545
Giancotti V et al. (1993). Eur J Biochem 213:825-832
Giannini G et al (1999). Cancer Res 59:2484-2492
Giannini G et al (2000). Br J Cancer 83:1503-1509
Grosschedl R et al (1994). Trends Genet 10 :94-100
Heim S et al (1988). Cancer Genet Cytogenet 32:13-17
Henderson et al J Virol 2000, 10523-34
Hindmarsh et al. J. Virol 1999, 2994-3003
Holth L T et al (1997). DNA Cell Biol 16:1299-1309
Huth J R et al (1997). Nat Struct Biol 4:657-665
Jain M et al (1996). J Clin Invest 97 :596-603
Johansson M et al (1992). Cancer Genet Cytogenet 60 :219-220
Johansson M et al (1993). Br J Cancer 67 :1236-1241
Johnson K R et al (1990). Exp Cell Res 187:69-76
Kazmierczak B et al (1995). Cancer Res 55 :2497-2499
Kettunen et al. Cancer Genet Cytogenet 2004 March, 98-106
Kim D H et al (1999). Int J Cancer 84 :376-380
Klotzbücher M et al (1999). Am J Pathol 155:1535-1542
Kottickal L V et al (1998). Biochem Biophys Res Commun 242 :452-456
Lee et al. Int J Oncol 2004, April, 847-51
Leger et al. Mol Cell Biol 1995, 3738-47
Leman E S et al (2003). J Cell Biochem 88 :599-608
Li et al J. Virol 1998, 2125-31
Li et al, Am J Dermatopathol 2004 August, 267-72
Mandahl N et al (1987). Int J Cancer 39 :685-688
Mandahl N et al (1989). Cancer 65 :242-248
Mandahl N et al (1993). Cancer 71 : 3009-3013
Mark J & Dahlenfors R (1986). Anticancer Res 6:299-308
Mark J et al (1980). Cancer Genet Cytogenet 2 :231-241
Mark J et al (1988). Anticancer Res 8:621-626
Masciullo et al Carcinogenesis 2003 July, 1191-8
Masciullo V et al (2003). Carcinogenesis 24:1191-1198

Melillo R M et al (2001). Mol Cell Biol 21:2485-2495
Nam et al Histopathology 2003 May, 466-71
Nestl A et al (2001). Cancer Res 61:1569-1577
Noguera R et al (1989). Virchows Arch A Pathol Anat Histopathol 415:377-382
Ogram SA et al (1997). J Biol Chem 270:14235-14242
Ozisik Y Y et al (1993). Cancer Genet Cytogenet 79:136-138
Panagiotidis et al Virology 1999, 64-74
Pellacani A et al (1999). J Biol Chem 274:1525-1532
Peters et al. Cancer Epidemiol Biomarkers Prev 2005, Jul. 17, 17-23
Pierantoni et al. Biochem J 2003 May, 145-50
Ram T G et al (1993). Cancer Res 53:2655-2660
Reeves R & Beckerbauer K (2002). Progr Cell Cycle Res 5:279-286
Reeves R & Beckerbauer L (2001). Biochim Biophys Acta 1519:13-29
Reeves R & Nissen M S (1990). J Biol Chem 265:8573-8582
Reeves R et al (2001). Mol Cell Biol 21:575-594
Rogalla P et al (1996). Am J Pathol 149:775-779
Rohen C et al (1995). Cancer Genet Cytogenet 84:82-84
Sarhadi et al. J Pathol Mar. 6, 2006, Epup ahead of print
Sato et al. Pathol Res Pract, 2005; 201, 333-9
Scala S et al (2000). Proc Natl Acad Sci USA 97:4256-4261
Schaefer et al. Mol Cell Biol. 1997, 873-86
Schlueter et al. Pathol Res Pract, 2005; 201, 101-7
Schoenmakers E F P M et al. (1995). Nat Genet 10:436-444
Sgarra R et al (2003). Biochemistry 42:3575-3585
Sgarra R et al (2004). FEES Lett 574:1-8
Sreekantaiah C et al (1990). Cancer Genet Cytogenet 45:81-84
Sreekantaiah C et al (1991). Cancer Res 5:422-433
Staats B et al (1996). Breast Cancer Res Treat 38:299-303
Tamimi Y et al (1996). Br J Cancer 74:573-578
Tapasso F et al (2004). Cancer Gene Ther 11:633-641
Tarbe N et al (2001). Anticancer Res 21:3221-3228
Thanos D & Maniatis T (1992). Cell 71:777-789
Turc-Carel C et al (1986). Cancer Genet Cytogenet 23:283-289
Vallone D et al (1997). EMBO J 16:5310-5321
Van Maele et al., Trends Biochem Sci 2006, 98-105
Vanni R et al (1988). Cancer Genet Cytogenet 32:33-34
Vanni R et al (1993). Cancer Genet Cytogenet 68:32-33
Walter T A et al (1989). Cancer Genet Cytogenet 41:99-103
Wolffe A P (1994). Science 264:1100-1101
Wood L J et al (2000a). Cancer Res 60:4256-4261
Wood L J et al (2000b). Mol Cell Biol 20:5490-5502
Xiang Y Y et al (1997). Int J Cancer 74:1-6
Zhou X et al (1995). Nature 376:771-774

The features of the invention disclosed in the preceding description, claims and drawings can be essential both individually as well as in any combination for the implementation of the invention in its various embodiments.

The invention claimed is:

1. An HMGA-binding nucleic acid comprising a first section, Box A1, and a second section, Box A2, wherein Box A1 and Box A2 are joined to one another by an intermediate portion, and wherein Box A1 and Box A2 each is, independently of one another, GGGCG, GGGUG or GGGAG, and the intermediate portion comprises (a) Z1 comprising six or seven nucleotides or (b) Z2 comprising 12 to 25 nucleotides, and the 5' end of Box A1 comprises a first portion and the 3' end of Box A2 comprises a second portion, wherein each of said first and second portions, independently of one another, comprises four to eight nucleotides.

2. The HMGA-binding, nucleic acid of claim 1 selected from the group consisting of SEQ ID NO:1, SEQ ID NO:2, SEQ ID NO:3, SEQ ID NO:5, SEQ ID NO:6, SEQ :ID NO:7, SEQ ID NO:8, SEQ NO:9, SEQ ID NO:10, SEQ ID NO:11, SEQ NO:12, SEQ NO:13, SEQ ID NO:14, SEQ ID NO:15 and SEQ ID NO:16, SEQ ID NO:22 and SEQ ID NO:24.

3. The HMGA-binding nucleic acid of claim 1, wherein the HMGA is selected from the group consisting of HMGA1, HMGA1a, HMGA1b and HMGA2.

4. A composition comprising the nucleic acid of claim 1 and a delivery vehicle.

5. The composition according to claim 4, which intracellularly delivers said nucleic acid.

6. The composition according to claim 4, wherein said delivery vehicle is selected from the group consisting of a conjugate and a physical means.

7. The composition according to claim 4, wherein said delivery vehicle is selected from the group consisting of a liposome, a nanoparticle, microparticle, a dendrimer and a cyclodextrin.

8. The composition of claim 4, wherein said delivery vehicle comprises a vesicle comprising a polypeptide, a polyethyleneimine (PEI), an amphipathic molecule or combinations thereof.

9. The composition according to claim 4, wherein said delivery vehicle comprises a conjugate, wherein said conjugate comprises a fusogenic peptide, a receptor that mediates endocytosis, a signal peptide or a lipophilic molecule.

10. The composition according to claim 4, wherein said delivery vehicle comprises electroporation, iontophoresis, pressure, ultrasound or shock waves.

11. The composition according to claim 8, wherein said PEI comprises branches, and said PEI comprises a molecular weight of about 25 kDa.

12. The composition according to claim 8, wherein said PEI forms a micelle or a micelle-like structure, 13. The composition according to claim 4, wherein said nucleic acid comprises a spiegelmer.

14. The composition according to claim 13, wherein said spiegelmer comprises a modification.

15. The composition of claim 14, wherein said modification comprises polyethylene glycol (PEG).

16. The composition according to claim 15, wherein said PEG comprises a molecular weight of about 1,000 to 10,000 Da; about 1,500 to 2,500 Da; or about 2.000 Da.

17. The composition according to claim 8, wherein ratio of nitrogen groups of the PEI to phosphate groups of the nucleic acid is about 1 to 20; about 1.5 to 10; about 2 to 5; or about 2 to 3.

18. A pharmaceutical composition comprising the nucleic acid according to claim 1, and a pharmaceutically acceptable carrier.

19. A kit for the detection of HMGA, comprising the HMGA-binding nucleic acid according to claim 1 and optional reagents.

20. A complex comprising an HMGA protein and the HMGA-binding nucleic acid according to claim 1.

21. A method for binding an HMGA comprising:
providing a cell comprising at least one HMGA,
providing the nucleic acid of claim 1, and
incubating the cell with the nucleic acid.

22. The method according to claim 21, wherein said nucleic acid comprises a spiegelmer.

* * * * *

SEQUENCE LISTING

```
<160> NUMBER OF SEQ ID NOS: 50

<210> SEQ ID NO 1
<211> LENGTH: 47
<212> TYPE: RNA
<213> ORGANISM: Artificial
<220> FEATURE:
<223> OTHER INFORMATION: synthetic

<400> SEQUENCE: 1
gcugcugcaa auugacgggg gcgugguugg ggcgggucga uugcagc            47

<210> SEQ ID NO 2
<211> LENGTH: 48
<212> TYPE: RNA
<213> ORGANISM: Artificial
<220> FEATURE:
<223> OTHER INFORMATION: synthetic

<400> SEQUENCE: 2
gcugaaugag gaucgcaggg gcguggcugg gguggcgac cguucagc             48

<210> SEQ ID NO 3
<211> LENGTH: 48
<212> TYPE: RNA
<213> ORGANISM: Artificial
<220> FEATURE:
<223> OTHER INFORMATION: synthetic

<400> SEQUENCE: 3
gcugcgcaag gagaggggcg cgguugggga ggcucuaagc gcugcagc            48

<210> SEQ ID NO 4
<211> LENGTH: 47
<212> TYPE: RNA
<213> ORGANISM: Artificial
<220> FEATURE:
<223> OTHER INFORMATION: synthetic
```

<400> SEQUENCE: 4
gcuggcgcua uaggacaggg gugcgguugg ggcgguccgc ugucagc        47

<210> SEQ ID NO 5
<211> LENGTH: 48
<212> TYPE: RNA
<213> ORGANISM: Artificial
<220> FEATURE:
<223> OTHER INFORMATION: synthetic

<400> SEQUENCE: 5
gcuggauaga acgcagggggu gcgguuuggg gugggcguga uaugcagc        48

<210> SEQ ID NO 6
<211> LENGTH: 46
<212> TYPE: RNA
<213> ORGANISM: Artificial
<220> FEATURE:
<223> OTHER INFORMATION: synthetic

<400> SEQUENCE: 6
gcugccguaa agaggggguga gguuggggag gcuuuacggu uucagc        46

<210> SEQ ID NO 7
<211> LENGTH: 48
<212> TYPE: RNA
<213> ORGANISM: Artificial
<220> FEATURE:
<223> OTHER INFORMATION: synthetic

<400> SEQUENCE: 7
gcugcaugcc gcgaucaggg gagcgguugg ggcgggaucc ggcucagc        48

<210> SEQ ID NO 8
<211> LENGTH: 48
<212> TYPE: RNA
<213> ORGANISM: Artificial
<220> FEATURE:
<223> OTHER INFORMATION: synthetic

<400> SEQUENCE: 8
gcugcgaggg agguagcggc ucugcgccgu gacgugggug gaugcagc        48

<210> SEQ ID NO 9
<211> LENGTH: 50
<212> TYPE: RNA
<213> ORGANISM: Artificial
<220> FEATURE:
<223> OTHER INFORMATION: synthetic

<400> SEQUENCE: 9
ggcugauacg uggguggaua uggggcaguu ccaugugggu gguuucagcc        50

<210> SEQ ID NO 10
<211> LENGTH: 50
<212> TYPE: RNA
<213> ORGANISM: Artificial
<220> FEATURE:
<223> OTHER INFORMATION: synthetic

<400> SEQUENCE: 10
ggcugauacg uggugaauau ggggcaguu ccaugugggu gguuucagcc        50

```
<210> SEQ ID NO 11
<211> LENGTH: 49
<212> TYPE: RNA
<213> ORGANISM: Artificial
<220> FEATURE:
<223> OTHER INFORMATION: synthetic

<400> SEQUENCE: 11
ggcugauacg ugggaggaaa gguguaacua ccugugggag guuucagcc          49

<210> SEQ ID NO 12
<211> LENGTH: 50
<212> TYPE: RNA
<213> ORGANISM: Artificial
<220> FEATURE:
<223> OTHER INFORMATION: synthetic

<400> SEQUENCE: 12
ggcuggcacu cgcaggggug aagugaugau uggggugggc gagaccagcc         50

<210> SEQ ID NO 13
<211> LENGTH: 50
<212> TYPE: RNA
<213> ORGANISM: Artificial
<220> FEATURE:
<223> OTHER INFORMATION: synthetic

<400> SEQUENCE: 13
ggcugccgag ugguuggguig guguaaggga gguggaaucc gcgggcagcc        50

<210> SEQ ID NO 14
<211> LENGTH: 50
<212> TYPE: RNA
<213> ORGANISM: Artificial
<220> FEATURE:
<223> OTHER INFORMATION: synthetic

<400> SEQUENCE: 14
ggcuguucgu gggaggaagg cucuuggaua gagucguggg ugguucagcc         50

<210> SEQ ID NO 15
<211> LENGTH: 32
<212> TYPE: RNA
<213> ORGANISM: Artificial
<220> FEATURE:
<223> OTHER INFORMATION: synthetic

<400> SEQUENCE: 15
ggaucgcagg ggcguggcug gggugggcga cc                            32

<210> SEQ ID NO 16
<211> LENGTH: 33
<212> TYPE: RNA
<213> ORGANISM: Artificial
<220> FEATURE:
<223> OTHER INFORMATION: synthetic

<400> SEQUENCE: 16
ggaucgcagg ggcguggcug ggguggggcga ucc                          33

<210> SEQ ID NO 17
<211> LENGTH: 21
<212> TYPE: PRT
<213> ORGANISM: Homo Sapiens
<220> FEATURE:
<221> NAME/KEY: MISC_FEATURE
<223> OTHER INFORMATION: HMGA1a
```

<400> SEQUENCE: 17

Glu Pro Ser Glu Val Pro Thr Pro Lys Arg Pro Arg Gly Arg Pro Lys
1               5                   10                  15

Gly Ser Lys Asn Lys
            20

<210> SEQ ID NO 18
<211> LENGTH: 106
<212> TYPE: PRT
<213> ORGANISM: Homo sapiens
<220> FEATURE:
<221> NAME/KEY: MISC_FEATURE
<223> OTHER INFORMATION: HMGA1a

<400> SEQUENCE: 18

Ser Glu Ser Ser Lys Ser Ser Gln Pro Leu Ala Ser Lys Gln Glu
1               5                   10                  15

Lys Asp Gly Thr Glu Lys Arg Gly Arg Gly Arg Pro Arg Lys Gln Pro
                20                  25                  30

Pro Val Ser Pro Gly Thr Ala Leu Val Gly Ser Gln Lys Glu Pro Ser
            35                  40                  45

Glu Val Pro Thr Pro Lys Arg Pro Arg Gly Arg Pro Lys Gly Ser Lys
50                  55                  60

Asn Lys Gly Ala Ala Lys Thr Arg Lys Thr Thr Thr Thr Pro Gly Arg
65                  70                  75                  80

Lys Pro Arg Gly Arg Pro Lys Lys Leu Glu Lys Glu Glu Glu Glu Gly
                85                  90                  95

Ile Ser Gln Glu Ser Ser Glu Glu Glu Gln
            100                 105

<210> SEQ ID NO 19
<211> LENGTH: 95
<212> TYPE: PRT
<213> ORGANISM: Homo sapiens
<220> FEATURE:
<221> NAME/KEY: MISC_FEATURE
<223> OTHER INFORMATION: HMGA1b

<400> SEQUENCE: 19

Ser Glu Ser Ser Lys Ser Ser Gln Pro Leu Ala Ser Lys Gln Glu
1               5                   10                  15

Lys Asp Gly Thr Glu Lys Arg Gly Arg Gly Arg Pro Arg Lys Gln Pro
                20                  25                  30

Pro Lys Glu Pro Ser Glu Val Pro Thr Pro Lys Arg Pro Arg Gly Arg
            35                  40                  45

Pro Lys Gly Ser Lys Asn Lys Gly Ala Ala Lys Thr Arg Lys Thr Thr
50                  55                  60

Thr Thr Pro Gly Arg Lys Pro Arg Gly Arg Pro Lys Lys Leu Glu Lys
65                  70                  75                  80

Glu Glu Glu Glu Gly Ile Ser Gln Glu Ser Ser Glu Glu Glu Gln
                85                  90                  95

<210> SEQ ID NO 20
<211> LENGTH: 108
<212> TYPE: PRT
<213> ORGANISM: Homo sapiens
<220> FEATURE:
<221> NAME/KEY: MISC_FEATURE
<223> OTHER INFORMATION: HMGA2

<400> SEQUENCE: 20

```
Ser Ala Arg Gly Glu Gly Ala Gly Gln Pro Ser Thr Ser Ala Gln Gly
 1               5                  10                  15

Gln Pro Ala Ala Pro Ala Pro Gln Lys Arg Gly Arg Gly Arg Pro Arg
            20                  25                  30

Lys Gln Gln Gln Glu Pro Thr Gly Glu Pro Ser Pro Lys Arg Pro Arg
        35                  40                  45

Gly Arg Pro Lys Gly Ser Lys Asn Lys Ser Pro Ser Lys Ala Ala Gln
    50                  55                  60

Lys Lys Ala Glu Ala Thr Gly Glu Lys Arg Pro Arg Gly Arg Pro Arg
 65                  70                  75                  80

Lys Trp Pro Gln Gln Val Val Gln Lys Lys Pro Ala Gln Glu Glu Thr
                85                  90                  95

Glu Glu Thr Ser Ser Gln Glu Ser Ala Glu Glu Asp
            100                 105
```

<210> SEQ ID NO 21
<211> LENGTH: 34
<212> TYPE: DNA
<213> ORGANISM: Artificial
<220> FEATURE:
<223> OTHER INFORMATION: synthetic

<400> SEQUENCE: 21
tcgaaaaaag caaaaaaaaa aaaaaaaaac tggc                      34

<210> SEQ ID NO 22
<211> LENGTH: 50
<212> TYPE: RNA
<213> ORGANISM: Artificial
<220> FEATURE:
<223> OTHER INFORMATION: synthetic

<400> SEQUENCE: 22
ggcugauacg uggguggaua ugggcaguu ccaugugggu gguuucagcc        50

<210> SEQ ID NO 23
<211> LENGTH: 50
<212> TYPE: RNA
<213> ORGANISM: Artificial
<220> FEATURE:
<223> OTHER INFORMATION: synthetic

<400> SEQUENCE: 23
ccgacuuugg uggguguacc uugacggggu auaggugggu gcauagucgg        50

<210> SEQ ID NO 24
<211> LENGTH: 50
<212> TYPE: RNA
<213> ORGANISM: Artificial
<220> FEATURE:
<223> OTHER INFORMATION: synthetic

<400> SEQUENCE: 24
ggcugauacg uggguggaua ugggcaguu ccauguggu gguuucagcc        50

<210> SEQ ID NO 25
<211> LENGTH: 50
<212> TYPE: RNA
<213> ORGANISM: Artificial
<220> FEATURE:
<223> OTHER INFORMATION: synthetic

<400> SEQUENCE: 25
ccgacuuugg ugguguacc uugacggggu auaggugggu gcauagucgg         50

<210> SEQ ID NO 26
<211> LENGTH: 50
<212> TYPE: RNA
<213> ORGANISM: Artificial
<220> FEATURE:
<223> OTHER INFORMATION: synthetic

<400> SEQUENCE: 26
ccgacuuugg ugguguacc uugacggggu auaggugggu gcauagucgg         50

<210> SEQ ID NO 27
<211> LENGTH: 40
<212> TYPE: RNA
<213> ORGANISM: Artificial
<220> FEATURE:
<223> OTHER INFORMATION: synthetic

<400> SEQUENCE: 27
uaaggaaacu cggucugaug cgguagcgcu gugcagagcu                   40

<210> SEQ ID NO 28
<211> LENGTH: 32
<212> TYPE: DNA
<213> ORGANISM: Artificial
<220> FEATURE:
<223> OTHER INFORMATION: synthetic

<400> SEQUENCE: 28
cccatatcca cccacgtatc agcctttttt tt                           32

<210> SEQ ID NO 29
<211> LENGTH: 28
<212> TYPE: DNA
<213> ORGANISM: Artificial
<220> FEATURE:
<223> OTHER INFORMATION: synthetic

<400> SEQUENCE: 29 tttttttgg ctgaaaccac ccacatgg                                 28

<210> SEQ ID NO 30
<211> LENGTH: 25
<212> TYPE: DNA
<213> ORGANISM: Artificial
<220> FEATURE:
<223> OTHER INFORMATION: synthetic

<400> SEQUENCE: 30 tttttttta gctctgcaca gcgct                                    25

<210> SEQ ID NO 31
<211> LENGTH: 31
<212> TYPE: DNA
<213> ORGANISM: Artificial
<220> FEATURE:
<223> OTHER INFORMATION: synthetic

<400> SEQUENCE: 31
ccgcatcaga ccgagtttcc ttattttttt t                            31

<210> SEQ ID NO 32
<211> LENGTH: 19
<212> TYPE: DNA
<213> ORGANISM: Artificial
<220> FEATURE:
<223> OTHER INFORMATION: synthetic

<400> SEQUENCE: 32
tcgacaccat gggtgagtc                                                19

<210> SEQ ID NO 33
<211> LENGTH: 21
<212> TYPE: DNA
<213> ORGANISM: Artificial
<220> FEATURE:
<223> OTHER INFORMATION: synthetic

<400> SEQUENCE: 33
gtctagaaag cttcccaact g                                             21

<210> SEQ ID NO 34
<211> LENGTH: 47
<212> TYPE: RNA
<213> ORGANISM: Artificial
<220> FEATURE:
<223> OTHER INFORMATION: synthetic

<400> SEQUENCE: 34
gcugcugcaa auugacgggg gcgugguugg ggcggucga uugcagc                  47

<210> SEQ ID NO 35
<211> LENGTH: 48
<212> TYPE: RNA
<213> ORGANISM: Artificial
<220> FEATURE:
<223> OTHER INFORMATION: synthetic

<400> SEQUENCE: 35
gcugaaugag gaucgcaggg gcguggcugg ggugggcgac cguucagc                48

<210> SEQ ID NO 36
<211> LENGTH: 48
<212> TYPE: RNA
<213> ORGANISM: Artificial
<220> FEATURE:
<223> OTHER INFORMATION: synthetic

<400> SEQUENCE: 36
gcugcgcaag gagaggggcg cgguugggga ggcucuaagc gcugcagc                48

<210> SEQ ID NO 37
<211> LENGTH: 47
<212> TYPE: RNA
<213> ORGANISM: Artificial
<220> FEATURE:
<223> OTHER INFORMATION: synthetic

<400> SEQUENCE: 37
gcuggcgcua uaggacaggg gugcgguugg ggcgguccgc ugucagc                 47

<210> SEQ ID NO 38
<211> LENGTH: 48
<212> TYPE: RNA
<213> ORGANISM: Artificial
<220> FEATURE:
<223> OTHER INFORMATION: synthetic

```
<400> SEQUENCE: 38
gcuggauaga acgcagggu gcgguuuggg gugggcguga uaugcagc                    48

<210> SEQ ID NO 39
<211> LENGTH: 46
<212> TYPE: RNA
<213> ORGANISM: Artificial
<220> FEATURE:
<223> OTHER INFORMATION: synthetic

<400> SEQUENCE: 39
gcugccguaa agagggguga gguugggag gcuuuacggu uucagc                     46

<210> SEQ ID NO 40
<211> LENGTH: 48
<212> TYPE: RNA
<213> ORGANISM: Artificial
<220> FEATURE:
<223> OTHER INFORMATION: synthetic

<400> SEQUENCE: 40
gcugcaugcc gcgaucaggg gagcgguugg ggcgggaucc ggcucagc                   48

<210> SEQ ID NO 41
<211> LENGTH: 48
<212> TYPE: RNA
<213> ORGANISM: Artificial
<220> FEATURE:
<223> OTHER INFORMATION: synthetic

<400> SEQUENCE: 41
gcugcgaggg agguagcggc ucugcgccgu gacgugggug gaugcagc                   48

<210> SEQ ID NO 42
<211> LENGTH: 50
<212> TYPE: RNA
<213> ORGANISM: Artificial
<220> FEATURE:
<223> OTHER INFORMATION: synthetic

<400> SEQUENCE: 42
ggcugauacg uggguggaua uggggcaguu ccaugugggu gguuucagcc                 50

<210> SEQ ID NO 43
<211> LENGTH: 50
<212> TYPE: RNA
<213> ORGANISM: Artificial
<220> FEATURE:
<223> OTHER INFORMATION: synthetic

<400> SEQUENCE: 43
ggcugauacg ugggugaaua uggggcaguu ccaugugggu gguuucagcc                 50

<210> SEQ ID NO 44
<211> LENGTH: 49
<212> TYPE: RNA
<213> ORGANISM: Artificial
<220> FEATURE:
<223> OTHER INFORMATION: synthetic

<400> SEQUENCE: 44
ggcugauacg ugggaggaaa gguguaacua ccuguggag guuucagcc                   49
```

```
<210> SEQ ID NO 45
<211> LENGTH: 50
<212> TYPE: RNA
<213> ORGANISM: Artificial
<220> FEATURE:
<223> OTHER INFORMATION: synthetic

<400> SEQUENCE: 45
ggcuggcacu cgcagggggug aagugaugau uggggugggc gagaccagcc          50

<210> SEQ ID NO 46
<211> LENGTH: 50
<212> TYPE: RNA
<213> ORGANISM: Artificial
<220> FEATURE:
<223> OTHER INFORMATION: synthetic

<400> SEQUENCE: 46
ggcugccgag ugguugggug guguaaggga gguggaaucc gcgggcagcc          50

<210> SEQ ID NO 47
<211> LENGTH: 50
<212> TYPE: RNA
<213> ORGANISM: Artificial
<220> FEATURE:
<223> OTHER INFORMATION: synthetic

<400> SEQUENCE: 47
ggcuguucgu gggaggaagg cucuuggaua gagucguggg ugguucagcc          50

<210> SEQ ID NO 48
<211> LENGTH: 32
<212> TYPE: RNA
<213> ORGANISM: Artificial
<220> FEATURE:
<223> OTHER INFORMATION: synthetic

<400> SEQUENCE: 48
ggaucgcagg ggcguggcug ggguggggcga cc                            32

<210> SEQ ID NO 49
<211> LENGTH: 33
<212> TYPE: RNA
<213> ORGANISM: Artificial
<220> FEATURE:
<223> OTHER INFORMATION: synthetic

<400> SEQUENCE: 49
ggaucgcagg ggcguggcug ggguggggcga ucc                           33

<210> SEQ ID NO 50
<211> LENGTH: 31
<212> TYPE: DNA
<213> ORGANISM: Artificial
<220> FEATURE:
<223> OTHER INFORMATION: synthetic

<400> SEQUENCE: 50
gccagttttt tttttttttt tttgctttt t                               31
```